US012790343B2

(12) United States Patent
Proulx-Lafrance et al.

(10) Patent No.: US 12,790,343 B2
(45) **Date of Patent: *Nov. 10, 2026**

(54) SOLID FORMS OF PYRAZOLO[3,4-D]PYRIMIDINE COMPOUNDS

(71) Applicant: Pfizer Inc., New York, NY (US)

(72) Inventors: Caroline Yvette Proulx-Lafrance, Natick, MA (US); John C. Amedio, Jr., Burlington, MA (US); Erika Volckova, Concord, MA (US)

(73) Assignee: Pfizer Inc., New York, NY (US)

( * ) Notice: Subject to any disclaimer, the term of this patent is extended or adjusted under 35 U.S.C. 154(b) by 275 days.

This patent is subject to a terminal disclaimer.

(21) Appl. No.: 18/655,795

(22) Filed: May 6, 2024

(65) Prior Publication Data

US 2024/0300961 A1 Sep. 12, 2024

Related U.S. Application Data

(63) Continuation of application No. 18/082,622, filed on Dec. 16, 2022, now Pat. No. 12,012,412.

(60) Provisional application No. 63/290,136, filed on Dec. 16, 2021.

(51) Int. Cl.

| | |
|---|---|
| ***C07D 487/04*** | (2006.01) |
| ***A61K 31/519*** | (2006.01) |
| ***A61P 9/00*** | (2006.01) |

(52) U.S. Cl.

CPC ........ *C07D 487/04* (2013.01); *C07B 2200/13* (2013.01)

(58) Field of Classification Search

CPC .......................... C07D 487/04; C07B 2200/13

See application file for complete search history.

(56) References Cited

U.S. PATENT DOCUMENTS

| | | | |
|---|---|---|---|
| 7,964,607 B2 | 6/2011 | Verhoest et al. | |
| 8,623,879 B2 | 1/2014 | Giovannini et al. | |
| 12,012,412 B2 * | 6/2024 | Proulx-Lafrance .......................... | C07D 487/04 |
| 2009/0030003 A1 | 1/2009 | Verhoest et al. | |
| 2023/0192707 A1 | 6/2023 | Proulx-Lafrance et al. | |

FOREIGN PATENT DOCUMENTS

| | | |
|---|---|---|
| CN | 109893653 A | 6/2019 |
| WO | WO-2008139293 A1 | 11/2008 |
| WO | 2018/226771 A1 | 12/2018 |
| WO | WO-2023114995 A1 | 6/2023 |

OTHER PUBLICATIONS

Scott NJA, Rademaker MT, Charles CJ, Espiner EA, Richards AM. Hemodynamic, Hormonal, and Renal Actions of Phosphodiesterase-9 Inhibition in Experimental Heart Failure. J Am Coll Cardiol. Aug. 20, 2019;74(7):889-901. doi: 10.1016/j.jacc.2019.05.067. PMID: 31416533. (Year: 2019).*

Jones, TM., Pharmaceutical Formulation The Science and Technology of Dosage Forms, Chapter 1: Preformulation Studies, 2018 (Year: 2018).*

Clinical Guide to Cardiovascular Disease, 2016, About this Book, https://link.springer.com/book/10.1007/978-1-4471-7293-2#toc (Year: 2016).*

Friedewald V.E., Clinical Guide to Cardiovascular Disease, 2016, Front Matter (Year: 2016).*

U.S. Appl. No. 12/118,013, filed Sep. 5, 2008.

Verhoest.P., et al., "Design and Discovery of 6-[(3 S ,4 S )-4-Methyl-1-(pyrimidin-2-ylmethyl)pyrrolidin-3-yl]-1-(tetrahydro-2 H-pyran-4-yl)-1,5-dihydro-4 H-pyrazolo[3,4-d]pyrimidin-4-one (PF-04447943), a Selective Brain Penetrant PDE9A Inhibitor for the Treatment of Cognitive Disorders," Journal of Medicinal Chemistry, (2012); 55(21):9045-9054.

Wunder et al. "Characterization of the first potent and selective PDE9 inhibitor using a cGMP reporter cell line." Molecular Pharmacology, (Dec. 1, 2005); 68(6):1775-1781.

Gokhale et al., "API Solid-Form Screening and Selection", in Developing Solid Oral Dosage Forms, Academic Press, (2017), pp. 85-112. doi:10.1016/B978-0-12-802447-8.00004-2.

Liu et al., "Improving the Solubility, Hygroscopicity and Permeability of Enrofloxacin by Forming 1:2 Pharmaceutical Salt Cocrystal with Neutral and Anionic Co-Existing p-Nitrobenzoic Acid", J Drug Deliv Sci Technol, (2022), 76: 103732, 11 pages. doi: 10.1016/j.jddst.2022.103732.

Ng et al., "Formulation Strategies to Improve the Stability and Handling of Oral Solid Dosage Forms of Highly Hygroscopic Pharmaceuticals and Nutraceuticals", Pharmaceutics, (Sep. 22, 2022), 14(10): 2015, 38 pages. doi: 10.3390/pharmaceutics14102015.

Prasad et al., "Characterization, Solubility, and Hygroscopicity of BMS-817399", Org Process Res Dev, (2024), 28 (8): 3119-3127.

Wager et al., "Moving Beyond Rules: The Development of a Central Nervous System Multiparameter Optimization (Cns Mpo) Approach to Enable Alignment of Druglike Properties", ACS Chem Neurosci, (Jun. 16, 2010), 1(6): 435-449. doi: 10.1021/cn100008c. Epub Mar. 25, 2010.

* cited by examiner

*Primary Examiner* — Bruck Kifle
*Assistant Examiner* — Kevin S Martin
(74) *Attorney, Agent, or Firm* — Fenwick & West LLP; Matthew Pavao; Chen Chen

(57) ABSTRACT

The present disclosure provides solid forms of 6-((3S,4S)-4-methyl-1-(pyrimidin-2-ylmethyl)pyrrolidin-3-yl)-1-(tetrahydro-2H-pyran-4-yl)-1,5-dihydro-4H-pyrazolo[3,4-d]pyrimidin-4-one, and methods of preparing and using the same.

19 Claims, 30 Drawing Sheets

SOLID FORMS OF PYRAZOLO[3,4-D]PYRIMIDINE COMPOUNDS

RELATED APPLICATIONS

This application is a continuation of U.S. application Ser. No. 18/082,622, filed on Dec. 16, 2022, which claims priority to and the benefit of U.S. Provisional Application No. 63/290,136, filed on Dec. 16, 2021, the entire contents of each of which are incorporated herein by reference.

BACKGROUND

The phosphodiesterase (PDE) enzyme family hydrolyses cGMP and cAMP. The PDE9 enzyme selectively hydrolyses cGMP over cAMP. PDE9 has been found to be present in a variety of human tissues, namely the testes, brain, small intestine, skeletal muscle, heart, lung, thymus and spleen, as well as in smooth muscle cells within the human vasculature of a variety of tissues.

A variety of physiological processes in the cardiovascular, nervous and immune systems are controlled by the NO/cGMP pathway, including ion channel conductance, glycogenolysis, cellular apoptosis, and smooth muscle relaxation. In blood vessels, relaxation of vascular smooth muscles leads to vasodilation and increased blood flow By reducing or preventing the hydrolysis of cGMP by PDE9, PDE9 inhibitors elevate the intracellular level of cGMP, thus enhancing or prolonging its effects.

Accordingly, there is a need for PDE9 inhibitors that are effective in treating conditions that may be regulated or normalized by inhibition of PDE9. The present disclosure addresses such needs.

SUMMARY

The present disclosure provides solid forms of 6-((3S,4S)-4-methyl-1-(pyrimidin-2-ylmethyl)pyrrolidin-3-yl)-1-(tetrahydro-2H-pyran-4-yl)-1,5-dihydro-4H-pyrazolo[3,4-d]pyrimidin-4-one, and methods of preparing and using the same.

In one aspect, the present disclosure provides Solid Form A of 6-((3S,4S)-4-methyl-1-(pyrimidin-2-ylmethyl)pyrrolidin-3-yl)-1-(tetrahydro-2H-pyran-4-yl)-1,5-dihydro-4H-pyrazolo[3,4-d]pyrimidin-4-one (Compound X) of the following structure:

(X)

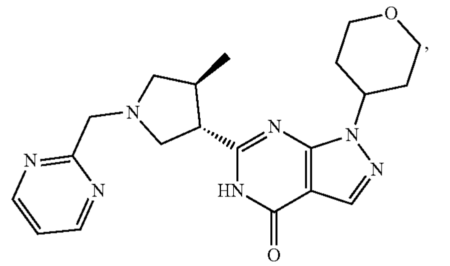

wherein the Solid Form A is characterized by having X-ray powder diffraction peaks at approximately 18.9, 20.4, and 23.1°2θ using Cu Kα radiation.

In another aspect, the present disclosure provides Solid Form B of Compound X, wherein the Solid Form B is characterized by having X-ray powder diffraction peaks at approximately 8.0, 15.0, and 19.3°2θ using Cu Kα radiation.

In yet another aspect, the present disclosure provides Solid Form C of Compound X, wherein the Solid Form C is characterized by having X-ray powder diffraction peaks at approximately 8.6, 8.7, 15.0, and 18.9°2θ using Cu Kα radiation.

In yet another aspect, the present disclosure provides Solid Form D of Compound X, wherein the Solid Form D is characterized by having X-ray powder diffraction peaks at approximately 9.1, 6.8, and 15.5°2θ using Cu Kα radiation.

The present disclosure also provides pharmaceutical compositions comprising the Solid Form A, B, C, or D disclosed herein and pharmaceutically acceptable carriers or excipients.

The present disclosure further provides methods of treating or preventing a disease or disorder, comprising administering to a subject in need thereof the Solid Form A, B, C, or D or pharmaceutical compositions comprising the Solid Form A, B, C, or D disclosed herein.

DETAILED DESCRIPTION

Solid Forms

Figure 1A:
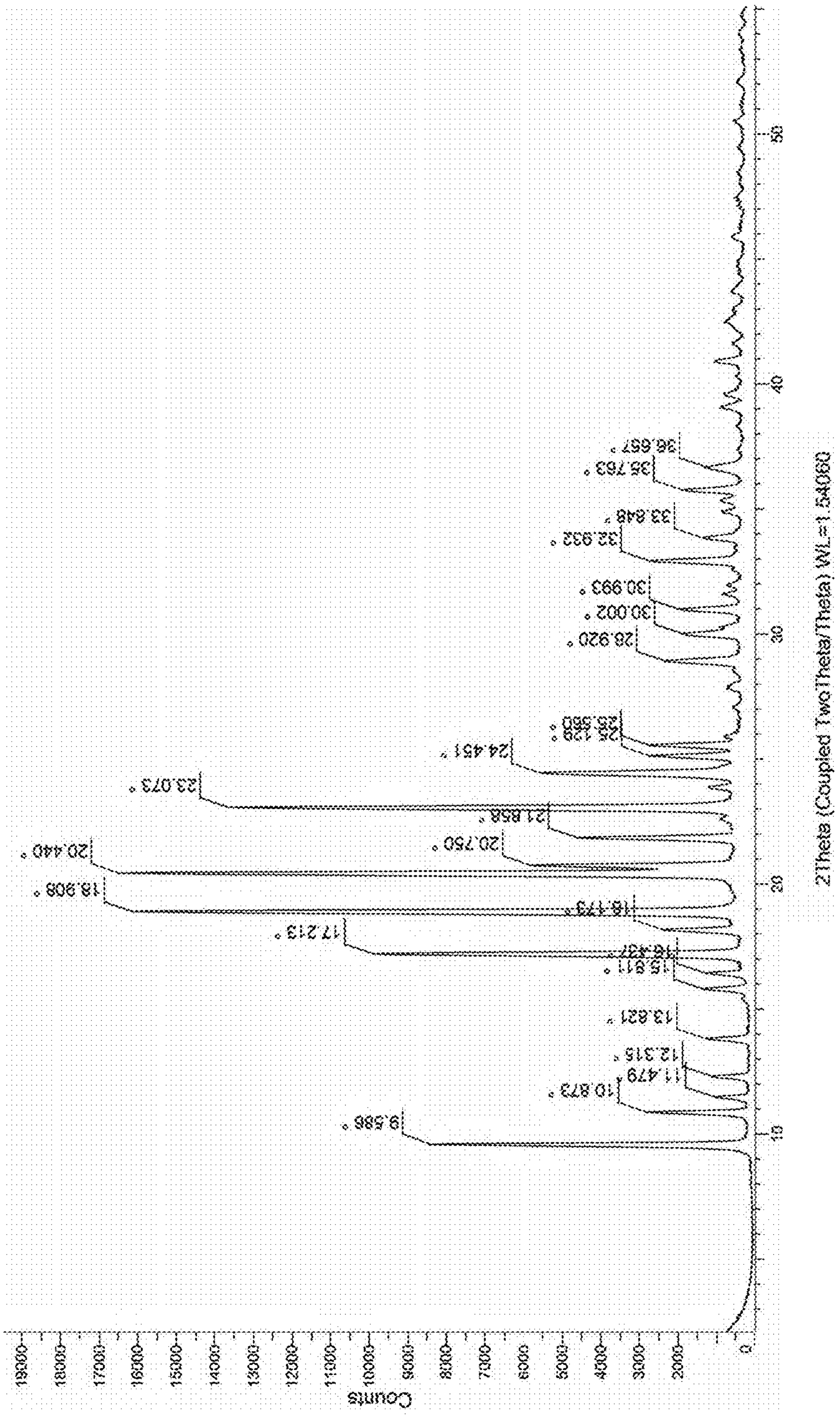
FIG. 1A is a powder X-ray diffractogram (XRPD) of Solid Form A showing the entire range of angle from 0°2θ to 60°2θ.

The present disclosure provides polymorphs of 6-((3S, 4S)-4-methyl-1-(pyrimidin-2-ylmethyl)pyrrolidin-3-yl)-1-(tetrahydro-2H-pyran-4-yl)-1,5-dihydro-4H-pyrazolo[3,4-d]pyrimidin-4-one (Compound X) of the following structure:

(X)

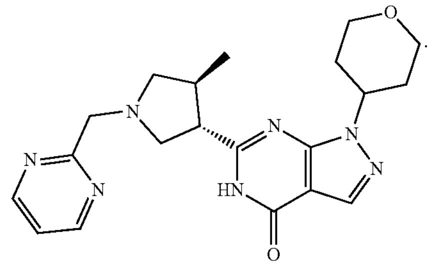

Solid Form a ("Form A")

In one aspect, the present disclosure provides a Solid Form A of Compound X characterized by having X-ray powder diffraction ("XRPD") peaks at approximately 18.9, 20.4, and 23.1°2θ using Cu Kα radiation. In certain embodiments, the Solid Form A is characterized by having XRPD peaks at approximately 9.6, 17.2, 18.9, 20.4, and 23.1°2θ using Cu Kα radiation. In certain embodiments, the Solid Form A is characterized by having XRPD peaks at approximately 9.6, 17.2, 18.9, 20.4, 20.7, 21.9, 23.1, and 24.5°2θ using Cu Kα radiation. In certain embodiments, the Solid Form A is characterized by having XRPD peaks at approximately 9.6, 10.9, 17.2, 18.2, 18.9, 20.4, 20.7, 21.9, 23.1, 24.5, 25.1, 25.6, 28.9, and 32.9°2θ using Cu Kα radiation.

In certain embodiments, "approximately" means that the recited XRPD peak may vary by ±0.2°2θ. In certain embodiments, the Solid Form A of Compound X characterized by having X-ray powder diffraction ("XRPD") peaks at 18.9±0.2, 20.4±0.2, and 23.1±0.2°2θ using Cu Kα radiation. In certain embodiments, the Solid Form A is characterized by having XRPD peaks at 9.6±0.2, 17.2±0.2, 18.9±0.2, 20.4±0.2, and 23.1±0.2°2θ using Cu Kα radiation. In certain embodiments, the Solid Form A is characterized by having XRPD peaks at 9.6±0.2, 17.2±0.2, 18.9±0.2, 20.4±0.2, 20.7±0.2, 21.9±0.2, 23.1±0.2, and 24.5±0.2°2θ using Cu Kα radiation. In certain embodiments, the Solid Form A is characterized by having XRPD peaks at 9.6±0.2, 10.9±0.2, 17.2±0.2, 18.2±0.2, 18.9±0.2, 20.4±0.2, 20.7±0.2, 21.9±0.2, 23.1±0.2, 24.5±0.2, 25.1±0.2, 25.6±0.2, 28.9±0.2, and 32.9±0.2°2θ using Cu Kα radiation.

In certain embodiments, "approximately" means that the recited XRPD peak may vary by ±0.1°2θ. In certain embodiments, the Solid Form A of Compound X characterized by having X-ray powder diffraction ("XRPD") peaks at 18.9±0.1, 20.4±0.1, and 23.1±0.1°2θ using Cu Kα radiation. In certain embodiments, the Solid Form A is characterized by having XRPD peaks at 9.6±0.1, 17.2±0.1, 18.9±0.1, 20.4±0.1, and 23.1±0.1°2θ using Cu Kα radiation. In certain embodiments, the Solid Form A is characterized by having XRPD peaks at 9.6±0.1, 17.2±0.1, 18.9±0.1, 20.4±0.1, 20.7±0.1, 21.9±0.1, 23.1±0.1, and 24.5±0.1°2θ using Cu Kα radiation. In certain embodiments, the Solid Form A is characterized by having XRPD peaks at 9.6±0.1, 10.9±0.1, 17.2±0.1, 18.2±0.1, 18.9±0.1, 20.4±0.1, 20.7±0.1, 21.9±0.1, 23.1±0.1, 24.5±0.1, 25.1±0.1, 25.6±0.1, 28.9±0.1, and 32.9±0.1°2θ using Cu Kα radiation.

In certain embodiments, the Solid Form A is characterized by having XRPD peaks at approximately the positions (in degrees 2-theta or °2-theta) shown in any one of the first through third columns in the table below:

| Angle (°2-theta) | Angle (°2-theta) | Angle (°2-theta) | Relative intensity (%) |
|---|---|---|---|
| 9.6 | 9.6 ± 0.2 | 9.6 ± 0.1 | 51.8 |
| 10.9 | 10.9 ± 0.2 | 10.9 ± 0.1 | 16.4 |
| 11.5 | 11.5 ± 0.2 | 11.5 ± 0.1 | 5.4 |
| 12.3 | 12.3 ± 0.2 | 12.3 ± 0.1 | 6 |
| 13.8 | 13.8 ± 0.2 | 13.8 ± 0.1 | 7.1 |
| 15.8 | 15.8 ± 0.2 | 15.8 ± 0.1 | 7.1 |
| 16.4 | 16.4 ± 0.2 | 16.4 ± 0.1 | 6.3 |
| 17.2 | 17.2 ± 0.2 | 17.2 ± 0.1 | 59.9 |
| 18.2 | 18.2 ± 0.2 | 18.2 ± 0.1 | 12.2 |
| 18.9 | 18.9 ± 0.2 | 18.9 ± 0.1 | 98.3 |
| 20.4 | 20.4 ± 0.2 | 20.4 ± 0.1 | 100 |
| 20.7 | 20.7 ± 0.2 | 20.7 ± 0.1 | 33 |
| 21.9 | 21.9 ± 0.2 | 21.9 ± 0.1 | 25.3 |
| 23.1 | 23.1 ± 0.2 | 23.1 ± 0.1 | 82.1 |
| 24.5 | 24.5 ± 0.2 | 24.5 ± 0.1 | 31.6 |
| 25.1 | 25.1 ± 0.2 | 25.1 ± 0.1 | 14 |
| 25.6 | 25.6 ± 0.2 | 25.6 ± 0.1 | 14.3 |
| 28.9 | 28.9 ± 0.2 | 28.9 ± 0.1 | 12 |
| 30 | 30 ± 0.2 | 30 ± 0.1 | 9.1 |
| 31 | 31 ± 0.2 | 31 ± 0.1 | 9.8 |
| 32.9 | 32.9 ± 0.2 | 32.9 ± 0.1 | 14.6 |
| 33.8 | 33.8 ± 0.2 | 33.8 ± 0.1 | 6 |
| 35.8 | 35.8 ± 0.2 | 35.8 ± 0.1 | 9.3 |
| 36.7 | 36.7 ± 0.2 | 36.7 ± 0.1 | 5.2 |

Note:
the relative intensity provide in column 4 ("Relative intensity (%)") is for reference and is not required as part of characterization of the XRPD peaks.

In certain embodiments, the Solid Form A is characterized by the XPRD peaks as set forth in any one of the embodiments described in paragraphs [0042], [0043] and [0044] above and one or more of the remaining different XPRD peaks selected from those described in the table above (the remaining different peaks are selected from column 1 for embodiments in paragraph [0042], from column 2 for embodiments in paragraph [0043], or from column 3 for embodiments in paragraph [0044], respectively).

In certain embodiments, the Solid Form A is characterized by having XRPD peaks at approximately the positions (in degrees 2-theta or °2-theta) shown in any one of the first through third columns in the table below:

| Angle (°2θ) | Angle (°2θ) | Angle (°2θ) | Rel. Intensity |
|---|---|---|---|
| 9.585853 | 9.585853 ± 0.2 | 9.585853 ± 0.1 | 0.518112 |
| 10.87268 | 10.87268 ± 0.2 | 10.87268 ± 0.1 | 0.16447 |
| 11.47872 | 11.47872 ± 0.2 | 11.47872 ± 0.1 | 0.054495 |
| 12.31546 | 12.31546 ± 0.2 | 12.31546 ± 0.1 | 0.059837 |
| 13.82144 | 13.82144 ± 0.2 | 13.82144 ± 0.1 | 0.070839 |
| 15.39587 | 15.39587 ± 0.2 | 15.39587 ± 0.1 | 0.009013 |
| 15.81057 | 15.81057 ± 0.2 | 15.81057 ± 0.1 | 0.071087 |
| 16.4368 | 16.4368 ± 0.2 | 16.4368 ± 0.1 | 0.063092 |
| 17.21252 | 17.21252 ± 0.2 | 17.21252 ± 0.1 | 0.599466 |
| 18.17312 | 18.17312 ± 0.2 | 18.17312 ± 0.1 | 0.122473 |
| 18.90844 | 18.90844 ± 0.2 | 18.90844 ± 0.1 | 0.983328 |
| 20.4398 | 20.4398 ± 0.2 | 20.4398 ± 0.1 | 1 |
| 20.7497 | 20.7497 ± 0.2 | 20.7497 ± 0.1 | 0.329777 |
| 21.8577 | 21.8577 ± 0.2 | 21.8577 ± 0.1 | 0.253024 |
| 22.62474 | 22.62474 ± 0.2 | 22.62474 ± 0.1 | 0.020469 |
| 23.07301 | 23.07301 ± 0.2 | 23.07301 ± 0.1 | 0.820795 |
| 23.86868 | 23.86868 ± 0.2 | 23.86868 ± 0.1 | 0.041937 |
| 24.45101 | 24.45101 ± 0.2 | 24.45101 ± 0.1 | 0.316004 |
| 25.1292 | 25.1292 ± 0.2 | 25.1292 ± 0.1 | 0.139713 |
| 25.56037 | 25.56037 ± 0.2 | 25.56037 ± 0.1 | 0.142751 |
| 25.91479 | 25.91479 ± 0.2 | 25.91479 ± 0.1 | 0.023046 |
| 27.07006 | 27.07006 ± 0.2 | 27.07006 ± 0.1 | 0.011894 |
| 27.89876 | 27.89876 ± 0.2 | 27.89876 ± 0.1 | 0.02229 |
| 28.56547 | 28.56547 ± 0.2 | 28.56547 ± 0.1 | 0.01067 |
| 28.91968 | 28.91968 ± 0.2 | 28.91968 ± 0.1 | 0.120061 |
| 30.00177 | 30.00177 ± 0.2 | 30.00177 ± 0.1 | 0.090712 |
| 30.29597 | 30.29597 ± 0.2 | 30.29597 ± 0.1 | 0.030314 |
| 30.99291 | 30.99291 ± 0.2 | 30.99291 ± 0.1 | 0.098103 |
| 31.60044 | 31.60044 ± 0.2 | 31.60044 ± 0.1 | 0.027813 |
| 31.95262 | 31.95262 ± 0.2 | 31.95262 ± 0.1 | 0.021351 |
| 32.93155 | 32.93155 ± 0.2 | 32.93155 ± 0.1 | 0.146419 |
| 33.84793 | 33.84793 ± 0.2 | 33.84793 ± 0.1 | 0.059528 |
| 34.89721 | 34.89721 ± 0.2 | 34.89721 ± 0.1 | 0.02884 |
| 35.34829 | 35.34829 ± 0.2 | 35.34829 ± 0.1 | 0.033626 |
| 35.76305 | 35.76305 ± 0.2 | 35.76305 ± 0.1 | 0.092904 |
| 36.65705 | 36.65705 ± 0.2 | 36.65705 ± 0.1 | 0.052422 |
| 37.3939 | 37.3939 ± 0.2 | 37.3939 ± 0.1 | 0.007051 |
| 38.33442 | 38.33442 ± 0.2 | 38.33442 ± 0.1 | 0.008377 |
| 39.1009 | 39.1009 ± 0.2 | 39.1009 ± 0.1 | 0.033081 |
| 39.62588 | 39.62588 ± 0.2 | 39.62588 ± 0.1 | 0.028605 |
| 40.32828 | 40.32828 ± 0.2 | 40.32828 ± 0.1 | 0.00847 |
| 40.9116 | 40.9116 ± 0.2 | 40.9116 ± 0.1 | 0.043316 |
| 41.60553 | 41.60553 ± 0.2 | 41.60553 ± 0.1 | 0.013904 |
| 42.49117 | 42.49117 ± 0.2 | 42.49117 ± 0.1 | 0.028256 |
| 42.98194 | 42.98194 ± 0.2 | 42.98194 ± 0.1 | 0.013539 |
| 43.74369 | 43.74369 ± 0.2 | 43.74369 ± 0.1 | 0.017109 |
| 45.88631 | 45.88631 ± 0.2 | 45.88631 ± 0.1 | 0.019922 |
| 47.47183 | 47.47183 ± 0.2 | 47.47183 ± 0.1 | 0.013344 |
| 49.46794 | 49.46794 ± 0.2 | 49.46794 ± 0.1 | 0.008523 |
| 50.51641 | 50.51641 ± 0.2 | 50.51641 ± 0.1 | 0.014503 |
| 52.10043 | 52.10043 ± 0.2 | 52.10043 ± 0.1 | 0.010835 |
| 54.03993 | 54.03993 ± 0.2 | 54.03993 ± 0.1 | 0.008078 |
| 54.76259 | 54.76259 ± 0.2 | 54.76259 ± 0.1 | 0.005109 |

Note:
the relative intensity provide in column 4 ("Relative intensity (%)") is for reference and is not required as part of characterization of the XRPD peaks.

In certain embodiments, the Solid Form A is characterized by the XPRD peaks as set forth in any one of the embodiments described in paragraphs [0042], [0043] and [0044] above and one or more of the remaining different XPRD peaks selected from those described in the table above (the remaining different peaks are selected from column 1 for embodiments in paragraph [0042], from column 2 for embodiments in paragraph [0043] or, from column 3 for embodiments in paragraph [0044], respectively).

In certain embodiments, the Solid Form A is characterized by an XRPD pattern substantially the same as that set forth in FIG. 1A.

Figure 2:
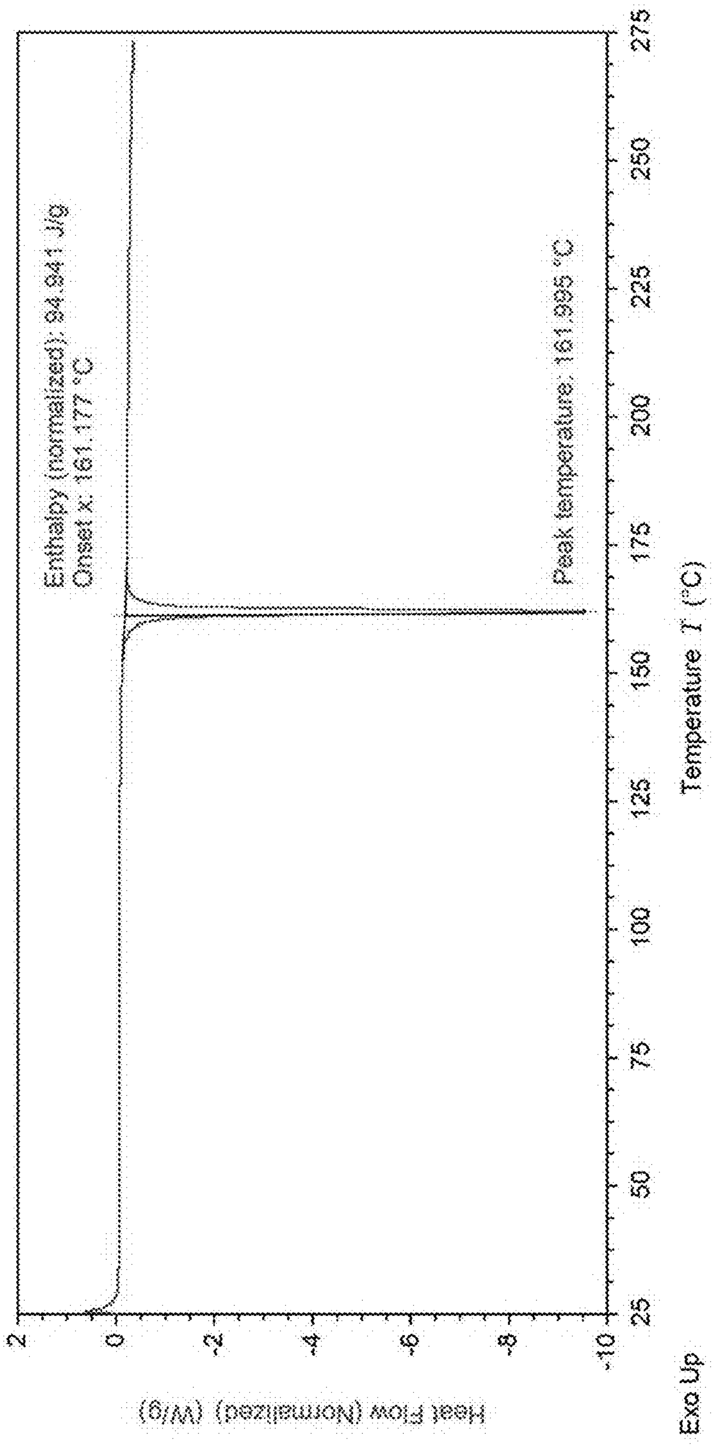
FIG. 2 is a differential scanning calorimetry (DSC) thermogram of Solid Form A.

In certain embodiments, the Solid Form A is characterized by an endothermic event with onset between approximately 155 °C and approximately 168 °C as measured DSC. In certain embodiments, the Solid Form A is characterized by an endothermic event with peak temperature at approximately 162 °C as measured by DSC. In certain embodiments, "approximately" means that the variability of the temperature is within ±2 °C. In certain embodiments, the Solid Form A is characterized by an endothermic event with onset between 155±2 °C and 168±2 °C as measured DSC. In certain embodiments, the Solid Form A is characterized by an endothermic event with peak temperature at 162±2 °C as measured by DSC. In certain embodiments, "approximately" means that the variability of the temperature is within ±1 °C. In certain embodiments, the Solid Form A is characterized by an endothermic event with onset between 155±1 °C and 168±1 °C as measured DSC. In certain embodiments, the Solid Form A is characterized by an endothermic event with peak temperature at 162±1 °C as measured by DSC. In certain embodiments, the Solid Form A is characterized by a DSC thermogram substantially the same as that set forth in FIG. 2.

In certain embodiments, the Solid Form A shows a weight loss of between approximately 0.05% and approximately 0.3% between approximately 150 °C and approximately 225 °C as measured by TGA. In certain embodiments, the Solid Form A shows a weight loss of approximately 0.11% between approximately 150 °C and approximately 225 °C as measured by TGA. In certain embodiments, "approximately" means that the variability of the temperature is within ±2 °C. In certain embodiments, the Solid Form A shows a weight loss of between approximately 0.05% and approximately 0.3% between 150±2 °C and 225±2 °C as measured by TGA. In certain embodiments, the Solid Form A shows a weight loss of approximately 0.11% between 150±2 °C and 225±2 °C as measured by TGA. In certain embodiments, "approximately" means that the variability of the temperature is within ±1 °C. In certain embodiments, the Solid Form A shows a weight loss of between approximately 0.05% and approximately 0.3% between 150±1 °C and 225±1 °C as measured by TGA. In certain embodiments, the Solid Form A shows a weight loss of approximately 0.11% between 150±1 °C and 225±1 °C as measured by TGA.

The Solid Form A is non-hygroscopic. In certain embodiments, the Solid Form A displays non-hygroscopicity between 0% and 90% relative humidity (RH) at approximately 25 °C (e.g., less than 0.2% w/w water uptake). In certain embodiments, the Solid Form A displays non-hygroscopicity between 0% and 70% relative humidity (RH) at approximately 25 °C (e.g., less than 0.2% w/w water uptake).

The Solid Form A is stable. In certain embodiments, the Solid Form A is stable (e.g., no decrease in HPLC area % purity or change in polymorphic form) under various storage conditions. In certain embodiments, the Solid Form A is stable (e.g., no decrease in HPLC area % purity or change in polymorphic form) between approximately 20 °C and approximately 90 °C (e.g., 22 °C, 25 °C, 40 °C, 50 °C, 60 °C, 70° C., or 80 °C) for at least one week, preferably at least two weeks, preferably at least three weeks, preferably at least one month, preferably at least two months, preferably at least three months, preferably at least four months, preferably at least six months, preferably at least one year, preferably at least two years, preferably at least three years, preferably at least four years, preferably at least five years.

In certain embodiments, the Solid Form A is stable (e.g., no decrease in HPLC area % purity or change in polymorphic form) between approximately 20% relative humidity (RH) and approximately 98% relative humidity (RH) (e.g., 40% RH, 60% RH, 75% RH, or 96% RH) for at least one week, preferably at least two weeks, preferably at least three weeks, preferably at least one month, preferably at least two months, preferably at least three months, preferably at least four months, preferably at least six months, preferably at least one year, preferably at least two years, preferably at least three years, preferably at least four years, preferably at least five years.

In certain embodiments, the Solid Form A is stable (e.g., no decrease in HPLC area % purity or change in polymorphic form) under 40 °C/75% relative humidity (RH) for at least one week, preferably at least two weeks, preferably at least three weeks, preferably at least one month, preferably at least two months, preferably at least three months, preferably at least four months, preferably at least six months, preferably at least one year, preferably at least two years, preferably at least three years, preferably at least four years, preferably at least five years.

The Solid Form A is not a hydrate. The Solid Form A is not a solvate.

The Solid Form A is an anhydrous solid form.

The Solid Form A is a non-hygroscopic solid form.

The Solid Form A is an anhydrous and non-hygroscopic solid form.

The Solid Form A is an anhydrous, ansolvate and non-hygroscopic solid form.

In certain embodiments, the Solid Form A is prepared by slurrying an amorphous form of Compound X in a solvent. In certain embodiments, the Solid Form A is prepared by slurrying an amorphous form of Compound X in a solvent selected from tetrahydrofuran, ethyl acetate, isopropyl alcohol, toluene, heptane, water, 1-butanol, 1,2-xylene, acetone, and ethanol, and any combination thereof. In certain embodiments, the Solid Form A is prepared by slurrying an amorphous form of Compound X in a solvent selected from tetrahydrofuran, ethyl acetate, isopropyl alcohol, heptane, 1,2-xylene, acetone, and ethanol, and any combination thereof. In certain embodiments, the slurrying is conducted at approximately 20 °C. In certain embodiments, the slurrying is conducted at approximately 25 °C. In certain embodiments, the slurrying is conducted at approximately 40 °C. In certain embodiments, the slurrying is conducted with continuous agitation.

In certain embodiments, the Solid Form A is prepared by a method comprising: combining an amorphous form of Compound X with a solvent to form a mixture; heating the mixture to form a solution, and cooling the solution; and optionally isolating Solid Form A. In certain embodiments, the solvent is tetrahydrofuran, ethyl acetate, isopropyl alcohol, toluene, heptane, water, 1-butanol, 1,2-xylene, acetone, and ethanol, and any combination thereof. In certain embodiments, the solvent is tetrahydrofuran, ethyl acetate, isopropyl alcohol, heptane, 1,2-xylene, acetone, and ethanol, and any combination thereof. In certain embodiments, the solvent is tetrahydrofuran. In certain embodiments, the solution is heated to a temperature of about 30 °C. In certain embodiments, the solution is heated to a temperature of about 35 °C. In certain embodiments, the solution is heated to a temperature of about 40 °C. In certain embodiments, the solution is heated to a temperature of about 45 °C. In certain embodiments, the solution is heated to a temperature of about 50 °C. In certain embodiments, the solution is heated to a temperature of greater than 30 °C. In certain embodiments, the solution is heated to a temperature of greater than 40 °C. In certain embodiments, the solution is heated to a temperature of greater than 50 °C. In certain embodiments, the solution is cooled to a temperature of about or below 25 °C. In certain embodiments, the solution is cooled to a temperature of about or below 20 °C. In certain embodiments, the solution is cooled to a temperature of about or below 15 °C. In certain embodiments, the cooling comprises multiple steps of cooling. In certain embodiments, the cooling comprises cooling to a first temperature, followed by cooling to a second temperature.

Solid Form B ("Form B")

In another aspect, the present disclosure provides a Solid Form B of Compound X characterized by having X-ray powder diffraction ("XRPD") peaks at approximately 8.0, 15.0, and 19.3°2θ using Cu Kα radiation. In certain embodiments, the Solid Form B is characterized by having XRPD peaks at approximately 8.0, 15.0, 19.3, 25.6, and 26.9°2θ using Cu Kα radiation. In certain embodiments, the Solid Form B is characterized by having XRPD peaks at approximately 8.0, 15.0, 16.2, 19.3, 19.6, 25.6, and 26.9°2θ using Cu Kα radiation. In certain embodiments, the Solid Form B is characterized by having XRPD peaks at approximately 8.0, 14.5, 15.0, 16.2, 19.3, 19.6, 25.3, 25.6, 26.9, 28.8, 28.9, and 29.2°2θ using Cu Kα radiation.

In certain embodiments, "approximately" means that the recited XRPD peak may vary by ±0.2°2θ. In certain embodiments, the Solid Form B is characterized by having XRPD peaks at approximately 8.0±0.2, 15.0±0.2, and 19.3±0.2°2θ using Cu Kα radiation. In certain embodiments, the Solid Form B is characterized by having XRPD peaks at approximately 8.0±0.2, 15.0±0.2, 19.3±0.2, 25.6±0.2, and 26.9±0.2°2θ using Cu Kα radiation. In certain embodiments, the Solid Form B is characterized by having XRPD peaks at approximately 8.0±0.2, 15.0±0.2, 16.2±0.2, 19.3±0.2, 19.6±0.2, 25.6±0.2, and 26.9±0.2°2θ using Cu Kα radiation. In certain embodiments, the Solid Form B is characterized by having XRPD peaks at approximately 8.0±0.2, 14.5±0.2, 15.0±0.2, 16.2±0.2, 19.3±0.2, 19.6±0.2, 25.3±0.2, 25.6±0.2, 26.9±0.2, 28.8±0.2, 28.9±0.2, and 29.2±0.2°2θ using Cu Kα radiation.

In certain embodiments, "approximately" means that the recited XRPD peak may vary by ±0.1°2θ. In certain embodiments, the Solid Form B is characterized by having XRPD peaks at approximately 8.0±0.1, 15.0±0.1, and 19.3±0.1°2θ using Cu Kα radiation. In certain embodiments, the Solid Form B is characterized by having XRPD peaks at approximately 8.0±0.1, 15.0±0.1, 19.3±0.1, 25.6±0.1, and 26.9±0.1°2θ using Cu Kα radiation. In certain embodiments, the Solid Form B is characterized by having XRPD peaks at approximately 8.0±0.1, 15.0±0.1, 16.2±0.1, 19.3±0.1, 19.6±0.1, 25.6±0.1, and 26.9±0.1°2θ using Cu Kα radiation. In certain embodiments, the Solid Form B is characterized by having XRPD peaks at approximately 8.0±0.1, 14.5±0.1, 15.0±0.1, 16.2±0.1, 19.3±0.1, 19.6±0.1, 25.3±0.1, 25.6±0.1, 26.9±0.1, 28.8±0.1, 28.9±0.1, and 29.2±0.1°2θ using Cu Kα radiation.

In certain embodiments, the Solid Form B is characterized by having XRPD peaks at approximately the positions (in degrees 2-theta or °2-theta) shown in any one of the second through fourth columns in the table below:

| No. | Pos. [°2θ] | Pos. [°2θ] | Pos. [°2θ] |
|---|---|---|---|
| 2 | 7.9617 | 7.9617 ± 0.2 | 7.9617 ± 0.1 |
| 4 | 14.4830 | 14.4830 ± 0.2 | 14.4830 ± 0.1 |
| 6 | 15.0352 | 15.0352 ± 0.2 | 15.0352 ± 0.1 |
| 7 | 16.1972 | 16.1972 ± 0.2 | 16.1972 ± 0.1 |
| 9 | 19.3304 | 19.3304 ± 0.2 | 19.3304 ± 0.1 |
| 10 | 19.6443 | 19.6443 ± 0.2 | 19.6443 ± 0.1 |
| 18 | 25.3319 | 25.3319 ± 0.2 | 25.3319 ± 0.1 |
| 19 | 25.6353 | 25.6353 ± 0.2 | 25.6353 ± 0.1 |
| 23 | 26.8902 | 26.8902 ± 0.2 | 26.8902 ± 0.1 |
| 27 | 28.8367 | 28.8367 ± 0.2 | 28.8367 ± 0.1 |

-continued

| No. | Pos. [°2θ] | Pos. [°2θ] | Pos. [°2θ] |
|---|---|---|---|
| 28 | 28.8991 | 28.8991 ± 0.2 | 28.8991 ± 0.1 |
| 29 | 29.2181 | 29.2181 ± 0.2 | 29.2181 ± 0.1 |

In certain embodiments, the Solid Form B is characterized by the XPRD peaks as set forth in any one of the embodiments described in paragraphs [0063], [0064] and [0065] above and one or more of the remaining different XPRD peaks selected from those described in the table immediately above (the remaining different peaks are selected from column 2 for embodiments in paragraph [0063], from column 3 for embodiments in paragraph [0064], or from column 4 for in paragraph [0065], respectively).

In certain embodiments, the Solid Form B is characterized by having XRPD peaks at approximately the positions (in degrees 2-theta or °2-theta) shown in any one of the second through fourth columns in the table below:

| No. | Pos. [°2θ] | Pos. [°2θ] | Pos. [°2θ] |
|---|---|---|---|
| 2 | 8.0 | 8.0 ± 0.2 | 8.0 ± 0.1 |
| 4 | 14.5 | 14.5 ± 0.2 | 14.5 ± 0.1 |
| 6 | 15.0 | 15.0 ± 0.2 | 15.0 ± 0.1 |
| 7 | 16.2 | 16.2 ± 0.2 | 16.2 ± 0.1 |
| 9 | 19.3 | 19.3 ± 0.2 | 19.3 ± 0.1 |
| 10 | 19.6 | 19.6 ± 0.2 | 19.6 ± 0.1 |
| 18 | 25.3 | 25.3 ± 0.2 | 25.3 ± 0.1 |
| 19 | 25.6 | 25.6 ± 0.2 | 25.6 ± 0.1 |
| 23 | 26.9 | 26.9 ± 0.2 | 26.9 ± 0.1 |
| 27 | 28.8 | 28.8 ± 0.2 | 28.8 ± 0.1 |
| 28 | 28.9 | 28.9 ± 0.2 | 28.9 ± 0.1 |
| 29 | 29.2 ± 0.2 | 29.2 ± 0.2 | 29.2 ± 0.1 |

In certain embodiments, the Solid Form B is characterized by the XPRD peaks as set forth in any one of the embodiments described in paragraphs [0063], [0064] and [0065] above and one or more of the remaining different XPRD peaks selected from those described in the table immediately above (the remaining different peaks are selected from column 2 for embodiments in paragraph [0063], from column 3 for embodiments in paragraph [0064], or from column 4 for in paragraph [0065], respectively).

In certain embodiments, the Solid Form B is characterized by having XRPD peaks at approximately the positions (in degrees 2-theta or °2-theta) shown in any one of the second through fourth columns in the table below:

| No. | Pos. [°2θ] | Pos. [°2θ] | Pos. [°2θ] |
|---|---|---|---|
| 1 | 7.2224 | 7.2224 ± 0.2 | 7.2224 ± 0.1 |
| 2 | 7.9617 | 7.9617 ± 0.2 | 7.9617 ± 0.1 |
| 3 | 12.9094 | 12.9094 ± 0.2 | 12.9094 ± 0.1 |
| 4 | 14.4830 | 14.4830 ± 0.2 | 14.4830 ± 0.1 |
| 5 | 14.6445 | 14.6445 ± 0.2 | 14.6445 ± 0.1 |
| 6 | 15.0352 | 15.0352 ± 0.2 | 15.0352 ± 0.1 |
| 7 | 16.1972 | 16.1972 ± 0.2 | 16.1972 ± 0.1 |
| 8 | 18.3297 | 18.3297 ± 0.2 | 18.3297 ± 0.1 |
| 9 | 19.3304 | 19.3304 ± 0.2 | 19.3304 ± 0.1 |
| 10 | 19.6443 | 19.6443 ± 0.2 | 19.6443 ± 0.1 |
| 11 | 20.4537 | 20.4537 ± 0.2 | 20.4537 ± 0.1 |
| 12 | 20.6760 | 20.6760 ± 0.2 | 20.6760 ± 0.1 |
| 13 | 21.8332 | 21.8332 ± 0.2 | 21.8332 ± 0.1 |
| 14 | 23.2910 | 23.2910 ± 0.2 | 23.2910 ± 0.1 |
| 15 | 23.4817 | 23.4817 ± 0.2 | 23.4817 ± 0.1 |
| 16 | 24.0724 | 24.0724 ± 0.2 | 24.0724 ± 0.1 |
| 17 | 24.3417 | 24.3417 ± 0.2 | 24.3417 ± 0.1 |
| 18 | 25.3319 | 25.3319 ± 0.2 | 25.3319 ± 0.1 |

-continued

| No. | Pos. [°2θ] | Pos. [°2θ] | Pos. [°2θ] |
|---|---|---|---|
| 19 | 25.6353 | 25.6353 ± 0.2 | 25.6353 ± 0.1 |
| 20 | 26.0027 | 26.0027 ± 0.2 | 26.0027 ± 0.1 |
| 21 | 26.4025 | 26.4025 ± 0.2 | 26.4025 ± 0.1 |
| 22 | 26.6586 | 26.6586 ± 0.2 | 26.6586 ± 0.1 |
| 23 | 26.8902 | 26.8902 ± 0.2 | 26.8902 ± 0.1 |
| 24 | 27.3465 | 27.3465 ± 0.2 | 27.3465 ± 0.1 |
| 25 | 27.6420 | 27.6420 ± 0.2 | 27.6420 ± 0.1 |
| 26 | 28.0770 | 28.0770 ± 0.2 | 28.0770 ± 0.1 |
| 27 | 28.8367 | 28.8367 ± 0.2 | 28.8367 ± 0.1 |
| 28 | 28.8991 | 28.8991 ± 0.2 | 28.8991 ± 0.1 |
| 29 | 29.2181 | 29.2181 ± 0.2 | 29.2181 ± 0.1 |
| 30 | 29.5288 | 29.5288 ± 0.2 | 29.5288 ± 0.1 |
| 31 | 29.7824 | 29.7824 ± 0.2 | 29.7824 ± 0.1 |
| 32 | 30.3801 | 30.3801 ± 0.2 | 30.3801 ± 0.1 |
| 33 | 30.9764 | 30.9764 ± 0.2 | 30.9764 ± 0.1 |
| 34 | 31.9562 | 31.9562 ± 0.2 | 31.9562 ± 0.1 |
| 35 | 32.4439 | 32.4439 ± 0.2 | 32.4439 ± 0.1 |
| 36 | 32.9341 | 32.9341 ± 0.2 | 32.9341 ± 0.1 |
| 37 | 33.9212 | 33.9212 ± 0.2 | 33.9212 ± 0.1 |

In certain embodiments, the Solid Form B is characterized by the XPRD peaks as set forth in any one of the embodiments described in paragraphs [0063], [0064] and [0065] above and one or more of the remaining different XPRD peaks selected from those described in the table immediately above (the remaining different peaks are selected from column 2 for embodiments in paragraph [0063], from column 3 for embodiments in paragraph [0064], or from column 4 for in paragraph [0065], respectively).

Figure 12:
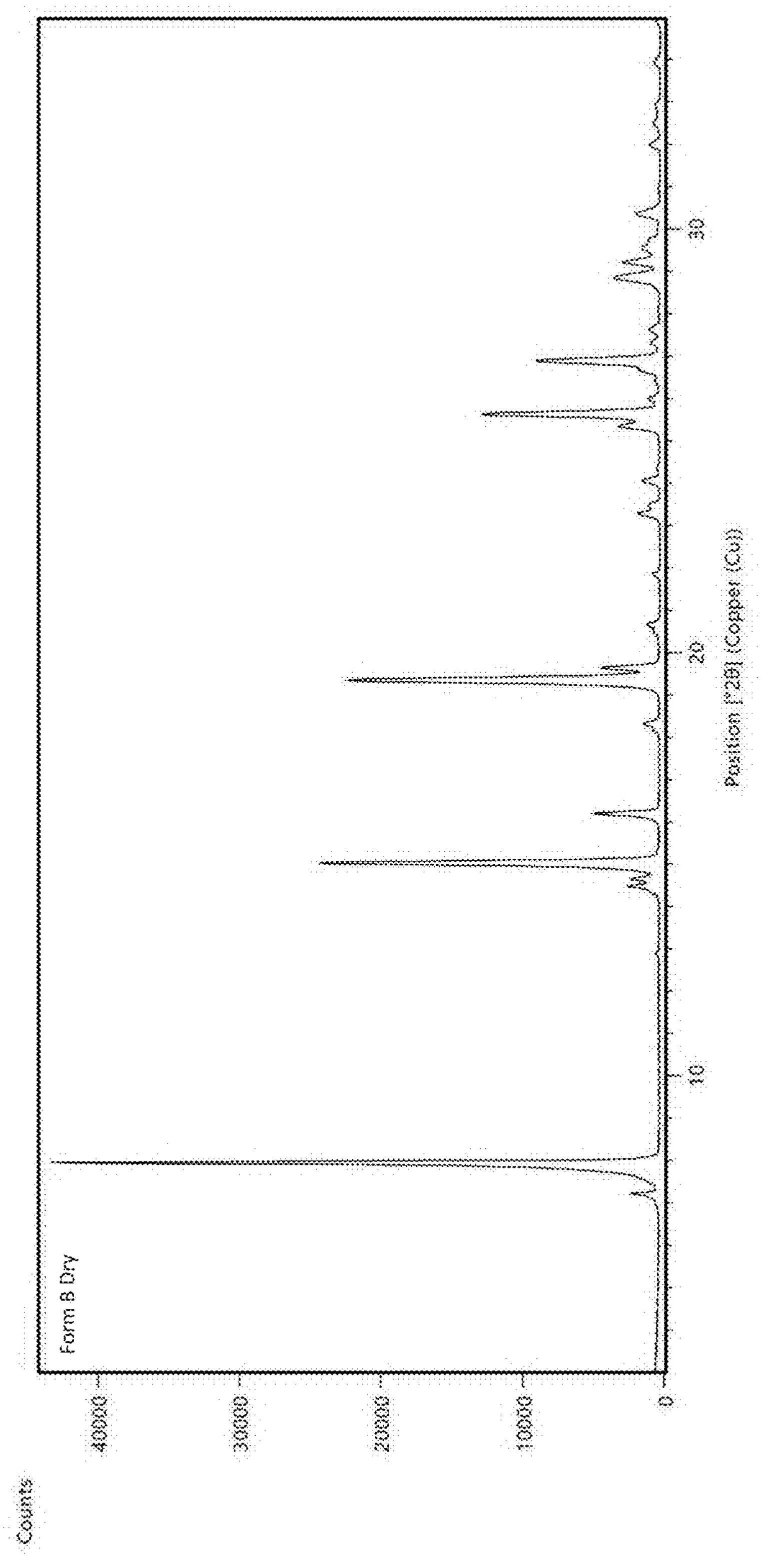
FIG. 12 is an XRPD of Solid Form B showing the range of angle from 0°2θ to 35°2θ.

In certain embodiments, the Solid Form B is characterized by an XRPD pattern substantially the same as that set forth in FIG. 12.

In certain embodiments, the Solid Form B is characterized by three endothermic events with onset at approximately 39 °C and peak temperature at approximately 85 °C; onset at approximately 127 °C and peak temperature at approximately 131 °C; and/or onset at approximately 162 °C and peak temperature at approximately 163 °C, as measured by DSC. In certain embodiments, the Solid Form B is characterized by an endothermic event with onset at approximately 39 °C and peak temperature at approximately 85 °C as measured by DSC. In certain embodiments, the Solid Form B is characterized by an endothermic event with onset at approximately 127 °C and peak temperature at approximately 131 °C as measured by DSC. In certain embodiments, the Solid Form B is characterized by an endothermic event with onset at approximately 162 °C and peak temperature at approximately 163 °C as measured by DSC.

In certain embodiments, "approximately" means that the variability of the temperature is within ±2 °C. In certain embodiments, the Solid Form B is characterized by three endothermic events with onset at approximately 39±2 °C and peak temperature at approximately 85±2 °C; onset at approximately 127±2 °C and peak temperature at approximately 131±2 °C; and/or onset at approximately 162±2 °C and peak temperature at approximately 163±2 °C, as measured by DSC. In certain embodiments, the Solid Form B is characterized by an endothermic event with onset at approximately 39±2 °C and peak temperature at approximately 85±2 °C as measured by DSC. In certain embodiments, the Solid Form B is characterized by an endothermic event with onset at approximately 127±2 °C and peak temperature at approximately 131±2 °C as measured by DSC. In certain embodiments, the Solid Form B is characterized by an endothermic event with onset at approximately 162±2 °C and peak temperature at approximately 163±2 °C as measured by DSC.

In certain embodiments, "approximately" means that the variability of the temperature is within ±1 °C. In certain embodiments, the Solid Form B is characterized by three endothermic events with onset at approximately 39±1 °C and peak temperature at approximately 85±1 °C; onset at approximately 127±1 °C and peak temperature at approximately 131±1 °C; and/or onset at approximately 162±1 °C and peak temperature at approximately 163±1 °C, as measured by DSC. In certain embodiments, the Solid Form B is characterized by an endothermic event with onset at approximately 39±1 °C and peak temperature at approximately 85±1 °C as measured by DSC. In certain embodiments, the Solid Form B is characterized by an endothermic event with onset at approximately 127±1 °C and peak temperature at approximately 131±1 °C as measured by DSC. In certain embodiments, the Solid Form B is characterized by an endothermic event with onset at approximately 162±1 °C and peak temperature at approximately 163±1 °C as measured by DSC.

Figure 19:
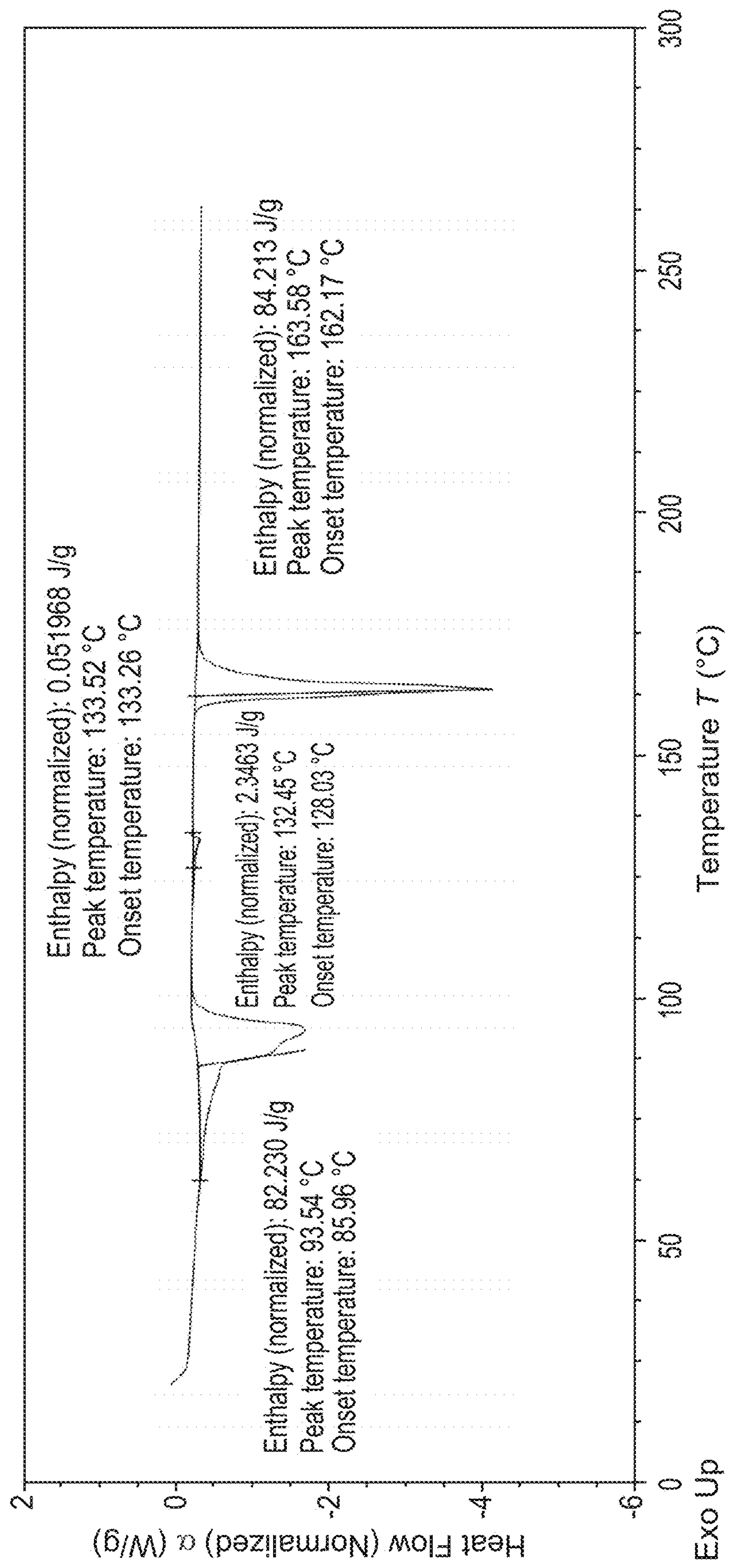
FIG. 19 is a DSC thermogram of Solid Form B.
Figure 20:
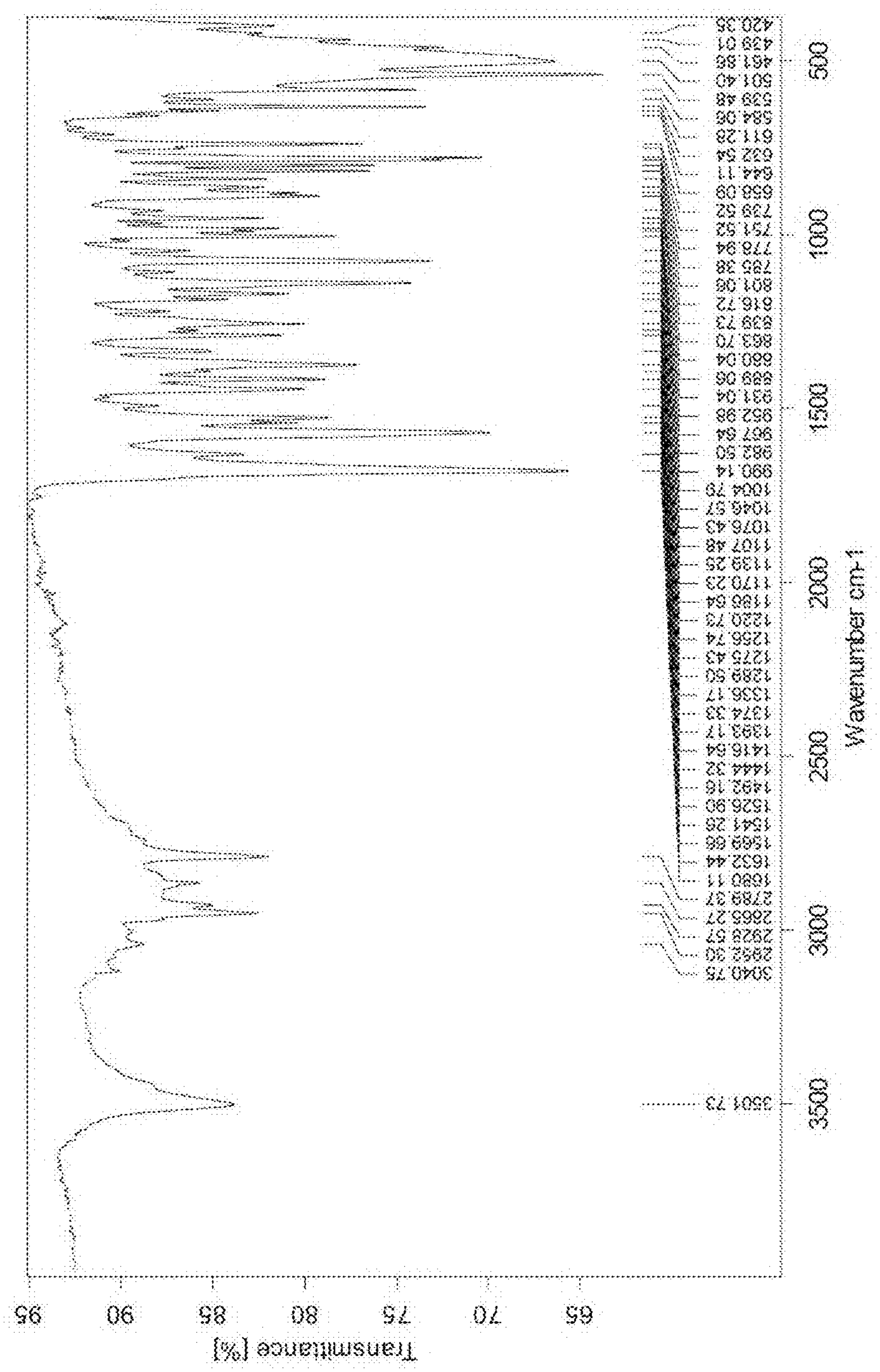
FIG. 20 is a Fourier Transform infrared spectrum of Solid Form B.

In certain embodiments, the Solid Form B is characterized by a DSC thermogram substantially the same as that set forth in FIG. 19.

In certain embodiments, the Solid Form B shows a weight loss of between approximately 3% and approximately 5% between approximately 25 °C and approximately 100 °C as measured by TGA. In certain embodiments, the Solid Form B shows a weight loss of between approximately 3.5% and approximately 4.5% between approximately 25 °C and approximately 100 °C as measured by TGA. In certain embodiments, the Solid Form B shows a weight loss of approximately 4% between approximately 25 °C and approximately 100 °C as measured by TGA.

In certain embodiments, "approximately" means that the variability of the weight loss percentage is within ±0.3%; and the variability of the temperature is within ±3 °C. In certain embodiments, the Solid Form B shows a weight loss of between approximately 3±0.3% and approximately 5±0.3% between approximately 25±3 °C and approximately 100±3 °C as measured by TGA. In certain embodiments, the Solid Form B shows a weight loss of between approximately 3.5±0.3% and approximately 4.5±0.3% between approximately 25±3 °C and approximately 100±3 °C as measured by TGA. In certain embodiments, the Solid Form B shows a weight loss of approximately 4±0.3% between approximately 25±3 °C and approximately 100±3 °C as measured by TGA.

In certain embodiments, the Solid Form B is a solvate. In certain embodiments, Solid Form B is a hydrate.

In certain embodiments, the Solid Form B is prepared by slurrying an amorphous form of Compound X in a solvent comprising water. In certain embodiments, the Solid Form B is prepared by slurrying an amorphous form of Compound X in water. In certain embodiments, the slurrying is conducted at approximately 20 °C. In certain embodiments, the slurrying is conducted at approximately 25 °C. In certain embodiments, the slurrying is conducted at approximately 40 °C. In certain embodiments, the slurrying is conducted with continuous agitation.

In certain embodiments, the Solid Form B is prepared by a method comprising: combining an amorphous form of Compound X with a solvent comprising water to form a mixture; heating the mixture to form a solution, and cooling the solution; and optionally isolating Solid Form B. In certain embodiments, the solvent is water. In certain embodiments, the solution is heated to a temperature of approximately 30 °C. In certain embodiments, the solution is heated to a temperature of approximately 35 °C. In certain embodiments, the solution is heated to a temperature of approximately 40 °C. In certain embodiments, the solution is heated to a temperature of approximately 45 °C. In certain embodiments, the solution is heated to a temperature of approximately 50 °C. In certain embodiments, the solution is heated to a temperature of greater than 30 °C. In certain embodiments, the solution is heated to a temperature of greater than 40 °C. In certain embodiments, the solution is heated to a temperature of greater than 50 °C. In certain embodiments, the solution is cooled to a temperature of approximately or below 25 °C. In certain embodiments, the solution is cooled to a temperature of approximately or below 20 °C. In certain embodiments, the solution is cooled to a temperature of approximately or below 15 °C. In certain embodiments, the cooling comprises multiple steps of cooling. In certain embodiments, the cooling comprises cooling to a first temperature, followed by cooling to a second temperature.

Solid Form ((“Form (”)

In yet another aspect, the present disclosure provides a Solid Form C of Compound X characterized by having X-ray powder diffraction ("XRPD") peaks at approximately 8.6, 8.7, 15.0, 18.9, and 24.7°2θ using Cu Kα radiation. In certain embodiments, the Solid Form C is characterized by having XRPD peaks at approximately 8.6, 8.7, 15.0, 18.9, 19.6, 19.7, 24.7, and 26.2°2θ using Cu Kα radiation. In certain embodiments, the Solid Form C is characterized by having XRPD peaks at approximately 8.6, 8.7, 15.0, 17.2, 18.9, 19.6, 19.7, 21.3, 23.6, 24.7, 26.2, 26.6, 28.1, 28.8, and 30.3°2θ using Cu Kα radiation.

In certain embodiments, "approximately" means that the recited XRPD peak may vary by ±0.2°2θ. In certain embodiments, the Solid Form C is characterized by having XRPD peaks at approximately 8.6±0.2, 8.7±0.2, 15.0±0.2, 18.9±0.2, and 24.7±0.2°2θ using Cu Kα radiation. In certain embodiments, the Solid Form C is characterized by having XRPD peaks at approximately 8.6±0.2, 8.7±0.2, 15.0±0.2, 18.9±0.2, 19.6±0.2, 19.7±0.2, 24.7±0.2, and 26.2±0.2°2θ using Cu Kα radiation. In certain embodiments, the Solid Form C is characterized by having XRPD peaks at approximately 8.6±0.2, 8.7±0.2, 15.0±0.2, 17.2±0.2, 18.9±0.2, 19.6±0.2, 19.7±0.2, 21.3±0.2, 23.6±0.2, 24.7±0.2, 26.2±0.2, 26.6±0.2, 28.1±0.2, 28.8±0.2, and 30.3±0.2°2θ using Cu Kα radiation.

In certain embodiments, "approximately" means that the recited XRPD peak may vary by ±0.1°2θ. In certain embodiments, the Solid Form C is characterized by having XRPD peaks at approximately 8.6±0.1, 8.7±0.1, 15.0±0.1, 18.9±0.1, and 24.7±0.1°2θ using Cu Kα radiation. In certain embodiments, the Solid Form C is characterized by having XRPD peaks at approximately 8.6±0.1, 8.7±0.1, 15.0±0.1, 18.9±0.1, 19.6±0.1, 19.7±0.1, 24.7±0.1, and 26.2±0.1°2θ using Cu Kα radiation. In certain embodiments, the Solid Form C is characterized by having XRPD peaks at approximately 8.6±0.1, 8.7±0.1, 15.0±0.1, 17.2±0.1, 18.9±0.1, 19.6±0.1, 19.7±0.1, 21.3±0.1, 23.6±0.1, 24.7±0.1, 26.2±0.1, 26.6±0.1, 28.1±0.1, 28.8±0.1, and 30.3±0.1°2θ using Cu Kα radiation.

In certain embodiments, the Solid Form C is characterized by having XRPD peaks at approximately the positions (in degrees 2-theta or °2-theta) shown in any one of the second through four columns in the table below:

| No. | Pos. [°2θ] | Pos. [°2θ] | Pos. [°2θ] |
|---|---|---|---|
| 2 | 8.6307 | 8.6307 ± 0.2 | 8.6307 ± 0.1 |
| 3 | 8.6800 | 8.6800 ± 0.2 | 8.6800 ± 0.1 |

-continued

| No. | Pos. [°2θ] | Pos. [°2θ] | Pos. [°2θ] |
|---|---|---|---|
| 8 | 15.0544 | 15.0544 ± 0.2 | 15.0544 ± 0.1 |
| 10 | 17.2160 | 17.2160 ± 0.2 | 17.2160 ± 0.1 |
| 12 | 18.8879 | 18.8879 ± 0.2 | 18.8879 ± 0.1 |
| 13 | 19.6118 | 19.6118 ± 0.2 | 19.6118 ± 0.1 |
| 14 | 19.6608 | 19.6608 ± 0.2 | 19.6608 ± 0.1 |
| 16 | 21.3028 | 21.3028 ± 0.2 | 21.3028 ± 0.1 |
| 18 | 23.5960 | 23.5960 ± 0.2 | 23.5960 ± 0.1 |
| 19 | 24.6607 | 24.6607 ± 0.2 | 24.6607 ± 0.1 |
| 21 | 26.1792 | 26.1792 ± 0.2 | 26.1792 ± 0.1 |
| 22 | 26.6081 | 26.6081 ± 0.2 | 26.6081 ± 0.1 |
| 25 | 28.1084 | 28.1084 ± 0.2 | 28.1084 ± 0.1 |
| 26 | 28.8196 | 28.8196 ± 0.2 | 28.8196 ± 0.1 |
| 28 | 30.3217 | 30.3217 ± 0.2 | 30.3217 ± 0.1 |

In certain embodiments, the Solid Form C is characterized by the XPRD peaks as set forth in any one of the embodiments described in paragraphs [0082], [0083] and [0084] above and one or more of the remaining different XPRD peaks selected from those described in the table immediately above (the remaining different peaks are selected from column 2 for embodiments in paragraph [0082], from column 3 for embodiments in paragraph [0083], or from column 4 for in paragraph [0084], respectively).

In certain embodiments, the Solid Form C is characterized by having XRPD peaks at approximately the positions (in degrees 2-theta or °2-theta) shown in any one of the second through four columns in the table below:

| No. | Pos. [°2θ] | Pos. [°2θ] | Pos. [°2θ] |
|---|---|---|---|
| 2 | 8.6 | 8.6 ± 0.2 | 8.6 ± 0.1 |
| 3 | 8.7 | 8.7 ± 0.2 | 8.7 ± 0.1 |
| 8 | 15.0 | 15.0 ± 0.2 | 15.0 ± 0.1 |
| 10 | 17.2 | 17.2 ± 0.2 | 17.2 ± 0.1 |
| 12 | 18.9 | 18.9 ± 0.2 | 18.9 ± 0.1 |
| 13 | 19.6 | 19.6 ± 0.2 | 19.6 ± 0.1 |
| 14 | 19.7 | 19.7 ± 0.2 | 19.7 ± 0.1 |
| 16 | 21.3 | 21.3 ± 0.2 | 21.3 ± 0.1 |
| 18 | 23.6 | 23.6 ± 0.2 | 23.6 ± 0.1 |
| 19 | 24.7 | 24.7 ± 0.2 | 24.7 ± 0.1 |
| 21 | 26.2 | 26.2 ± 0.2 | 26.2 ± 0.1 |
| 22 | 26.6 | 26.6 ± 0.2 | 26.6 ± 0.1 |
| 25 | 28.1 | 28.1 ± 0.2 | 28.1 ± 0.1 |
| 26 | 28.8 | 28.8 ± 0.2 | 28.8 ± 0.1 |
| 28 | 30.3 | 30.3 ± 0.2 | 30.3 ± 0.1 |

In certain embodiments, the Solid Form C is characterized by the XPRD peaks as set forth in any one of the embodiments described in paragraphs [0082], [0083] and [0084] above and one or more of the remaining different XPRD peaks selected from those described in the table immediately above (the remaining different peaks are selected from column 2 for embodiments in paragraph [0082], from column 3 for embodiments in paragraph [0083], or from column 4 for in paragraph [0084], respectively).

In certain embodiments, the Solid Form C is characterized by having XRPD peaks at approximately the positions (in degrees 2-theta or °2-theta) shown in any one of the second through four columns in the table below:

| No. | Pos. [°2θ] | Pos. [°2θ] | Pos. [°2θ] |
|---|---|---|---|
| 1 | 6.5940 | 6.5940 ± 0.2 | 6.5940 ± 0.1 |
| 2 | 8.6307 | 8.6307 ± 0.2 | 8.6307 ± 0.1 |
| 3 | 8.6800 | 8.6800 ± 0.2 | 8.6800 ± 0.1 |
| 4 | 9.8297 | 9.8297 ± 0.2 | 9.8297 ± 0.1 |

-continued

| No. | Pos. [°2θ] | Pos. [°2θ] | Pos. [°2θ] |
|---|---|---|---|
| 5 | 10.7748 | 10.7748 ± 0.2 | 10.7748 ± 0.1 |
| 6 | 13.9580 | 13.9580 ± 0.2 | 13.9580 ± 0.1 |
| 7 | 14.3052 | 14.3052 ± 0.2 | 14.3052 ± 0.1 |
| 8 | 15.0544 | 15.0544 ± 0.2 | 15.0544 ± 0.1 |
| 9 | 15.6976 | 15.6976 ± 0.2 | 15.6976 ± 0.1 |
| 10 | 17.2160 | 17.2160 ± 0.2 | 17.2160 ± 0.1 |
| 11 | 18.0435 | 18.0435 ± 0.2 | 18.0435 ± 0.1 |
| 12 | 18.8879 | 18.8879 ± 0.2 | 18.8879 ± 0.1 |
| 13 | 19.6118 | 19.6118 ± 0.2 | 19.6118 ± 0.1 |
| 14 | 19.6608 | 19.6608 ± 0.2 | 19.6608 ± 0.1 |
| 15 | 20.0644 | 20.0644 ± 0.2 | 20.0644 ± 0.1 |
| 16 | 21.3028 | 21.3028 ± 0.2 | 21.3028 ± 0.1 |
| 17 | 23.2634 | 23.2634 ± 0.2 | 23.2634 ± 0.1 |
| 18 | 23.5960 | 23.5960 ± 0.2 | 23.5960 ± 0.1 |
| 19 | 24.6607 | 24.6607 ± 0.2 | 24.6607 ± 0.1 |
| 20 | 25.5933 | 25.5933 ± 0.2 | 25.5933 ± 0.1 |
| 21 | 26.1792 | 26.1792 ± 0.2 | 26.1792 ± 0.1 |
| 22 | 26.6081 | 26.6081 ± 0.2 | 26.6081 ± 0.1 |
| 23 | 26.9510 | 26.9510 ± 0.2 | 26.9510 ± 0.1 |
| 24 | 27.5251 | 27.5251 ± 0.2 | 27.5251 ± 0.1 |
| 25 | 28.1084 | 28.1084 ± 0.2 | 28.1084 ± 0.1 |
| 26 | 28.8196 | 28.8196 ± 0.2 | 28.8196 ± 0.1 |
| 27 | 29.6231 | 29.6231 ± 0.2 | 29.6231 ± 0.1 |
| 28 | 30.3217 | 30.3217 ± 0.2 | 30.3217 ± 0.1 |
| 29 | 30.9037 | 30.9037 ± 0.2 | 30.9037 ± 0.1 |
| 30 | 31.4328 | 31.4328 ± 0.2 | 31.4328 ± 0.1 |
| 31 | 31.8088 | 31.8088 ± 0.2 | 31.8088 ± 0.1 |
| 32 | 32.7826 | 32.7826 ± 0.2 | 32.7826 ± 0.1 |
| 33 | 34.6364 | 34.6364 ± 0.2 | 34.6364 ± 0.1 |

In certain embodiments, the Solid Form C is characterized by the XPRD peaks as set forth in any one of the embodiments described in paragraphs [0082], [0083] and [0084] above and one or more of the remaining different XPRD peaks selected from those described in the table immediately above (the remaining different peaks are selected from column 2 for embodiments in paragraph [0082], from column 3 for embodiments in paragraph [0083], or from column 4 for in paragraph [0084], respectively).

Figure 26:
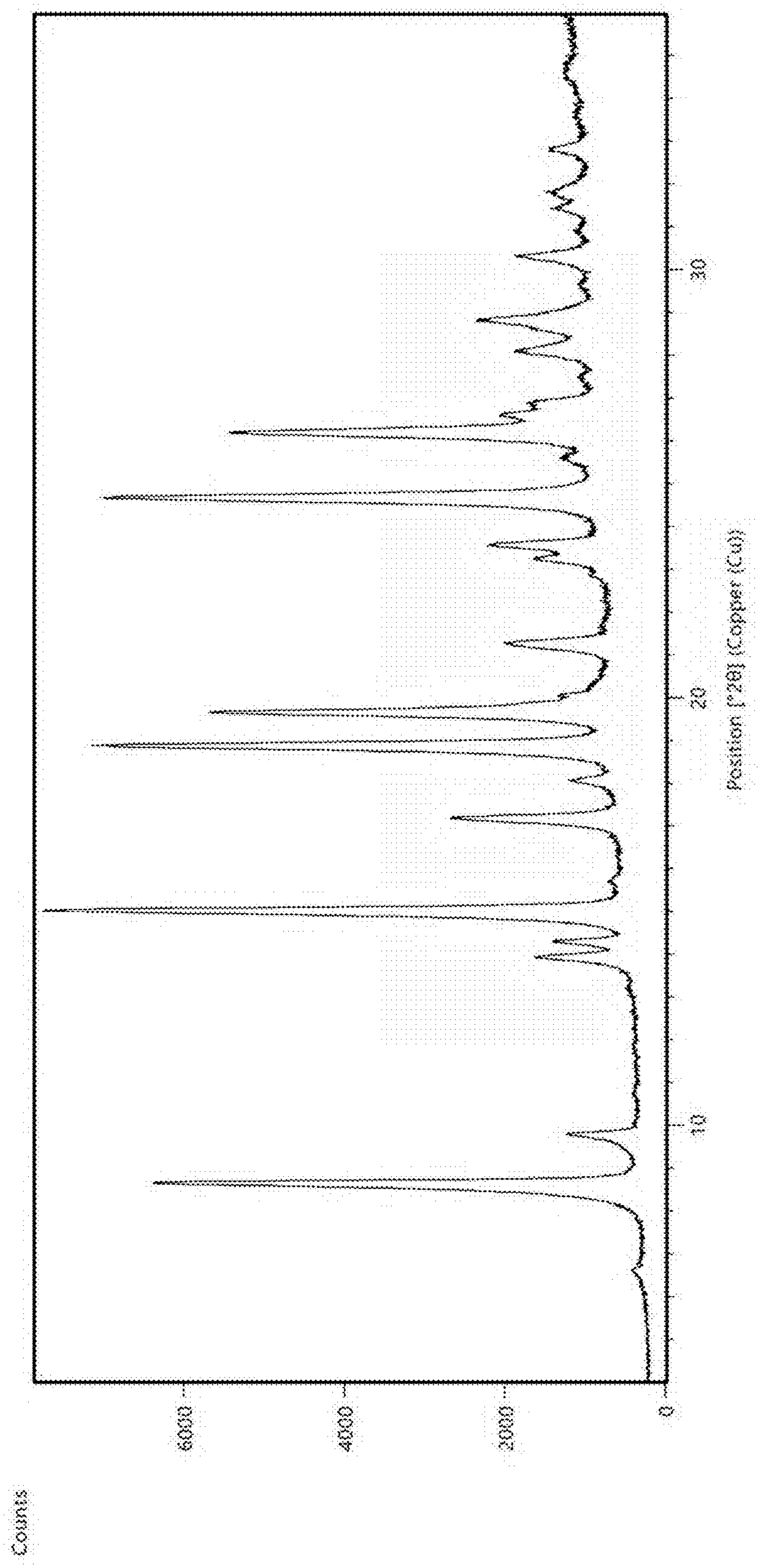
FIG. 26 is an XRPD of Solid Form C showing the range of angle from 0°2θ to 35°2θ.

In certain embodiments, the Solid Form C is characterized by an XRPD pattern substantially the same as that set forth in FIG. 26.

Solid Form D ("Form D")

In another aspect, the present disclosure provides a Solid Form D of Compound X characterized by having X-ray powder diffraction ("XRPD") peaks at approximately 6.8, 9.1, and 15.5°2θ using Cu Kα radiation. In certain embodiments, the Solid Form D is characterized by having XRPD peaks at approximately 6.8, 9.1, 14.3, 15.5, and 25.8°2θ using Cu Kα radiation. In certain embodiments, the Solid Form D is characterized by having XRPD peaks at approximately 6.8, 9.1, 13.6, 14.3, 15.5, 18.6, and 25.8°2θ using Cu Kα radiation. In certain embodiments, the Solid Form D is characterized by having XRPD peaks at approximately 6.8, 9.1, 13.6, 14.3, 15.5, 18.6, 20.9, 25.8, and 27.5°2θ using Cu Kα radiation. In certain embodiments, the Solid Form D is characterized by having XRPD peaks at approximately 6.8, 9.1, 13.6, 14.3, 15.5, 18.6, 20.9, 21.2, 24.5, 25.8, 27.5, and 27.7°2θ using Cu Kα radiation.

In one aspect, the present disclosure provides a Solid Form D of Compound X characterized by having X-ray powder diffraction ("XRPD") peaks at approximately 6.8±0.2, 9.1±0.2, and 15.5±0.2°2θ using Cu Kα radiation. In certain embodiments, the Solid Form D is characterized by having XRPD peaks at approximately 6.8±0.2, 9.1±0.2, 14.3±0.2, 15.5±0.2, and 25.8±0.2°2θ using Cu Kα radiation. In certain embodiments, the Solid Form Dis characterized by having XRPD peaks at approximately 6.8±0.2, 9.1±0.2, 13.6±0.2, 14.3±0.2, 15.5±0.2, 18.6±0.2, and 25.8±0.2°2θ using Cu Kα radiation. In certain embodiments, the Solid Form D is characterized by having XRPD peaks at approximately 6.8±0.2, 9.1±0.2, 13.6±0.2, 14.3±0.2, 15.5±0.2, 18.6±0.2, 20.9±0.2, 25.8±0.2, and 27.5±0.2°2θ using Cu Kα radiation. In certain embodiments, the Solid Form D is characterized by having XRPD peaks at approximately 6.8±0.2, 9.1±0.2, 13.6±0.2, 14.3±0.2, 15.5±0.2, 18.6±0.2, 20.9±0.2, 21.2±0.2, 24.5±0.2, 25.8±0.2, 27.5±0.2, and 27.7±0.2°2θ using Cu Kα radiation.

In one aspect, the present disclosure provides a Solid Form D of Compound X characterized by having X-ray powder diffraction ("XRPD") peaks at approximately 6.8±0.1, 9.1±0.1, and 15.5±0.1°2θ using Cu Kα radiation. In certain embodiments, the Solid Form D is characterized by having XRPD peaks at approximately 6.8±0.1, 9.1±0.1, 14.3±0.1, 15.5±0.1, and 25.8±0.1°2θ using Cu Kα radiation. In certain embodiments, the Solid Form D is characterized by having XRPD peaks at approximately 6.8±0.1, 9.1±0.1, 13.6±0.1, 14.3±0.1, 15.5±0.1, 18.6±0.1, and 25.8±0.1°2θ using Cu Kα radiation. In certain embodiments, the Solid Form D is characterized by having XRPD peaks at approximately 6.8±0.1, 9.1±0.1, 13.6±0.1, 14.3±0.1, 15.5±0.1, 18.6±0.1, 20.9±0.1, 25.8±0.1, and 27.5±0.1°2θ using Cu Kα radiation. In certain embodiments, the Solid Form D is characterized by having XRPD peaks at approximately 6.8±0.1, 9.1±0.1, 13.6±0.1, 14.3±0.1, 15.5±0.1, 18.6±0.1, 20.9±0.1, 21.2±0.1, 24.5±0.1, 25.8±0.1, 27.5±0.1, and 27.7±0.1°2θ using Cu Kα radiation.

In certain embodiments, the Solid Form D is characterized by having XRPD peaks at approximately the positions (in degrees 2-theta or °2-theta) shown in any one of the second through fourth columns in the table below:

| No. | Pos. [°2θ] | Pos. [°2θ] | Pos. [°2θ] |
|---|---|---|---|
| 1 | 6.8 | 6.8 ± 0.2 | 6.8 ± 0.1 |
| 2 | 9.1 | 9.1 ± 0.2 | 9.1 ± 0.1 |
| 6 | 13.4 | 13.4 ± 0.2 | 13.4 ± 0.1 |
| 7 | 13.6 | 13.6 ± 0.2 | 13.6 ± 0.1 |
| 8 | 14.3 | 14.3 ± 0.2 | 14.3 ± 0.1 |
| 9 | 15.5 | 15.5 ± 0.2 | 15.5 ± 0.1 |
| 10 | 15.8 | 15.8 ± 0.2 | 15.8 ± 0.1 |
| 11 | 16.4 | 16.4 ± 0.2 | 16.4 ± 0.1 |
| 15 | 18.6 | 18.6 ± 0.2 | 18.6 ± 0.1 |
| 20 | 20.9 | 20.9 ± 0.2 | 20.9 ± 0.1 |
| 21 | 21.2 | 21.2 ± 0.2 | 21.2 ± 0.1 |
| 28 | 24.3 | 24.3 ± 0.2 | 24.3 ± 0.1 |
| 29 | 24.5 | 24.5 ± 0.2 | 24.5 ± 0.1 |
| 31 | 25.4 | 25.4 ± 0.2 | 25.4 ± 0.1 |
| 32 | 25.8 | 25.8 ± 0.2 | 25.8 ± 0.1 |
| 33 | 26.3 | 26.3 ± 0.2 | 26.3 ± 0.1 |
| 35 | 27.0 | 27.0 ± 0.2 | 27.0 ± 0.1 |
| 36 | 27.5 | 27.5 ± 0.2 | 27.5 ± 0.1 |
| 37 | 27.7 | 27.7 ± 0.2 | 27.7 ± 0.1 |
| 39 | 28.9 | 28.9 ± 0.2 | 28.9 ± 0.1 |

In certain embodiments, the Solid Form D is characterized by the XPRD peaks as set forth in any one of the embodiments described in paragraphs [0092], [0093] and [0094] above and one or more of the remaining different XPRD peaks selected from those described in the table immediately above (the remaining different peaks are selected from column 2 for embodiments in paragraph [0092], from column 3 for embodiments in paragraph [0093], or from column 4 for in paragraph [0094], respectively).

In certain embodiments, the Solid Form D is characterized by having XRPD peaks at approximately the positions (in degrees 2-theta or °2-theta) shown in any one of the second through fourth columns in the table below:

| No. | Pos. [°2θ] | Pos. [°2θ] | Pos. [°2θ] |
|---|---|---|---|
| 1 | 6.7620 | 6.7620 ± 0.2 | 6.7620 ± 0.1 |
| 2 | 9.0830 | 9.0830 ± 0.2 | 9.0830 ± 0.1 |
| 6 | 13.3875 | 13.3875 ± 0.2 | 13.3875 ± 0.1 |
| 7 | 13.5658 | 13.5658 ± 0.2 | 13.5658 ± 0.1 |
| 8 | 14.3106 | 14.3106 ± 0.2 | 14.3106 ± 0.1 |
| 9 | 15.5483 | 15.5483 ± 0.2 | 15.5483 ± 0.1 |
| 10 | 15.7841 | 15.7841 ± 0.2 | 15.7841 ± 0.1 |
| 11 | 16.3531 | 16.3531 ± 0.2 | 16.3531 ± 0.1 |
| 15 | 18.5794 | 18.5794 ± 0.2 | 18.5794 ± 0.1 |
| 20 | 20.8796 | 20.8796 ± 0.2 | 20.8796 ± 0.1 |
| 21 | 21.2145 | 21.2145 ± 0.2 | 21.2145 ± 0.1 |
| 28 | 24.3098 | 24.3098 ± 0.2 | 24.3098 ± 0.1 |
| 29 | 24.4864 | 24.4864 ± 0.2 | 24.4864 ± 0.1 |
| 31 | 25.3756 | 25.3756 ± 0.2 | 25.3756 ± 0.1 |
| 32 | 25.7717 | 25.7717 ± 0.2 | 25.7717 ± 0.1 |
| 33 | 26.2770 | 26.2770 ± 0.2 | 26.2770 ± 0.1 |
| 35 | 27.0129 | 27.0129 ± 0.2 | 27.0129 ± 0.1 |
| 36 | 27.4745 | 27.4745 ± 0.2 | 27.4745 ± 0.1 |
| 37 | 27.7394 | 27.7394 ± 0.2 | 27.7394 ± 0.1 |
| 39 | 28.8764 | 28.8764 ± 0.2 | 28.8764 ± 0.1 |

In certain embodiments, the Solid Form D is characterized by the XPRD peaks as set forth in any one of the embodiments described in paragraphs [0092], [0093] and [0094] above and one or more of the remaining different XPRD peaks selected from those described in the table immediately above (the remaining different peaks are selected from column 2 for embodiments in paragraph [0092], from column 3 for embodiments in paragraph [0093], or from column 4 for in paragraph [0094], respectively).

In certain embodiments, the Solid Form D is characterized by having XRPD peaks at approximately the positions (in degrees 2-theta or °2-theta) shown in any one of the second through fourth columns in the table below:

| No. | Pos. [°2θ] | Pos. [°2θ] | Pos. [°2θ] |
|---|---|---|---|
| 1 | 6.7620 | 6.7620 ± 0.2 | 6.7620 ± 0.1 |
| 2 | 9.0830 | 9.0830 ± 0.2 | 9.0830 ± 0.1 |
| 3 | 10.0437 | 10.0437 ± 0.2 | 10.0437 ± 0.1 |
| 4 | 10.3865 | 10.3865 ± 0.2 | 10.3865 ± 0.1 |
| 5 | 11.0162 | 11.0162 ± 0.2 | 11.0162 ± 0.1 |
| 6 | 13.3875 | 13.3875 ± 0.2 | 13.3875 ± 0.1 |
| 7 | 13.5658 | 13.5658 ± 0.2 | 13.5658 ± 0.1 |
| 8 | 14.3106 | 14.3106 ± 0.2 | 14.3106 ± 0.1 |
| 9 | 15.5483 | 15.5483 ± 0.2 | 15.5483 ± 0.1 |
| 10 | 15.7841 | 15.7841 ± 0.2 | 15.7841 ± 0.1 |
| 11 | 16.3531 | 16.3531 ± 0.2 | 16.3531 ± 0.1 |
| 12 | 16.7632 | 16.7632 ± 0.2 | 16.7632 ± 0.1 |
| 13 | 16.9901 | 16.9901 ± 0.2 | 16.9901 ± 0.1 |
| 14 | 17.6541 | 17.6541 ± 0.2 | 17.6541 ± 0.1 |
| 15 | 18.5794 | 18.5794 ± 0.2 | 18.5794 ± 0.1 |
| 16 | 19.3010 | 19.3010 ± 0.2 | 19.3010 ± 0.1 |
| 17 | 19.7364 | 19.7364 ± 0.2 | 19.7364 ± 0.1 |
| 18 | 20.1838 | 20.1838 ± 0.2 | 20.1838 ± 0.1 |
| 19 | 20.4187 | 20.4187 ± 0.2 | 20.4187 ± 0.1 |
| 20 | 20.8796 | 20.8796 ± 0.2 | 20.8796 ± 0.1 |
| 21 | 21.2145 | 21.2145 ± 0.2 | 21.2145 ± 0.1 |
| 22 | 21.7605 | 21.7605 ± 0.2 | 21.7605 ± 0.1 |
| 23 | 22.2032 | 22.2032 ± 0.2 | 22.2032 ± 0.1 |
| 24 | 22.7825 | 22.7825 ± 0.2 | 22.7825 ± 0.1 |
| 25 | 23.3931 | 23.3931 ± 0.2 | 23.3931 ± 0.1 |
| 26 | 23.7498 | 23.7498 ± 0.2 | 23.7498 ± 0.1 |
| 27 | 24.0917 | 24.0917 ± 0.2 | 24.0917 ± 0.1 |
| 28 | 24.3098 | 24.3098 ± 0.2 | 24.3098 ± 0.1 |
| 29 | 24.4864 | 24.4864 ± 0.2 | 24.4864 ± 0.1 |
| 30 | 25.0330 | 25.0330 ± 0.2 | 25.0330 ± 0.1 |
| 31 | 25.3756 | 25.3756 ± 0.2 | 25.3756 ± 0.1 |

-continued

| No. | Pos. [°2θ] | Pos. [°2θ] | Pos. [°2θ] |
|---|---|---|---|
| 32 | 25.7717 | 25.7717 ± 0.2 | 25.7717 ± 0.1 |
| 33 | 26.2770 | 26.2770 ± 0.2 | 26.2770 ± 0.1 |
| 34 | 26.6857 | 26.6857 ± 0.2 | 26.6857 ± 0.1 |
| 35 | 27.0129 | 27.0129 ± 0.2 | 27.0129 ± 0.1 |
| 36 | 27.4745 | 27.4745 ± 0.2 | 27.4745 ± 0.1 |
| 37 | 27.7394 | 27.7394 ± 0.2 | 27.7394 ± 0.1 |
| 38 | 28.1211 | 28.1211 ± 0.2 | 28.1211 ± 0.1 |
| 39 | 28.8764 | 28.8764 ± 0.2 | 28.8764 ± 0.1 |
| 40 | 29.3707 | 29.3707 ± 0.2 | 29.3707 ± 0.1 |
| 41 | 30.0210 | 30.0210 ± 0.2 | 30.0210 ± 0.1 |
| 42 | 30.4091 | 30.4091 ± 0.2 | 30.4091 ± 0.1 |
| 43 | 30.8070 | 30.8070 ± 0.2 | 30.8070 ± 0.1 |
| 44 | 31.0792 | 31.0792 ± 0.2 | 31.0792 ± 0.1 |
| 45 | 31.6352 | 31.6352 ± 0.2 | 31.6352 ± 0.1 |
| 46 | 31.8773 | 31.8773 ± 0.2 | 31.8773 ± 0.1 |
| 47 | 32.1103 | 32.1103 ± 0.2 | 32.1103 ± 0.1 |
| 48 | 32.6600 | 32.6600 ± 0.2 | 32.6600 ± 0.1 |
| 49 | 32.9844 | 32.9844 ± 0.2 | 32.9844 ± 0.1 |
| 50 | 33.5978 | 33.5978 ± 0.2 | 33.5978 ± 0.1 |
| 51 | 33.9302 | 33.9302 ± 0.2 | 33.9302 ± 0.1 |
| 52 | 34.3658 | 34.3658 ± 0.2 | 34.3658 ± 0.1 |

In certain embodiments, the Solid Form D is characterized by the XPRD peaks as set forth in any one of the embodiments described in paragraphs [0092], [0093] and [0094] above and one or more of the remaining different XPRD peaks selected from those described in the table immediately above (the remaining different peaks are selected from column 2 for embodiments in paragraph [0092], from column 3 for embodiments in paragraph [0093], or from column 4 for in paragraph [0094], respectively).

Figure 27:
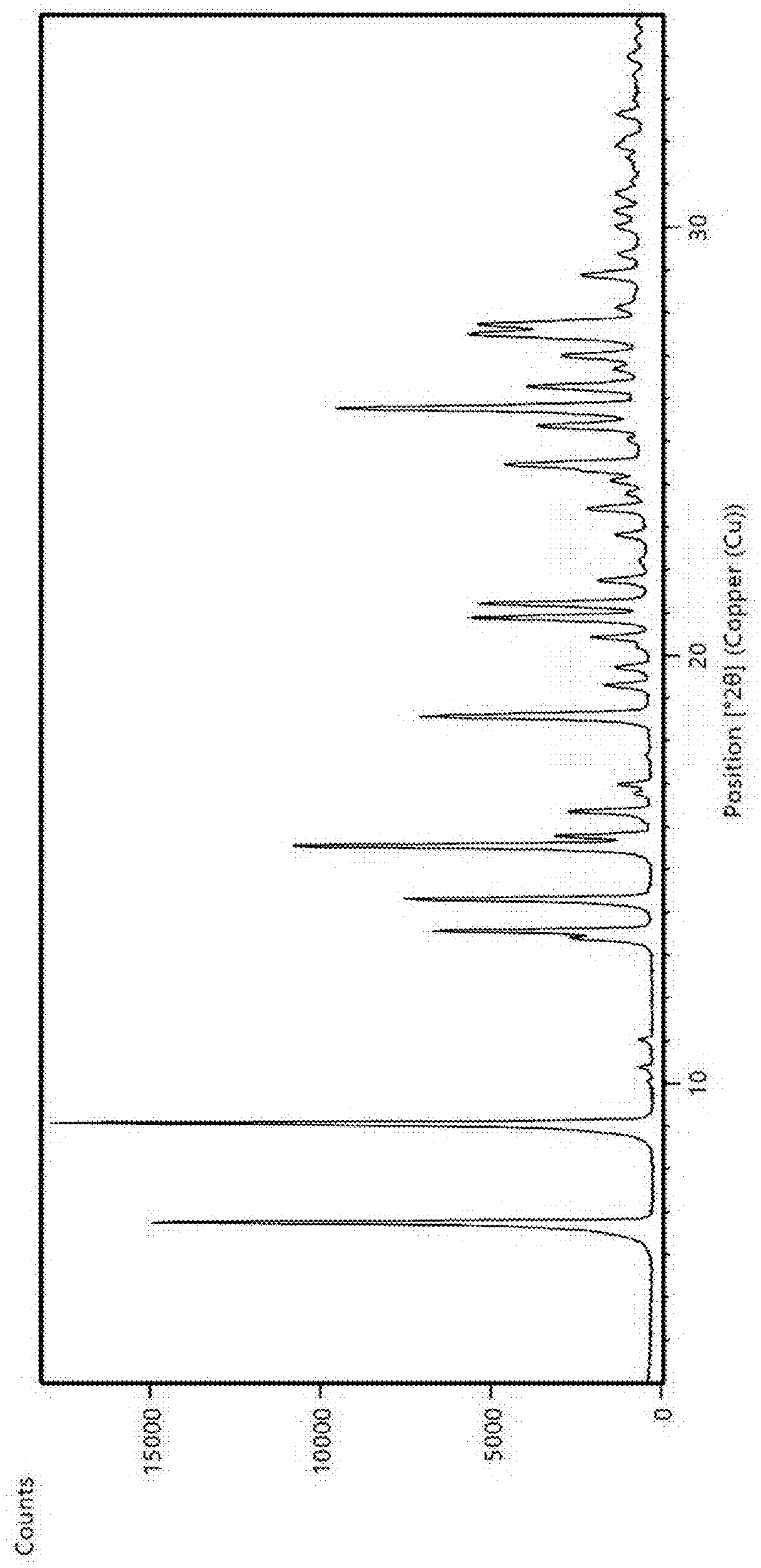
FIG. 27 is an XRDP of Solid Form D.

In certain embodiments, the Solid Form D is characterized by an XRPD pattern substantially the same as that set forth in FIG. 27.

In certain embodiments, the Solid Form D is characterized by an endothermic event with onset between approximately 45 °C and approximately 50 °C as measured DSC. In certain embodiments, the Solid Form D is characterized by an endothermic event with peak temperature at approximately 64 °C as measured by DSC. In certain embodiments, "approximately" means that the variability of the temperature is within ±3 °C. In certain embodiments, the Solid Form D is characterized by an endothermic event with onset between 45±3 °C and 50±3 °C as measured DSC. In certain embodiments, the Solid Form D is characterized by an endothermic event with peak temperature at 64±3 °C as measured by DSC. In certain embodiments, "approximately" means that the variability of the temperature is within ±2 °C. In certain embodiments, the Solid Form d is characterized by an endothermic event with onset between 45±°C and 50±2 °C as measured DSC. In certain embodiments, the Solid Form Dis characterized by an endothermic event with peak temperature at 64±2 °C as measured by DSC. In certain embodiments, "approximately" means that the variability of the temperature is within ±1 °C. In certain embodiments, the Solid Form D is characterized by an endothermic event with onset between 45±1 °C and 50±1 °C as measured DSC. In certain embodiments, the Solid Form D is characterized by an endothermic event with peak temperature at 64±1 °C as measured by DSC. In certain embodiments, the Solid Form D is characterized by a DSC thermogram substantially the same as that set forth in FIG. 28.

The terms "crystalline polymorphs", "crystal polymorphs", "crystal forms", "polymorphs", or "polymorphic forms" means crystal structures in which a compound (e.g., free base, salts, or solvates thereof) can crystallize in different crystal packing arrangements, all of which have the same elemental composition. Different crystal forms usually have different X-ray diffraction patterns, infrared spectra, melting points, density, crystal shape, optical and electrical properties, stability, and solubility. Crystallization solvent, rate of crystallization, storage temperature, and other factors may cause one crystal form to dominate. Crystal polymorphs of the compounds can be prepared by crystallization under different conditions. In addition, crystal polymorphism may be present but is not limiting, but any crystal form may be a single or a crystal form mixture, or an anhydrous or hydrated crystal form.

The term "amorphous form" refers to a noncrystalline solid state form of a substance.

Additionally, compounds (e.g., free bases and salts, and amorphous forms, crystalline forms, and polymorphs thereof) can exist in either hydrated or unhydrated (the anhydrous) form or as solvates with other solvent molecules or in an unsolvated form. Nonlimiting examples of hydrates include hemihydrates, monohydrates, dihydrates, etc. Nonlimiting examples of solvates include DMSO solvates, DMSO hemisolvates, acetone solvates, acetone hemisolvates, acetonitrile solvates, acetonitrile hemisolvates etc.

All forms of the compounds of the present application are contemplated, either in a mixture or in pure or substantially pure form, including crystalline forms of racemic mixtures and crystalline forms of individual isomers.

Polymorphs of a molecule can be obtained by a number of methods, as known in the art. Such methods include, but are not limited to, melt recrystallization, melt cooling, solvent recrystallization, desolvation, rapid evaporation, rapid cooling, slow cooling, vapor diffusion, and sublimation.

Techniques for characterizing solid forms of a compound, such as polymorphs, include, but are not limited to, DSC, X-ray powder diffractometry (XRPD), single crystal X-ray diffractometry, vibrational spectroscopy (e.g., IR or Raman spectroscopy), TGA, DTA, DVS, solid state NMR, hot stage optical microscopy, scanning electron microscopy (SEM), electron crystallography and quantitative analysis, particle size analysis (PSA), surface area analysis, solubility studies, and dissolution studies.

As used herein, the term "solvate" means solvent addition forms that contain either stoichiometric or non stoichiometric amounts of solvent. Some compounds have a tendency to trap a fixed molar ratio of solvent molecules in the crystalline solid state, thus forming a solvate. If the solvent is water the solvate formed is a hydrate, when the solvent is alcohol, the solvate formed is an alcoholate. Hydrates are formed by the combination of one or more molecules of water with one of the substances in which the water retains its molecular state as $H_2O$, such combination being able to form one or more hydrate. For example, the solvate may be a DMSO solvate, a dichloromethane (DCM) solvate, a methyl ethyl ketone (MEK solvate), an acetone solvate, an acetonitrile solvate, or a tetrahydrofuran (THF) solvate.

As used herein, the terms "unsolvated" or "desolvated" refer to a solid state form (e.g., crystalline forms, amorphous forms, and polymorphs) of a compound which does not contain solvent.

As used herein, the term "pure" means about the recited compound is present at a weight ratio or molar ratio of 90-100%, preferably 95-100%, more preferably 98-100% or 99-100%; e.g., less than about 10%, less than about 5%, less than about 2%, or less than about 1% impurity is present.

Such impurities include, e.g., degradation products, oxidized products, solvents, and/or other undesirable impurities.

As used herein, a compound is "stable" where significant amount of degradation products are not observed under constant conditions of humidity (e.g., 10%, 20%, 30%, 40%, 50%, 60%, 70%, 75%, 80%, 85%, 90%, or 95% relative humidity [RH]), light exposure and temperatures (e.g., higher than 0 °C, e.g., 20 °C, 25 °C, 30 °C, 35 °C, 40 °C, 45 °C, 50 °C, 55 °C, 60 °C, 65° C., or 70 °C) over a certain period (e.g., one week, two weeks, three weeks, or four weeks). A compound is not considered to be stable at a certain condition when degradation impurities appear or an area percentage (e.g., AUC as characterized by HPLC) of existing impurities begins to grow. The amount of degradation growth as a function of time is important in determining compound stability.

As used herein, the term "mixing" means combining, blending, stirring, shaking, swirling, or agitating. The term "stirring" means mixing, shaking, agitating, or swirling. The term "agitating" means mixing, shaking, stirring, or swirling.

Unless explicitly indicated otherwise, the terms "approximately" and "about" are synonymous. In certain embodiments, "approximately" and "about" refer to a recited amount, value, or duration ±10%, ±8%, ±6%, ±5%, ±4%, ±2%, ±1%, or ±0.5%. In some embodiments, "approximately" and "about" refer to a listed amount, value, or duration ±10%, ±8%, ±6%, ±5%, ±4%, or ±2%. In some embodiments, "approximately" and "about" refer to a listed amount, value, or duration ±5%. In some embodiments, "approximately" and "about" refer to a listed amount, value, or duration ±2% or +1%.

When the terms "approximately" and "about" are used when reciting XRPD peaks, these terms refer to the recited XRPD peak ±0.3°20, ±0.2°2θ, or ±0.1°2θ. In some embodiments, the terms "approximately" and "about" refer to the listed XRPD peak ±0.2°2θ. In some embodiments, the terms "approximately" and "about" refer to the listed XRPD peak ±0.1°2θ.

When the terms "approximately" and "about" are used when reciting temperature or temperature range, these terms refer to the recited temperature or temperature range ±5 °C, ±2° C., or ±1 °C. In some embodiments, the terms "approximately" and "about" refer to the recited temperature or temperature range ±2 °C

Pharmaceutical Compositions

In another aspect, the present disclosure also provides pharmaceutical compositions comprising a solid form of Compound X in combination with at least one pharmaceutically acceptable excipient or carrier.

In certain embodiments, the solid form is Solid Form A. In certain embodiments, the solid form is Solid Form B. In certain embodiments, the solid form is Solid Form C. In certain embodiments, the solid form is Solid Form D.

A "pharmaceutical composition" is a formulation containing the compounds of the present application in a form suitable for administration to a subject. In certain embodiments, the pharmaceutical composition is in bulk or in unit dosage form. The unit dosage form is any of a variety of forms, including, for example, a capsule, an IV bag, a tablet, a single pump on an aerosol inhaler or a vial. The quantity of active ingredient (e.g., a formulation of the one or more of the disclosed compounds) in a unit dose of composition is an effective amount and is varied according to the particular treatment involved. One skilled in the art will appreciate that it is sometimes necessary to make routine variations to the dosage depending on the age and condition of the patient. The dosage will also depend on the route of administration. A variety of routes are contemplated, including oral, pulmonary, rectal, parenteral, transdermal, subcutaneous, intravenous, intramuscular, intraperitoneal, inhalational, buccal, sublingual, intrapleural, intrathecal, intranasal, and the like. Dosage forms for the topical or transdermal administration of a compound of this disclosure include powders, sprays, ointments, pastes, creams, lotions, gels, solutions, patches and inhalants. In certain embodiments, the active compound is mixed under sterile conditions with a pharmaceutically acceptable carrier, and with any preservatives, buffers or propellants that are required.

As used herein, the phrase "pharmaceutically acceptable" refers to those compounds, materials, compositions, carriers, and/or dosage forms which are, within the scope of sound medical judgement, suitable for use in contact with the tissues of human beings and animals without excessive toxicity, irritation, allergic response, or other problem or complication, commensurate with a reasonable benefit/risk ratio.

"Pharmaceutically acceptable excipient" means an excipient that is useful in preparing a pharmaceutical composition that is generally safe, non-toxic and neither biologically nor otherwise undesirable, and includes an excipient that is acceptable for veterinary use as well as human pharmaceutical use. A "pharmaceutically acceptable excipient" as used in the specification and claims includes both one and more than one such excipient.

A pharmaceutical composition of the application is formulated to be compatible with its intended route of administration. Examples of routes of administration include parenteral, e.g., intravenous, intradermal, subcutaneous, oral (e.g., inhalation), transdermal (topical), and transmucosal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made glass or plastic.

A compound or pharmaceutical composition of the application can be administered to a subject in many of the well-known methods currently used for chemotherapeutic treatment. For example, for treatment of cancers, a compound of the application may be injected directly into tumors, injected into the blood stream or body cavities or taken orally or applied through the skin with patches. The dose chosen should be sufficient to constitute effective treatment but not as high as to cause unacceptable side effects. The state of the disease condition (e.g., cancer, precancer, and the like) and the health of the patient should preferably be closely monitored during and for a reasonable period after treatment.

The term "therapeutically effective amount", as used herein, refers to an amount of a pharmaceutical agent to treat, ameliorate, or prevent an identified disease or condition, or to exhibit a detectable therapeutic or inhibitory effect. The effect can be detected by any assay method known in the art. The precise effective amount for a subject will depend upon the subject's body weight, size, and health; the nature and extent of the condition; and the therapeutic or combination of therapeutics selected for administration. Therapeutically effective amounts for a given situation can be determined by routine experimentation that is within the skill and judgment of the clinician. In certain embodiments, the disease or disorder is selected from immune disorders, cancer, cardiovascular diseases, viral infections, inflammation, metabolism/endocrine function disorders and neurological disorders. In another embodiment, the disease or condition to be treated is cancer. In certain embodiments, the disease or condition to be treated is a cell proliferative disorder.

For any compound, the therapeutically effective amount can be estimated initially either in cell culture assays, e.g., of neoplastic cells, or in animal models, usually rats, mice, rabbits, dogs, or pigs. The animal model may also be used to determine the appropriate concentration range and route of administration. Such information can then be used to determine useful doses and routes for administration to humans. Therapeutic/prophylactic efficacy and toxicity may be determined by standard pharmaceutical procedures in cell cultures or experimental animals, e.g., $ED_{50}$ (the dose therapeutically effective in 50% of the population) and $LD_{50}$ (the dose lethal to 50% of the population). The dose ratio between toxic and therapeutic effects is the therapeutic index, and it can be express as the ratio, $LD_{50}/ED_{50}$. Pharmaceutical compositions that exhibit large therapeutic indices are preferred. The dosage may vary within this range depending upon the dosage form employed, sensitivity of the patient, and the route of administration.

Dosage and administration are adjusted to provide sufficient levels of the active agent(s) or to maintain the desired effect. Factors which may be taken into account include the severity of the disease state, general health of the subject, age, weight, and gender of the subject, diet, time and frequency of administration, drug combination(s), reaction sensitivities, and tolerance/response to therapy. Long-acting pharmaceutical compositions may be administered every 3 to 4 days, every week, or once every two weeks depending on half-life and clearance rate of the particular formulation.

The pharmaceutical compositions containing active compounds of the present application may be manufactured in a manner that is generally known, e.g., by means of conventional mixing, dissolving, granulating, dragee-making, levigating, emulsifying, encapsulating, entrapping, or lyophilizing processes. Pharmaceutical compositions may be formulated in a conventional manner using one or more pharmaceutically acceptable carriers comprising excipients and/or auxiliaries that facilitate processing of the active compound into preparations that can be used pharmaceutically. Of course, the appropriate formulation is dependent upon the route of administration chosen.

Pharmaceutical compositions suitable for injectable use include sterile aqueous solutions (where water soluble) or dispersions and sterile powders for the extemporaneous preparation of sterile injectable solutions or dispersions. For intravenous administration, suitable carriers include physiological saline, bacteriostatic water, Cremophor EL™ (BASF, Parsippan, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as mannitol, sorbitol, and sodium chloride in the composition. Prolonged absorption of the injectable composition can be brought about by including in the composition an agent which delays absorption, for example, aluminum monostearate and gelatin.

Sterile injectable solutions can be prepared by incorporating the active compound in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible pharmaceutically acceptable carrier. They can be enclosed in gelatin capsules or compressed into tables. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compound is delivered in the form of an aerosol spray from a pressured container or dispenser, which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The active compounds can be prepared with pharmaceutically acceptable carriers that will protect the Compound X against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the application are dictated by and directly dependent on the unique characteristics of the active Compound X and the particular therapeutic effect to be achieved.

In therapeutic applications, the dosages of the pharmaceutical compositions used in accordance with the application vary depending on the agent, the age, weight, and clinical condition of the recipient patient, and the experience and judgment of the clinician or practitioner administering the therapy, among other factors affecting the selected dosage. Generally, the dose should be sufficient to result in slowing, and preferably regressing, the growth of the tumors and also preferably causing complete regression of the cancer. Dosages can range from about 0.01 mg/kg per day to about 5000 mg/kg per day. An effective amount of a pharmaceutical agent is that which provides an objectively identifiable improvement as noted by the clinician or other qualified observer. For example, regression of a tumor in a patient may be measured with reference to diameter of a tumor. Decrease in the diameter of a tumor indicates regression. Regression is also indicated by failure of tumors to reoccur after treatment has stopped. As used herein, the term "dosage effective manner" refers to an amount of an active compound to produce the desired biological effect in a subject or cell.

The pharmaceutical compositions can be included in a container, pack, or dispenser together with instructions for administration.

As used herein, "pharmaceutically acceptable salts" refer to derivatives of the compound of the present application wherein the parent compound is modified by making acid or base salts thereof. Examples of pharmaceutically acceptable salts include, but are not limited to, mineral or organic acid salts of basic residues such as amines, alkali or organic salts of acidic residues such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include, but are not limited to, those derived from inorganic and organic acids selected from 2-acetoxybenzoic, 2-hydroxyethane sulfonic, acetic, ascorbic, benzene sulfonic, benzoic, bicarbonic, carbonic, citric, edetic, ethane disulfonic, 1,2-ethane sulfonic, fumaric, glucoheptonic, gluconic, glutamic, glycolic, glycollyarsanilic, hexylresorcinic, hydrabamic, hydrobromic, hydrochloric, hydroxymaleic, hydroxynaphthoic, isethionic, lactic, lactobionic, lauryl sulfonic, maleic, malic, mandelic, methane sulfonic, napsylic, nitric, oxalic, pamoic, pantothenic, phenylacetic, phosphoric, polygalacturonic, propionic, salicyclic, stearic, subacetic, succinic, sulfamic, sulfanilic, sulfuric, tannic, tartaric, toluene sulfonic, and the commonly occurring amine acids, e.g., glycine, alanine, phenylalanine, arginine, etc.

Other examples of pharmaceutically acceptable salts include hexanoic acid, cyclopentane propionic acid, pyruvic acid, malonic acid, 3-(4-hydoxybenzoyl)benzoic acid, cinnamic acid, 4-chlorobenzenesulfonic acid, 2-naphthalenesulfonic acid, 4-toluenesulfonic acid, camphorsulfonic acid, 4-methylbicyclo-[2.2.2]-oct-2-ene-1-carboxylic acid, 3-phenylpropionic acid, trimethylacetic acid, tertiary butylacetic acid, muconic acid, and the like. The present application also encompasses salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

It should be understood that all references to pharmaceutically acceptable salts include solvent addition forms (solvates) or crystal forms (polymorphs) as defined herein of the same salt.

The compound of the present application can also be prepared as esters, for example, pharmaceutically acceptable esters. For example, a carboxylic acid function group in a compound can be converted to its corresponding ester, e.g., a methyl, ethyl or other ester. Also, an alcohol group in a compound can be converted to its corresponding ester, e.g., an acetate, propionate or other ester.

The compound, or pharmaceutically acceptable salts, tautomers, prodrugs, solvates, metabolites, polymorphs, analogs or derivatives thereof, are administered orally, nasally, transdermally, pulmonary, inhalationally, buccally, sublingually, intraperintoneally, subcutaneously, intramuscularly, intravenously, rectally, intrapleurally, intrathecally and parenterally. In certain embodiments, the compound or a pharmaceutically acceptable salt, tautomer, prodrug, solvate, metabolite, polymorph, analog or derivative thereof is administered orally. One skilled in the art will recognize the advantages of certain routes of administration.

The dosage regimen utilizing the compound is selected in accordance with a variety of factors including type, species, age, weight, sex and medical condition of the patient; the severity of the condition to be treated; the route of administration; the renal and hepatic function of the patient; and the particular compound or pharmaceutically acceptable salt, tautomer, prodrug, solvate, metabolite, polymorph, analog or derivative thereof employed. An ordinarily skilled physician or veterinarian can readily determine and prescribe the effective amount of the drug required to prevent, counter or arrest the progress of the condition.

Techniques for formulation and administration of the disclosed compounds of the present application can be found in *Remington: the Science and Practice of Pharmacy,* $19^{th}$ edition, Mack Publishing Co., Easton PA (1995). In an embodiment, the compounds described herein, are used in pharmaceutical preparations in combination with a pharmaceutically acceptable carrier or diluent. Suitable pharmaceutically acceptable carriers include inert solid fillers or diluents and sterile aqueous or organic solutions. The compounds will be present in such pharmaceutical compositions in amounts sufficient to provide the desired dosage amount in the range described herein.

Methods of Treatment

In a further aspect, the present disclosure provides methods of inhibiting PDE9 in a subject, comprising administering to the subject a solid form of Compound X. In certain embodiments, the solid form is Solid Form A. In certain embodiments, the solid form is Solid Form B. In certain embodiments, the solid form is Solid Form C. In certain embodiments, the solid form is Solid Form D.

The present disclosure also provides methods of treating a disease or disorder, comprising administering to a subject in need thereof an amount of a solid form of Compound X. In certain embodiments, the solid form is Solid Form A. In certain embodiments, the solid form is Solid Form B. In certain embodiments, the solid form is Solid Form C. In certain embodiments, the solid form is Solid Form D. In certain embodiments, the amount is a therapeutically effective amount. In certain embodiments, the disease or disorder is mediated by PDE9 or in which PDE9 is involved or plays a role in the initiation and/or development.

In certain embodiments, the disease or disorder is a neurodegenerative disease or disorder, cardiovascular disorder or disease, urogenital system such as sexual dysfunction, attention deficit disorder (ADD), attention deficit hyperactivity disorder (ADHD), diabetes, cognitive impairment, cognitive dysfunction, obesity, or cardiometabolic syndrome.

The present disclosure also provides methods of treating a neurodegenerative disease or disorder, comprising administering to the subject in need thereof an amount of a solid form of Compound X. The present disclosure further provides methods of preventing a neurodegenerative disease or disorder, comprising administering to a subject in need thereof an amount of a solid form of Compound X. In certain embodiments, the solid form is Solid Form A. In certain embodiments, the solid form is Solid Form B. In certain embodiments, the solid form is Solid Form C. In certain embodiments, the solid form is Solid Form D. In certain embodiments, the amount is a therapeutically effective amount.

The present disclosure further provides use of a solid form of Compound X in the manufacture of a medicament for the treatment or prevention of a neurodegenerative disease or disorder. In certain embodiments, the solid form is Solid Form A. In certain embodiments, the solid form is Solid Form B. In certain embodiments, the solid form is Solid Form C. In certain embodiments, the solid form is Solid Form D.

A neurodegenerative disease or disorder is a disease and disorder associated with neurodegeneration. The neurodegenerative disease of the present disclosure may include Alexander disease, Alper's disease, Alzheimer's disease, amyotrophic lateral sclerosis (ALS; also known as Lou Gehrig's disease or motor neuron disease), ataxia-telangiectasia, Batten disease (also known as Spielmeyer-Vogt-Sjogren-Batten disease), Binswanger's dementia (subcortical arteriosclerotic encephalopathy), bipolar disorders, bovine spongifonn encephalopathy (BSE), Canavan disease, chemotherapy-in-duced dementia, Cockayne syndrome, corticobasal degeneration, Creutzfeldt-Jakob disease, depression, Down syndrome, frontotemporal lobar degeneration (including frontotemporal dementia, semantic dementia, and progressive nonfluent aphasia), Gerstmann-Strai.issler-Scheinker disease, glaucoma, Huntington's disease (chorea), HIV-associated dementia, hyperkinesias, Kem1edy's disease, Korsakoff s syndrome (anmesic-confabulatory syndrome), Krabbe's disease, Lewy body dementia, logopenic progressive aphasia, Machado-Joseph disease (spinocerebellar ataxia type 3), multiple sclerosis, multiple system atrophy (olivopontocerebellar atrophy), myasthenia gravis, Parkinson's disease, Pelizaeus-Merzbacher disease, Pick's disease, presenile dementia (mild cognitive impairment), primary lateral sclerosis, primary progressive aphasia, radiation-induced dementia, Refsum's disease (phytanic acid storage disease), Sandhoff disease, Schilder's disease, schizophrenia, semantic dementia, senile dementia, Shy-Drager syndrome, spinocerebellar ataxias, spinal muscular atrophies, Steele-Richardson-Olszewski disease (progressive supranuclear palsy), tabes dorsalis, tardive dyskinesia, vascular amyloidosis, and vascular dementia (multi-infarct dementia).

In certain preferred embodiments, the neurodegenerative disease or disorder is Alzheimer's disease.

The present disclosure also provides methods of treating a cardiovascular disease or disorder, comprising administering to a subject in need thereof an amount of a solid form of Compound X. The present disclosure further provides methods of preventing a cardiovascular disease or disorder, comprising administering to a subject in need thereof an amount of a solid form of Compound X. In certain embodiments, the solid form is Solid Form A. In certain embodiments, the solid form is Solid Form B. In certain embodiments, the solid form is Solid Form C. In certain embodiments, the solid form is Solid Form D. In certain embodiments, the amount is a therapeutically effective amount.

The cardiovascular disorder or disease may include systemic hypertension, pulmonary hypertension, congestive heart failure, coronary artery disease, atherosclerosis, stroke, thrombosis, conditions of reduced blood vessel patency (e.g. post-percutaneous transluminal coronary angioplasty), peripheral vascular disease, renal disease associated with cardiovascular issues, angina (including stable, UI1stable, and variant (Prinzmetal) angina), aorta disease, Marfan syndrome, heart muscle disease, congenital heart disease, deep vein thrombosis, heart failure, pericardial disease, heart valve disease, rheumatic heart disease, and any condition where improved blood flow leads to improved end organ function.

Other diseases or disorders associated with PDE9 that may be treated or prevented by the methods of the present disclosure include diseases or disorders of the urogenital system such as sexual dysfunction, attention deficit disorder (ADD), attention deficit hyperactivity disorder (ADHD), diabetes.

The present disclosure also provides methods of treating cardiometabolic syndrome or obesity, comprising administering to a subject in need thereof an amount of a solid form of Compound X. The present disclosure further provides methods of preventing cardiometabolic syndrome or obesity, comprising administering to a subject in need thereof an amount of a solid form of Compound X. In certain embodiments, the solid form is Solid Form A. In certain embodiments, the solid form is Solid Form B. In certain embodiments, the solid form is Solid Form C. In certain embodiments, the solid form is Solid Form D. In certain embodiments, the amount is a therapeutically effective amount.

The present disclosure further provides use of a solid form of Compound X in the manufacture of a medicament for the treatment or prevention of cardiometabolic syndrome or obesity. In certain embodiments, the solid form is Solid Form A. In certain embodiments, the solid form is Solid Form B. In certain embodiments, the solid form is Solid Form C. In certain embodiments, the solid form is Solid Form D.

In some embodiments, the obesity is central obesity (i.e., abdominal obesity or central adiposity).

In some embodiments, the subject is a male. In some embodiments, the subject is a female.

The present disclosure also provides methods for promoting neurorestoration and functional recovery in a subject suffering from traumatic or non-traumatic brain, spinal cord or peripheral nerves injuries. Traumatic brain injuries include both closed head injuries (in which the skull is not broken) and open, or penetrating, head injuries (in which an object pierces the skull and breaches the dura mater), wherein sudden trauma (e.g., accidents, falls, or assaults) causes damage to the brain tissue by tearing, stretching, bruising, or swelling. Causes of non-traumatic brain injuries include aneurism, stroke, meningitis, oxygen deprivation due to anoxia, hypoxia, or ischemia, brain tumor, infection (e.g. encephalitis), poisoning, substance abuse, and the like.

The present disclosure provides methods of treating cognitive impairment and cognitive dysfunction resulting from brain injuries as well as from neurodegenerative diseases and disorders.

The present disclosure also provides methods of improving cognitive deficits, including deficits in perception, concentration, learning, memory, communication, reasoning, and problem-solving.

As used herein, "treating" or "treat" describes the management and care of a patient for the purpose of combating a disease, condition, or disorder, and includes the administration of a compound of the present application to alleviate the symptoms or complications of a disease, condition or disorder, or to eliminate the disease, condition or disorder.

As used herein, "preventing" or "prevent" describes reducing or eliminating the onset of the symptoms or complications of the disease, condition or disorder.

As used herein, the term "alleviate" is meant to describe a process by which the severity of a sign or symptom of a disorder is decreased. Importantly, a sign or symptom can be alleviated without being eliminated. In a preferred embodiment, the administration of a compound of the present application leads to the elimination of a sign or symptom, however, elimination is not required. Effective dosages are expected to decrease the severity of a sign or symptom. For instance, a sign or symptom of a disorder such as cancer, which can occur in multiple locations, is alleviated if the severity of the cancer is decreased within at least one of multiple locations.

As used herein, the term "symptom" is defined as an indication of disease, illness, injury, or that something is not right in the body. Symptoms are felt or noticed by the individual experiencing the symptom, but may not easily be noticed by others.

As used herein, the term "sign" is also defined as an indication that something is not right in the body. However, signs are defined as things that can be seen by a doctor, nurse, or other health care professional.

All percentages and ratios used herein, unless otherwise indicated, are by weight. Other features and advantages of the present application are apparent from the different examples. The provided examples illustrate different components and methodology useful in practicing the present application. The examples do not limit the claimed application. Based on the present application the skilled artisan can identify and employ other components and methodology useful for practicing the present application.

EXAMPLES

The application is further illustrated by the following examples, which are not to be construed as limiting this application in scope or spirit to the specific procedures herein described. It is to be understood that the examples are provided to illustrate certain embodiments and that no limitation to the scope of the application is intended thereby. It is to be further understood that resort may be had to various other embodiments, modifications, and equivalents thereof which may suggest themselves to those skilled in the art without departing from the spirit of the present application and/or scope of the appended claims.

Materials and Methods:

X-Ray Powder Diffraction

XRPD patterns were collected on a Bruker-AXS Ltd. D4 Endeavor powder X-ray diffractometer fitted with an automatic sample changer, a theta-two theta goniometer, automatic beam divergence slit, and a PSD Vantec-1 detector. The X-ray tube voltage and amperage were set to 35 kV and 40 mA respectively. Data was collected at the Cu wavelength from 2.0 to 55.0 degrees 2-theta (°2θ) using a step size of 0.018°2θ and a time per step of 0.2 seconds. The sample powders were prepared by placing the powder in a silicon low background cavity holder and rotated at 60 rpm during data collection. Data were analysed in DIFFRAC.EVA V5.0 software (e.g., for Solid Form A); alternatively, XRPD analysis was carried out on a PANalytical X'pert pro with PIXcel detector (128 channels), scanning the samples between 3 and 35°2θ (e.g., for Solid Forms B and C). The material was gently ground to release any agglomerates and loaded onto a multi-well plate with Kapton or Mylar polymer film to support the sample. The multi-well plate was then placed into the diffractometer and analyzed using Cu K radiation (α1λ=1.54060 Å; α2=1.54443 Å; β=1.39225 Å; α1:α2 ratio=0.5) running in transmission mode (step size 0.0130°2θ, step time 18.87 s) using 40 kV/40 mA generator settings. Data were visualized and images generated using the HighScore Plus 4.9 desktop application (PANalytical, 2020).

To obtain the absolute peak positions, the powder pattern was aligned against the simulated powder pattern from the crystal structure of the same form solved at room temperature.

Differential Scanning Calorimetry 1.487 mg of Solid Form A was weighed into an aluminium Tzero pan. This was sealed with a Tzero lid and crimped shut. The sample was run on a TA Instruments Discovery differential scanning calorimeter against an empty reference pan of the same type, using a method that heated the sample from 25 °C to 275 °C at 10 °C/minute, with a nitrogen purge gas; alternatively, approximately 1-5 mg of material was weighed into an aluminum DSC pan and sealed non-hermetically with an aluminum lid. The sample pan was then loaded into a TA Instruments Discovery DSC 2500 differential scanning calorimeter equipped with a RC90 cooler. The sample and reference were heated to 190 °C at a scan rate of 10 °C/min and the resulting heat flow response monitored. The sample was re-cooled to 20 °C and then reheated again to 190 °C all at 10 °C/min. Nitrogen was used as the purge gas, at a flow rate of 50 $cm^3$/min.

ThermoGravimetric Analysis 10.9587 mg of Solid Form A was placed in a platinum crucible. This was analysed on a TA Instruments Discovery ThermoGravimetric Analyser, using a method that heated the sample from 25 °C to 300 °C at 10 °C/minute with a nitrogen purge gas; alternatively, approximately 5-10 mg of material was weighed into an open aluminum pan and loaded into a simultaneous thermogravimetric/differential thermal analyzer (TG/DTA) and held at room temperature. The sample was then heated at a rate of 10 °C/min from 20 °C to 400 °C during which time the change in sample weight was recorded along with any differential thermal events (DTA). Nitrogen was used as the purge gas, at a flow rate of 300 $cm^3$/min.

Polarized Light Microscopy (PLM)

The presence of crystallinity (birefringence) was determined using an Olympus BX53 microscope, equipped with cross-polarizing lenses and a Motic camera. Images were captured using Motic Images Plus 3.0. All images were recorded using the 20× objective, unless otherwise stated.

Karl Fischer Coulometric Titration (KF)

ca. 10-15 mg of solid material was accurately weighed into a vial. The solid was then manually introduced into the titration cell of a Mettler Toledo C30 Compact Titrator. The vial was back-weighed after the addition of the solid and the weight of the added solid entered on the instrument. Titration was initiated once the sample had fully dissolved in the cell. The water content was calculated automatically by the instrument as a percentage and the data printed.

Infrared Spectroscopy (FT-IR)

Infrared spectroscopy was carried out on a Bruker ALPHA P spectrometer. Sufficient material was placed onto the center of the plate of the spectrometer and the spectra were obtained using the following parameters:

Resolution: 4 cm-1

Background Scan Time: 16 scans

Sample Scan Time: 16 scans

Data Collection: 4000 to 400 cm-1

Result Spectrum: Transmittance

Software: OPUS version 6

Nuclear Magnetic Resonance (NMR)

NMR experiments were performed on a Bruker A VIIIHD spectrometer equipped with a DCH cryoprobe operating at 500.12 MHz for protons. Experiments were performed in deuterated dimethylsulfoxide, and each sample was prepared to ca. 10 mM concentration.

Variable Temperature X-Ray Powder Diffraction (VT-XRPD)

VT-XRPD analysis was carried out on a Philips X'Pert Pro Multipurpose diffractometer equipped with a temperature chamber. The samples were scanned between 4 and 35.99°2θ using Cu K radiation (α1λ=1.54060 Å; α2=1.54443 Å; β=1.39225 Å; α1:α2 ratio=0.5) running in Bragg-Brentano geometry (step size 0.008°2θ) using 40 kV/40 mA generator settings.

Variable Humidity X-Ray Powder Diffraction (VH-XRPD)

VH-XRPD analysis was carried out on a Philips X'Pert Pro Multipurpose diffractometer equipped with a humidity chamber. The samples were scanned between 4 and 35.99°2θ using Cu K radiation (α1λ=1.54060 Å; α2=1.54443 Å; β=1.39225 Å; α1:α2 ratio=0.5) running in Bragg-Brentano geometry (step size 0.008°2θ) using 40 kV/40 mA generator settings.

High Performance Liquid Chromatography-Ultraviolet Detection (HPLC-UV)

| | |
|---|---|
| Instrument | Thermo-Dionex Ultimate 3000 UHPLC |
| Column | Waters Atlantis T3 3.0 μm 150 mm × 4.6 mm |
| Column Temperature | 30 |

-continued

| | |
|---|---|
| Flow Rate (mL/min) | 0.8 |
| Injection Volume (μL) | 4 |
| Autosampler Temperature (°C) | Ambient |
| Detection Parameters | UV @ 210 nm |
| Mobile Phase A | 0.1% Perchloric acid in H2O |
| Mobile Phase B | Acetonitrile |
| Diluent | Water:Acetonitrile (70:30 % v/v) |
| Needle Wash | Water:Acetonitrile (50:50 % v/v) |
| Working Concentration (mg/mL) | 0.4 |

| Gradient | | |
|---|---|---|
| Time (minutes) | MP A % | MP B % |
| 0.0 | 90 | 10 |
| 15.0 | 80 | 20 |
| 25.0 | 10 | 90 |
| 28.0 | 10 | 90 |
| 28.1 | 90 | 10 |
| 35.0 | 90 | 10 |

Mass Spectrometry

HPLC Instrument: Agilent 1290 with an Agilent 6410 Triple quadrupole MS

Column: X-Bridge C18, 50 mm×3 mm, 3.5 μm or similar

Column Temperature: 40 °C

Autosampler Temperature: Ambient

Detector parameters: UV 210 nm Monitor only

UV Scan 190 to 900 nm

MS+/−ESI Fragmentor 135 V

Injection Volume: 1 μL

Flow Rate: 1.0 mL/min

Mobile Phase A: 0.1% Formic acid in deionised water

Mobile Phase B: 0.1% Formic acid in acetonitrile

Gradient Program:

| Time (minutes) | Solvent B [%] |
|---|---|
| 0.0 | 5 |
| 8.0 | 95 |
| 10.0 | 95 |
| 10.1 | 5 |
| 14.0 | 5 |

Example 1. Solid Form A

Preparation of Solid Form A

Two crystallization steps were carried out for Compound X, one prior to a chromatography step, and one after a chromatography step.

Pre Chromatography Isolation

Compound X was prepared by reacting 6-((3S,4S)-4-methylpyrrolidin-3-yl)-1-(tetrahydro-2H-pyran-4-yl)-1,5-dihydro-4H-pyrazolo[3,4-d]pyrimidin-4-one with 2-(chloromethyl)pyrimidine hydrogen chloride in the presence of cesium carbonate. This step was carried out in a 2-methyl THF/water biphasic mix. At the end of the reaction the aqueous phase was removed, such that Compound X was in a predominantly 2-methyl THF organic phase. This was filtered to remove carbon, concentrated at 68-88 °C to approximately 5.3 volumes, then cooled to 20-30 °C. Five volumes of n-heptane were then added at 20-30 °C. The mixture became biphasic during parts of the addition. The mix was held for at least 5 hours at 20-30 °C during which time a product precipitated. The product was filtered and washed with a further 2 volumes of n-heptane. The crude product was then dried in a vacuum dryer with a slight nitrogen sweep at 35-45 °C Final Crystallization Step After the crude product was chromatographed, it was concentrated up and then exchanged into isopropyl alcohol. n-heptane was added to the reaction vessel while the temperature was maintained at 35 °C-55 °C, achieving a ratio of 3:1 of IPA:n-heptane. The mixture was heated to 70-80 °C and held at this temperature to dissolve any solids present. The mixture was then cooled to 15 °C over at least 3 hours, during which time crystallization occurred. Further n-heptane was added to achieve a ratio of 1:1.4 of IPA:n-heptane. The mixture was then held for at least 12 hours at 15 °C. The product was filtered, and the reactor was washed with n-heptane onto the filter to transfer all the solid to the filter. The solids were dried by blowing with nitrogen for 1 hour, and then dried under vacuum with a nitrogen sweep, to a solid that contained less than 0.5% IPA and less than 0.5% n-heptane.

Figure 11:
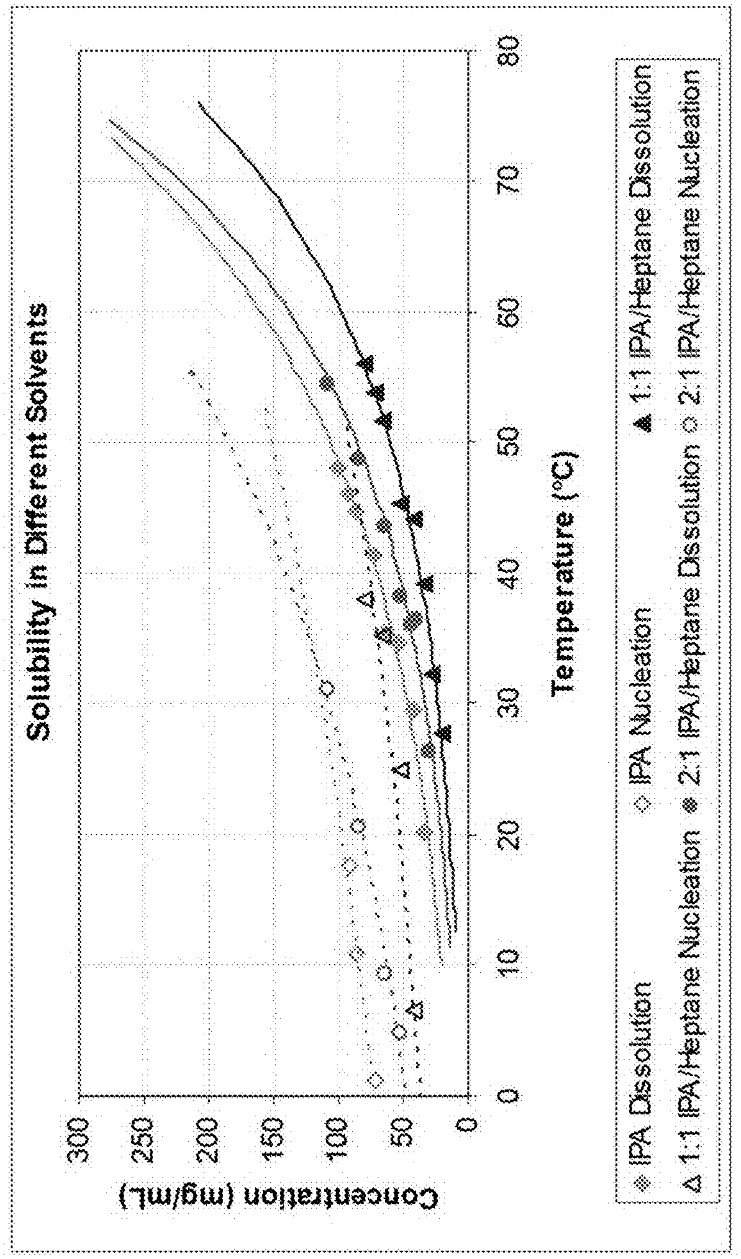
FIG. 11 is a graph showing the solubility of Solid Form A as a function of temperature in different solvents.

Slurries under the two IPA:heptane ratios were carried out at 40 °C, room temperature and 4 °C, and yielded Solid Form A. Crystallizations from ethyl acetate and isopropyl acetate were also successful at a smaller scale. Additional solvent mixes were tested. See FIG. 11.

An Atlas instrument was set up with overhead stirring, temperature probe, inlet port for heptane and a condenser. 100 ml of tetrahydrofuran (200 mL, 2457 mmol) was measured into the vessel. Compound X (39.9961 g, 101.1 mmol) was weighed by difference into the vessel, and the remaining 100 ml of tetrahydrofuran (200 mL, 2457 mmol) was added.

Reaction temperature control was used throughout, and the stirring was set at 200 rpm. The vessel was set to heat to 30 °C from 20 °C at 1 °C/min. It was held for a few minutes (Compound X was observed to have dissolved). It was then cooled at 1 °C/min to 20 °C. Once the temperature had reached 20.4 °C, Solid Form A seed (0.4093 g, 1.035 mmol) was added. A slurry was produced and retained after a couple of minutes. The syringe pump was then set to dose heptane (500 mL, 3413.2 mmol) over 60 minutes. The vessel was set to hold the reaction temperature at 20 °C overnight.

Crystallization had occurred in the vessel. It was noted that the top couple of centimeters of liquid had far fewer crystals than below, indicating large particles had formed. A sample was taken using a pipette for microscopy. The vessel was stopped, and the reaction mixture drained from the bottom of the vessel. Due to the large crystal size, Compound X settled almost immediately after the stirring was stopped. The material in the drainage beaker was filtered under vacuum, and then the liquors were poured back into the crystallization vessel. The crystallization vessel was turned back on at 20 °C with stirring, and once the crystals were resuspended, the reaction mixture was drained with the stirrer left on. This material was subsequently filtered under vacuum. The filtrate was used to flush the beaker into the filter, and then recycled again in the same way. The solid was left filtering under vacuum for around 30 minutes.

The solid was transferred into a pre-tared crystallization dish, which was placed in a vacuum oven at 50 °C with a slow air bleed for 4 hours.

All isolated crystals were analyzed by XRPD with method described below:

Powder was placed on a silicon wafer lightly coated with silicone grease, and pressed with a microscope slide. The sample was run on the Bruker D4 Endeavour diffractometer using method 1VAN 2-55 (10 mins). 1VAN 2-55 (10 mins) method: the diffraction pattern was measured from 2-55°2-theta, with a step size of 0.018° and a step time of 0.20 seconds.

Alternatively, Solid Form A were prepared by the following method:

Approximately 80-100 mg of Compound X was placed in 21 HPLC vials. 5 ml of water/1-butanol and IPA/heptane mixes were prepared at various ratios. 0.7 ml of the water/1-butanol or IPA/heptane mixes was added to each of the vials. These were then mixed on the whirlymixer and allowed to stand. More Compound X was added to the solvent systems that dissolve all Compound X, such as solvent systems comprising toluene.

All water/1-butanol solvent systems completely dissolved Compound X. Additional Compound X was added to the vials and dissolved.

All vials were sealed and set down at the various temperatures on roller mixers.

The slurries were taken off the stirrer blocks and analyzed wet using the XRPD method described herein. The solid phase of the slurries was then isolated using a 0.2 μm centrifuge filter spun at 13,200 rpm for at least 10 minutes.

All isolated slurries were analyzed by XRPD dry.

Wet XRPD method: a small portion of slurry was pipetted onto a silicon wafer and covered with Kapton film. The sample was run on the Bruker D4 Endeavour diffractometer using method IVAN 2-40 (5 mins). 1VAN 2-40 method: the diffraction pattern was measured from 2-40°2-theta, with a step size of 0.018° and a step time of 0.15 seconds.

Dry XRPD method: powder was placed on a silicon wafer lightly coated with silicone grease, and pressed with a microscope slide. The sample was run on the Bruker D4 Endeavour diffractometer using method 1VAN 2-55 (10 mins). 1VAN 2-55 method: the diffraction pattern was measured from 2-55°2-theta, with a step size of 0.018° and a step time of 0.20 seconds.

Solid State Properties of Solid Form A

Solid Form A is a highly crystalline and non-hygroscopic with high melting point and high aqueous and organic solubility. It is demonstrated to be chemically and physically stable.

TABLE 1

Figure 1B:
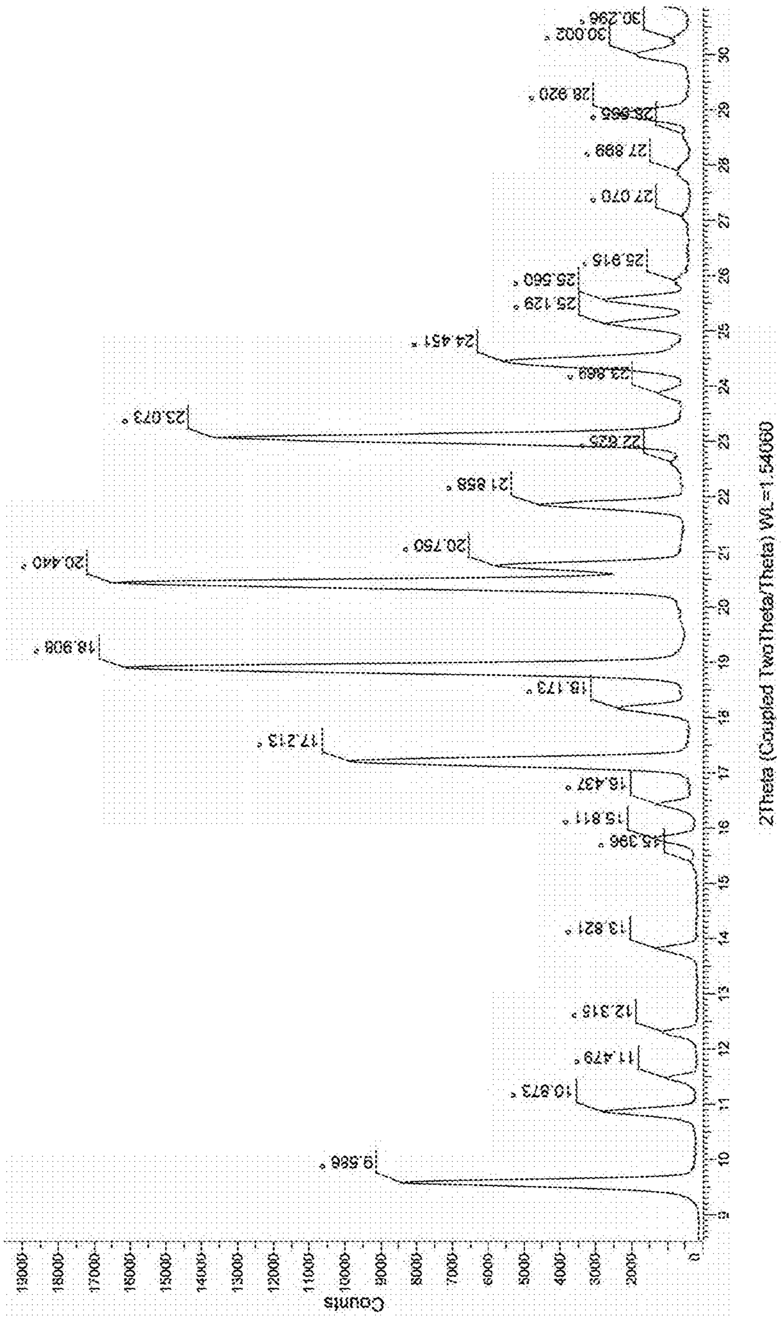
FIG. 1B is an XRPD of Solid Form A showing the entire range of angle from about 9°2θ about 30°2θ.
Figure 1C:
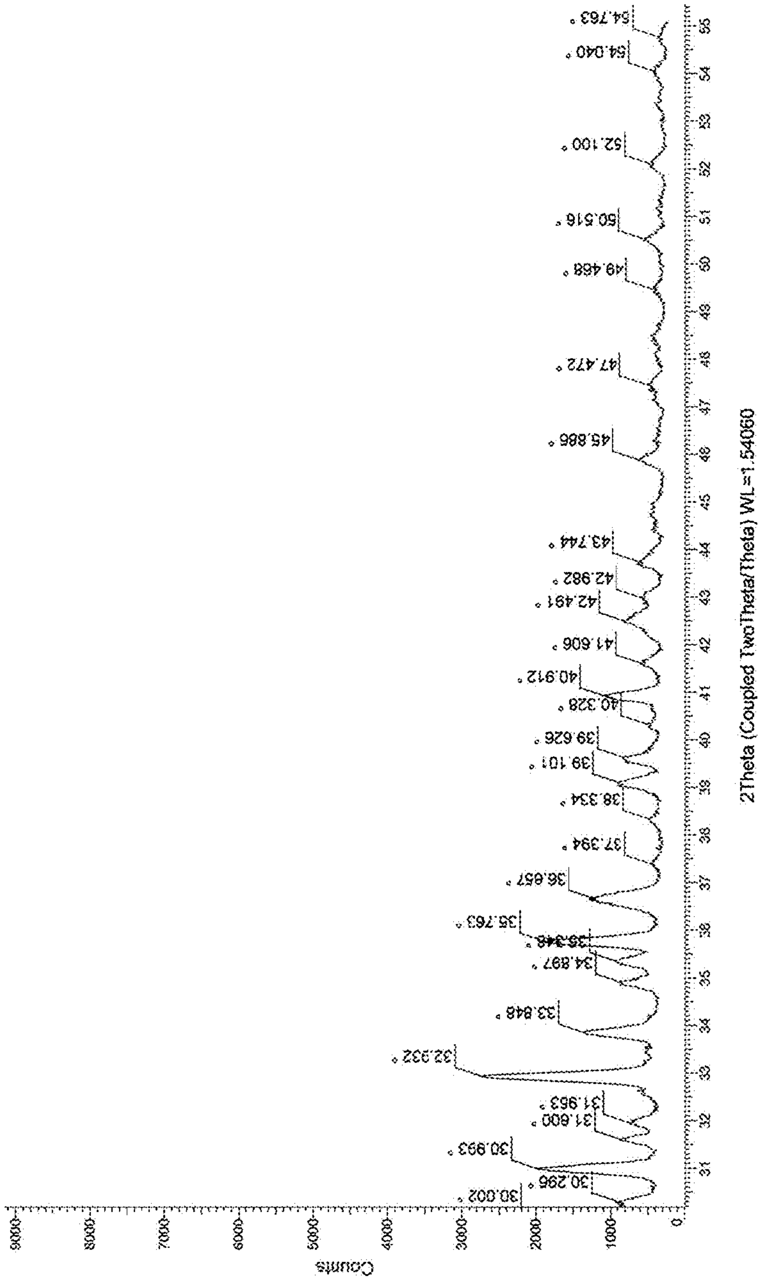
FIG. 1C is an XRPD of Solid Form A showing the entire range of angle from about 31°2θ to about 55°2θ.

| Solid State Properties of Solid Form A | |
|---|---|
| Chemical structure | 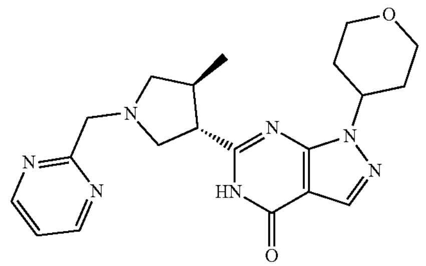 [SMILES: C[C@@H]1CN(Cc2ncccn2)C[C@H]1c1nc2c(cnn2C2CCOCC2)c(=O)[nH]1] |
| Molecular formula | $C_{20}H_{25}N_7O_2$ |
| Molecular Weight (g/mol) | 395.47 |
| Degree of Hydration/Solvation | Anhydrous |
| Form | Free base Solid Form A |
| Predicted pKa | 8.6 (acid), 7.9 (basic) ACD labs<br>9.3 (acid), 6.6 (basic) MoKa |
| True Density | 1.29 (measured), 1.279 Mg/m$^3$ (crystal structure) |
| Crystallinity | Highly crystalline (see FIG. 1A to FIG. 1C and |

TABLE 1-continued

Figure 3:
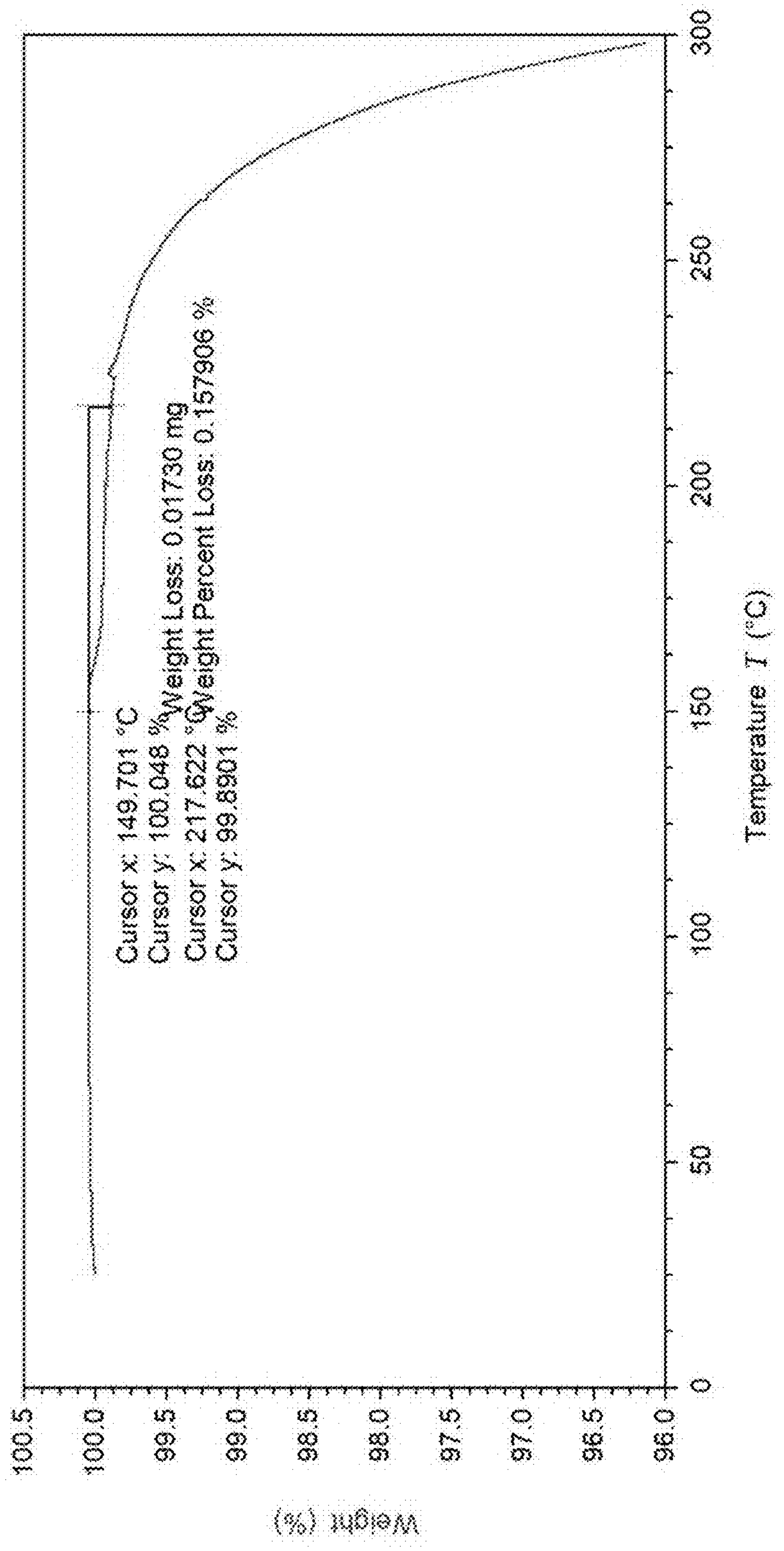
FIG. 3 is a thermal gravimetric analysis (TG) thermogram of Solid Form A.

| Solid State Properties of Solid Form A | |
|---|---|
| (XRPD & PLM) | Tables 2 and 3 below) |
| Thermal Analysis (DSC/HSM/HS-XRPD) | DSC shows a sharp melting endotherm at an onset of 161 °C (10 °C/min), which has been verified as a melt by hot stage microscopy. See FIG. 2. |
| Gravimetric Analysis (TGA/EGA) | A small loss of 0.2% is seen at the melt but the material does not appear to undergo significant degradation until approximately 240 °C See FIG. 3. |

TABLE 1-continued

Figure 4:
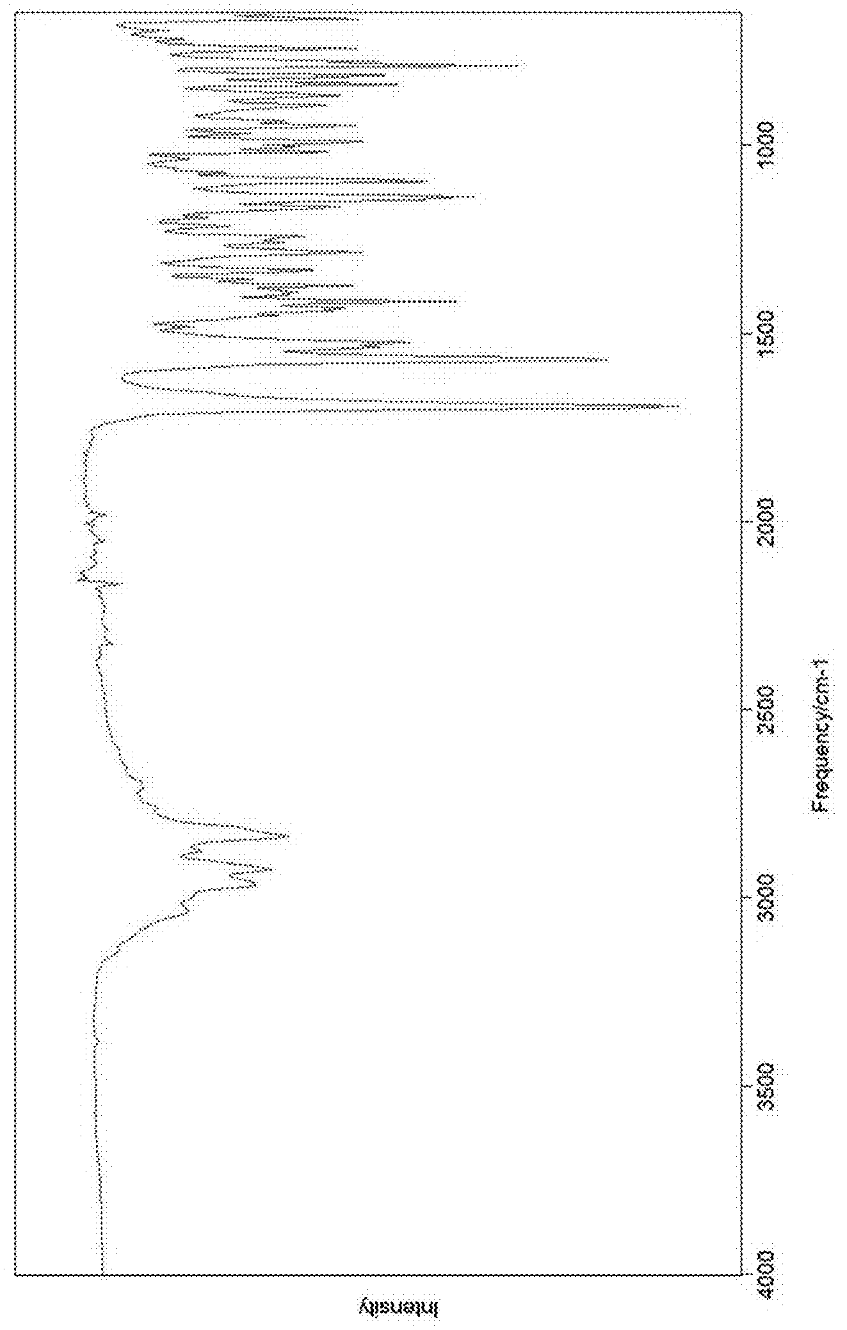
FIG. 4 is a Fourier Transform infrared spectrum of Solid Form A.
Figure 5:
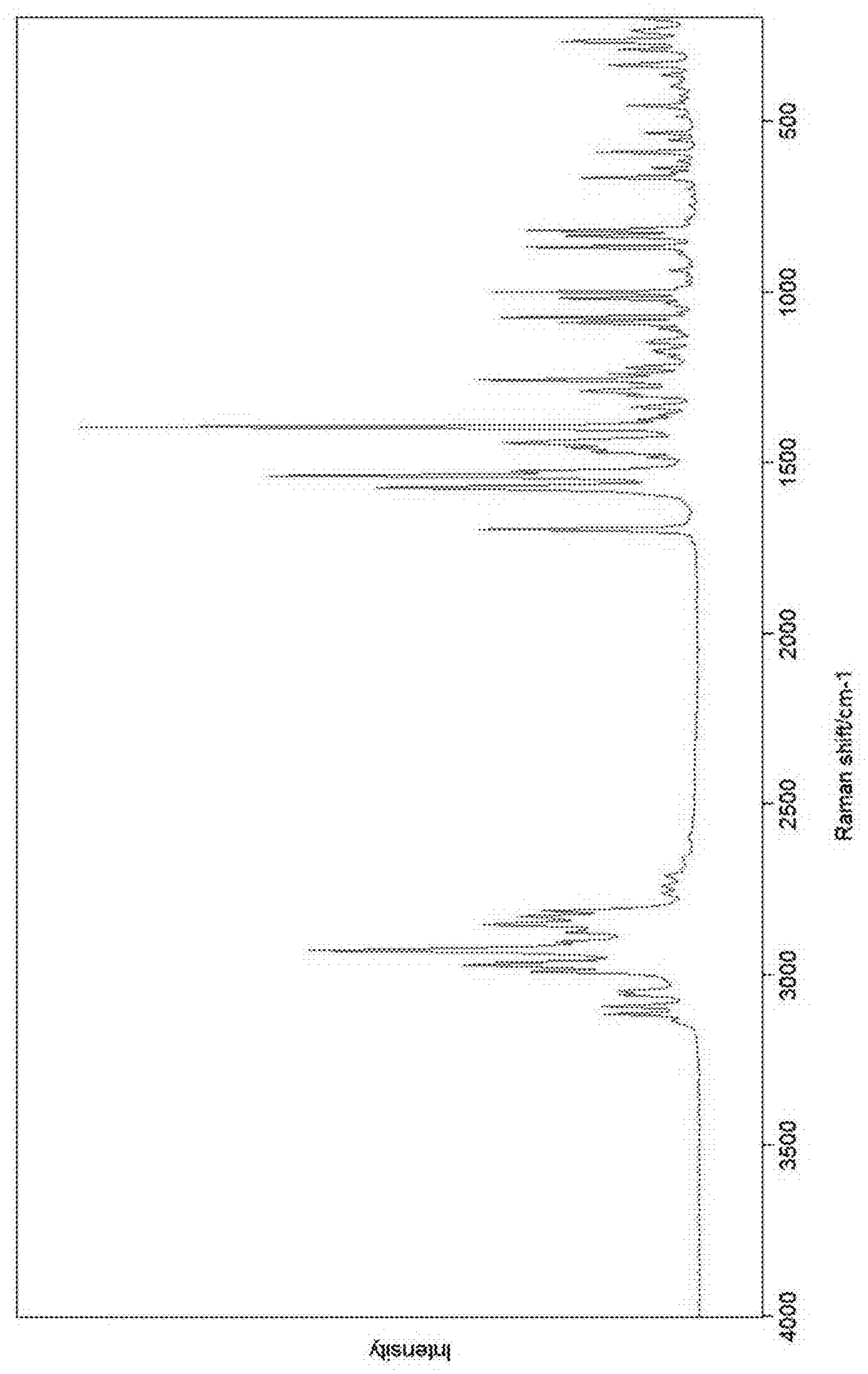
FIG. 5 is a FT-Raman spectrum of Solid Form A.
Figure 6:
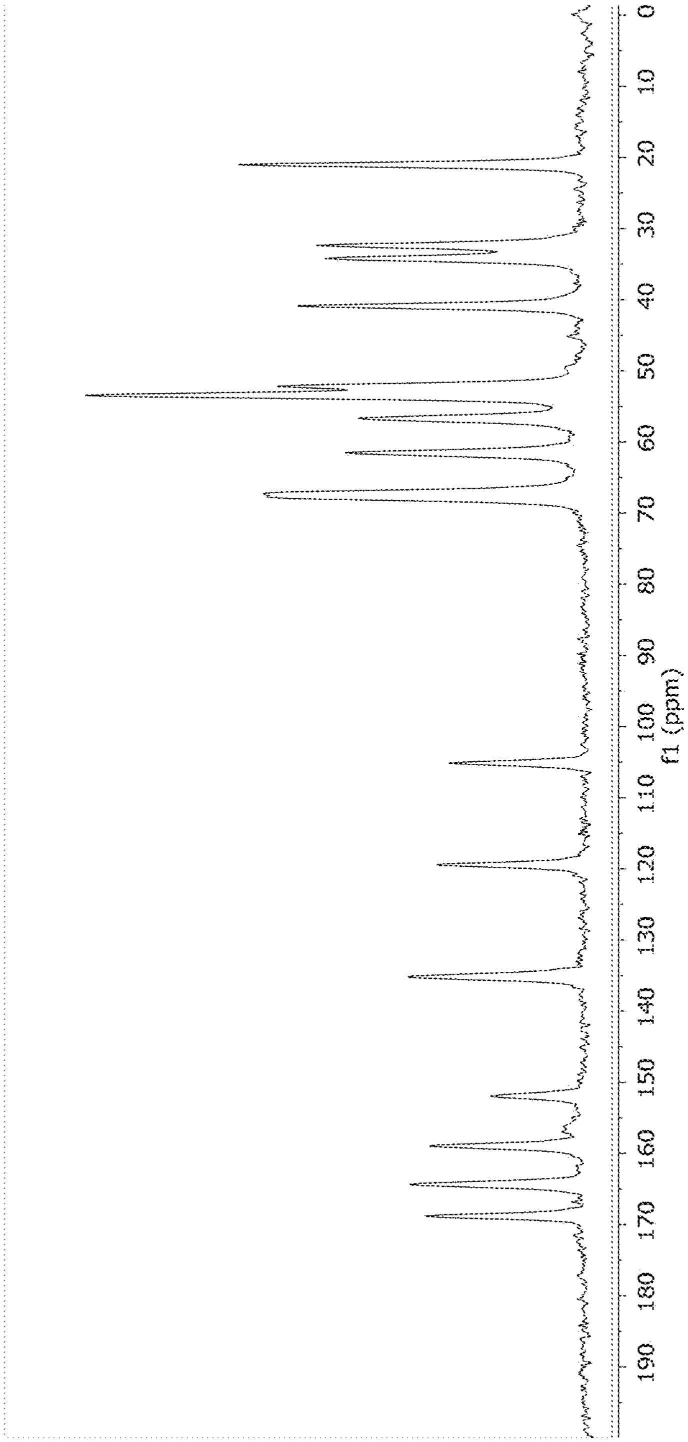
FIG. 6 is a $^{13}C$ solid state nuclear magnetic resonance spectrum of Solid Form A.

| Solid State Properties of Solid Form A | |
|---|---|
| FT-IR | A reference FT-IR spectrum for Form A has been generated. See FIG. 4. |
| Raman | A reference FT-Raman spectrum for Form A has been generated. See FIG. 5. |
| ss-NMR | A reference ssNMR spectrum for Form A has been generated. See FIG. 6. |

XRPD Data:

TABLE 2

Listing of all peak.

| Angle | d Value | Net Intensity | Gross Intensity | Rel. Intensity | Position | Intensity | FWHM |
|---|---|---|---|---|---|---|---|
| 9.585853 | 9.219097 | 8246.859 | 8391.286 | 0.518112 | 9.586 | 8391.29 | 0.1 |
| 10.87268 | 8.130696 | 2617.888 | 2796.378 | 0.16447 | 10.873 | 2796.38 | 0.1 |
| 11.47872 | 7.702747 | 867.399 | 1047.194 | 0.054495 | 11.479 | 1047.19 | 0.1 |
| 12.31546 | 7.18122 | 952.4285 | 1118.497 | 0.059837 | 12.315 | 1118.5 | 0.1 |
| 13.82144 | 6.401958 | 1127.56 | 1286.169 | 0.070839 | 13.821 | 1286.17 | 0.103 |
| 15.39587 | 5.750634 | 143.4678 | 342.5 | 0.009013 | 15.396 | 342.5 | 0.104 |
| 15.81057 | 5.600719 | 1131.498 | 1356.416 | 0.071087 | 15.811 | 1356.42 | 0.103 |
| 16.4368 | 5.38872 | 1004.237 | 1276.596 | 0.063092 | 16.437 | 1276.6 | 0.1 |
| 17.21252 | 5.147572 | 9541.77 | 9884.02 | 0.599466 | 17.213 | 9884.02 | 0.112 |
| 18.17312 | 4.877586 | 1949.411 | 2367.143 | 0.122473 | 18.173 | 2367.14 | 0.106 |
| 18.90844 | 4.689531 | 15651.76 | 16124.87 | 0.983328 | 18.908 | 16124.9 | 0.114 |
| 20.4398 | 4.341515 | 15917.13 | 16460.96 | 1 | 20.44 | 16461 | 0.113 |
| 20.7497 | 4.277367 | 5249.104 | 5799.915 | 0.329777 | 20.75 | 5799.92 | 0.111 |
| 21.8577 | 4.062981 | 4027.415 | 4595.243 | 0.253024 | 21.858 | 4595.24 | 0.1 |
| 22.62474 | 3.926939 | 325.8141 | 902.2615 | 0.020469 | 22.625 | 902.262 | 0.123 |
| 23.07301 | 3.851649 | 13064.7 | 13639.18 | 0.820795 | 23.073 | 13639.2 | 0.107 |
| 23.86868 | 3.725023 | 667.5117 | 1225.781 | 0.041937 | 23.869 | 1225.78 | 0.113 |
| 24.45101 | 3.637611 | 5029.869 | 5565.958 | 0.316004 | 24.451 | 5565.96 | 0.133 |
| 25.1292 | 3.540954 | 2223.836 | 2723.111 | 0.139713 | 25.129 | 2723.11 | 0.11 |
| 25.56037 | 3.482192 | 2272.185 | 2741.915 | 0.142751 | 25.56 | 2741.92 | 0.112 |
| 25.91479 | 3.435366 | 366.8244 | 808.6755 | 0.023046 | 25.915 | 808.676 | 0.126 |
| 27.07006 | 3.291321 | 189.3233 | 563.6555 | 0.011894 | 27.07 | 563.656 | 0.105 |
| 27.89876 | 3.195409 | 354.7881 | 731.7009 | 0.02229 | 27.899 | 731.701 | 0.163 |
| 28.56547 | 3.122327 | 169.8336 | 562.035 | 0.01067 | 28.565 | 562.035 | 0.1 |
| 28.91968 | 3.084885 | 1911.023 | 2307.066 | 0.120061 | 28.92 | 2307.07 | 0.134 |
| 30.00177 | 2.976039 | 1443.876 | 1852.407 | 0.090712 | 30.002 | 1852.41 | 0.141 |
| 30.29597 | 2.947806 | 482.5076 | 895.7156 | 0.030314 | 30.296 | 895.716 | 0.225 |
| 30.99291 | 2.883089 | 1561.515 | 1978.854 | 0.098103 | 30.993 | 1978.85 | 0.12 |
| 31.60044 | 2.829032 | 442.7048 | 855.1071 | 0.027813 | 31.6 | 855.107 | 0.106 |
| 31.95262 | 2.798649 | 339.8424 | 744.9392 | 0.021351 | 31.953 | 744.939 | 0.125 |
| 32.93155 | 2.717658 | 2330.57 | 2731.935 | 0.146419 | 32.932 | 2731.94 | 0.12 |
| 33.84793 | 2.646147 | 947.52 | 1343.216 | 0.059528 | 33.848 | 1343.22 | 0.13 |
| 34.89721 | 2.56895 | 459.0477 | 847.7753 | 0.02884 | 34.897 | 847.775 | 0.108 |
| 35.34829 | 2.537194 | 535.2233 | 926.8384 | 0.033626 | 35.348 | 926.838 | 0.205 |
| 35.76305 | 2.508713 | 1478.759 | 1868.422 | 0.092904 | 35.763 | 1868.42 | 0.118 |
| 36.65705 | 2.449557 | 834.3998 | 1204.817 | 0.052422 | 36.657 | 1204.82 | 0.182 |
| 37.3939 | 2.402963 | 112.2246 | 451.3333 | 0.007051 | 37.394 | 451.333 | 0.1 |
| 38.33442 | 2.346143 | 133.3368 | 469.9358 | 0.008377 | 38.334 | 469.936 | 0.11 |
| 39.1009 | 2.301899 | 526.5476 | 883.8 | 0.033081 | 39.101 | 883.8 | 0.136 |
| 39.62588 | 2.272604 | 455.3147 | 818.0017 | 0.028605 | 39.626 | 818.002 | 0.129 |
| 40.32828 | 2.234627 | 134.8131 | 498.8747 | 0.00847 | 40.328 | 498.875 | 0.197 |
| 40.9116 | 2.204102 | 689.4661 | 1053.856 | 0.043316 | 40.912 | 1053.86 | 0.12 |
| 41.60553 | 2.16893 | 221.3042 | 574.7 | 0.013904 | 41.606 | 574.7 | 0.116 |
| 42.49117 | 2.12575 | 449.7502 | 801.9968 | 0.028256 | 42.491 | 801.997 | 0.206 |
| 42.98194 | 2.102608 | 215.4958 | 568.245 | 0.013539 | 42.982 | 568.245 | 0.1 |
| 43.74369 | 2.067743 | 272.3291 | 619.9115 | 0.017109 | 43.744 | 619.912 | 0.147 |
| 45.88631 | 1.976052 | 317.1079 | 623.7383 | 0.019922 | 45.886 | 623.738 | 0.135 |
| 47.47183 | 1.913686 | 212.4046 | 519.6244 | 0.013344 | 47.472 | 519.624 | 0.181 |
| 49.46794 | 1.841036 | 135.6586 | 430.0683 | 0.008523 | 49.468 | 430.068 | 0.132 |
| 50.51641 | 1.805257 | 230.8508 | 530.6319 | 0.014503 | 50.516 | 530.632 | 0.118 |
| 52.10043 | 1.754036 | 172.4654 | 446.7572 | 0.010835 | 52.1 | 446.757 | 0.172 |
| 54.03993 | 1.695572 | 128.5778 | 396.5395 | 0.008078 | 54.04 | 396.54 | 0.192 |
| 54.76259 | 1.674893 | 81.31308 | 339.6681 | 0.005109 | 54.763 | 339.668 | 0.102 |

TABLE 3

| Listing of peaks with an intensity greater than 5 percent of the intensity of the peak at 20.4° two-theta | |
|---|---|
| Angle (°2-theta) | Relative intensity (%) |
| 9.6 | 51.8 |
| 10.9 | 16.4 |
| 11.5 | 5.4 |
| 12.3 | 6 |
| 13.8 | 7.1 |
| 15.8 | 7.1 |
| 16.4 | 6.3 |
| 17.2 | 59.9 |
| 18.2 | 12.2 |
| 18.9 | 98.3 |
| 20.4 | 100 |
| 20.7 | 33 |
| 21.9 | 25.3 |
| 23.1 | 82.1 |
| 24.5 | 31.6 |
| 25.1 | 14 |
| 25.6 | 14.3 |
| 28.9 | 12 |
| 30 | 9.1 |
| 31 | 9.8 |
| 32.9 | 14.6 |
| 33.8 | 6 |
| 35.8 | 9.3 |
| 36.7 | 5.2 |

Figure 8:
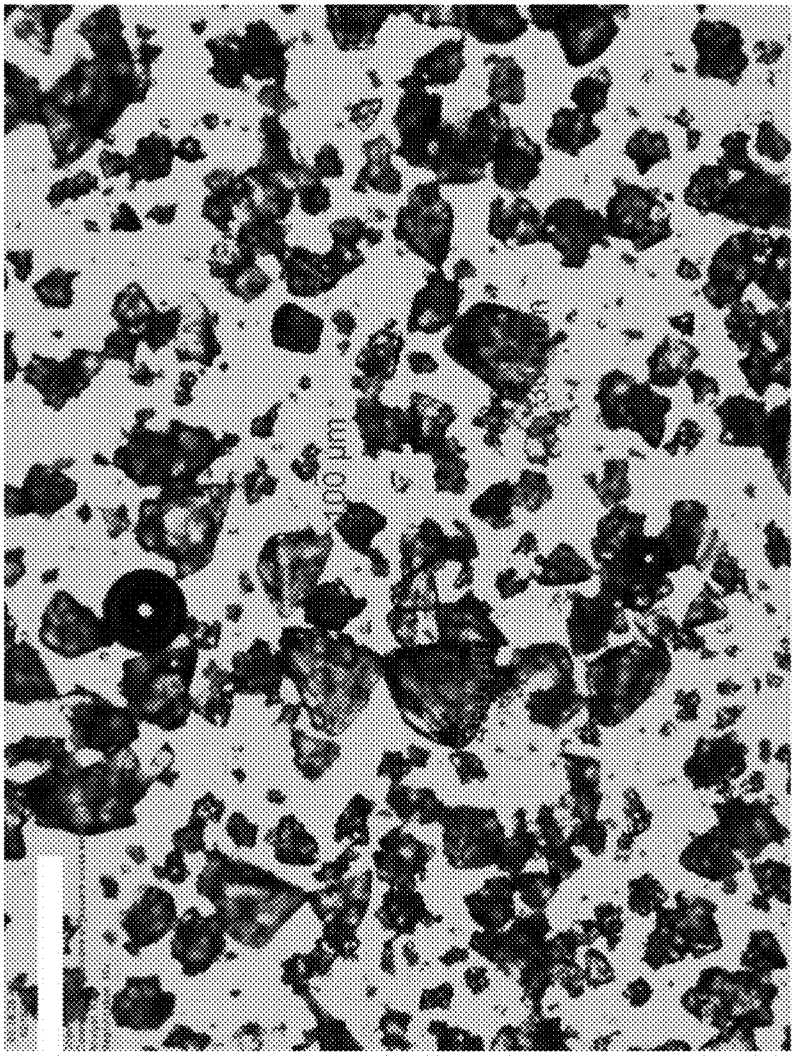
FIG. 8 is a photomicrograph of Solid Form A (unmilled) 40× magnification.
Figure 10:
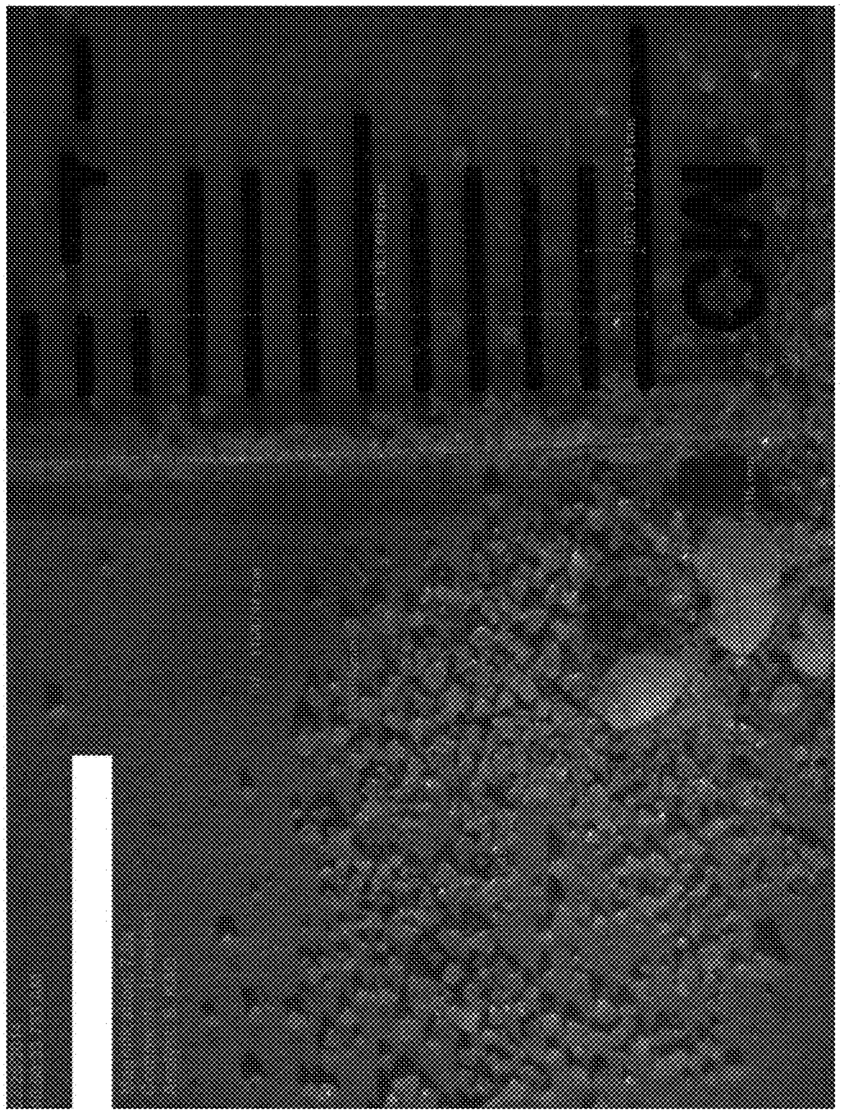
FIG. 10 is a photomicrograph of Solid Form A (unmilled) 7× magnification.

Solid Form A displays tetrahedral almost equant morphology observed from crystallization (see FIG. 8 and FIG. 10).

Water Sorption

Figure 7:
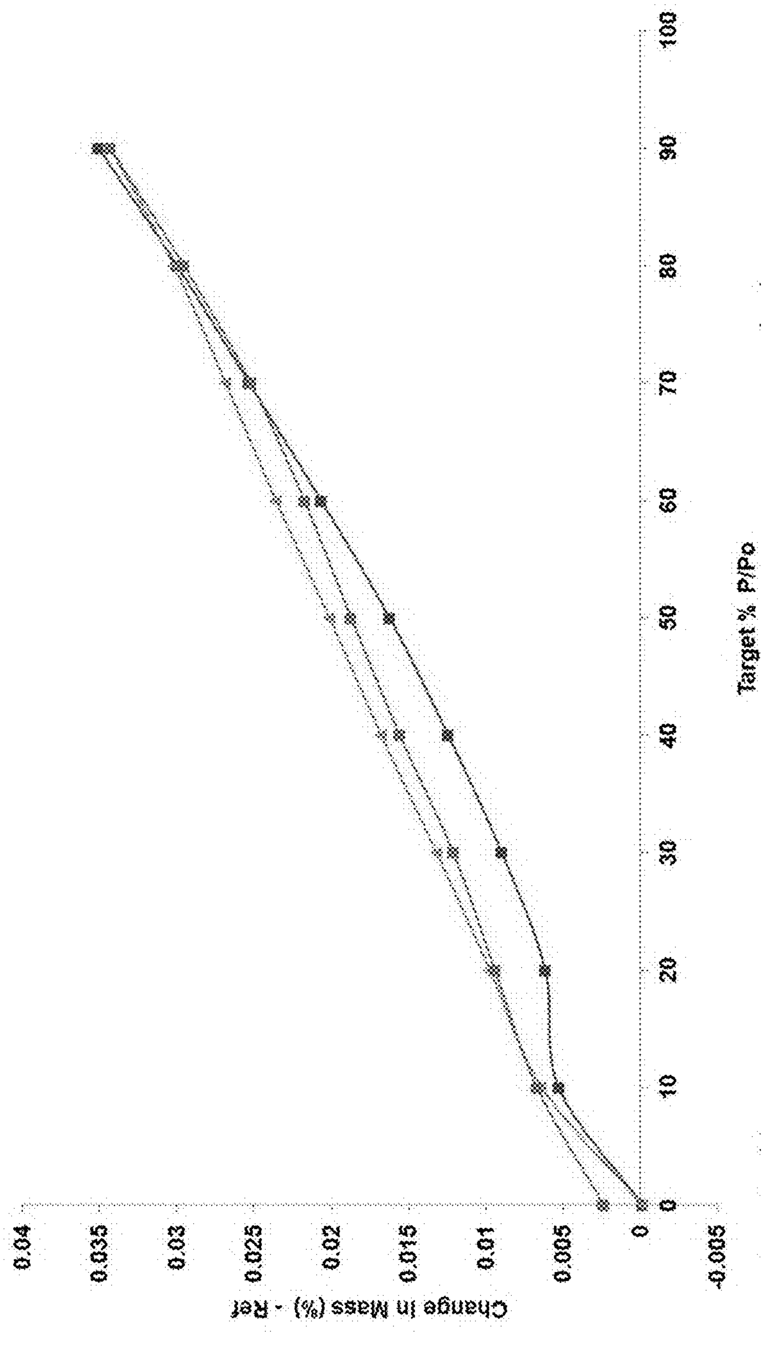
FIG. 7 is a dynamic vapor sorption isotherm plot for Solid Form A.

Solid Form A is non-hygroscopic, absorbing less than 0.05% water at 90% RH, 25 °C The uptake at various humidities is given in the Table 4 below at 25 °C. See FIG. 7 for the isotherm plot.

TABLE 4

| Water uptake of Solid Form A at various humidities | | |
|---|---|---|
| Humidity | Water Content (% w/w) | |
| (% RH) | Sorption | Desorption |
| 0 | 0 | 0 |
| 10 | 0.01 | 0.01 |
| 20 | 0.01 | 0.01 |
| 30 | 0.01 | 0.01 |
| 40 | 0.02 | 0.02 |
| 50 | 0.02 | 0.02 |
| 60 | 0.02 | 0.02 |
| 70 | 0.03 | 0.03 |
| 80 | 0.03 | 0.03 |

Solid Form A is non-hygroscopic. Solid Form A was analyzed prior to milling and showed a very similar sorption profile. The low hygroscopicity indicates that the Solid Form A does not require any special storage conditions.

Aqueous Solubility

Solubility of Solid Form A is high across a wide range of solvent conditions. Solid Form A is very water soluble across a range of biologically relevant pH conditions as shown below.

TABLE 5

| Solubility of Solid Form A in a range of biologically relevant pH conditions at 25 °C | | | |
|---|---|---|---|
| Buffer/Media | pH (n = x) | Solubility (μg/mL) (n = x) (SD) | Solid Form/ Salt (post test) |
| 0.01M HCl | 1.7 (n = 2) | >56,600 (n = 2) | No solid |
| 100 mM Succinate buffer | 4.0 (n = 2) | >58,600 (n = 2) | No solid |
| 100 mM Citrate buffer | 4.5 (n = 2) | >55,900 (n = 2) | No solid |
| 100 mM Succinate buffer | 5.5 (n = 2) | >52,800 (n = 2) | No solid |
| 100 mM Citrate buffer | 6.0 (n = 2) | >52,200 (n = 2) | No solid |
| 100 mM Phosphate buffer | 6.5 (n = 2) | >53,300 (n = 2) | No solid |
| Phosphate buffered saline | 7.0 (n = 1) | 42,100 (n = 1) | Solid Form A |
| Phosphate buffered saline | 7.4 (n = 1) | 27,600 (n = 1) | Solid Form A |

Solubility of Solid Form a of Compound X and Amorphous Compound X in Various Solvents

TABLE 6

| Solubility of Solid Form A and amorphous Compound X in various solvents at room temperature. | | | |
|---|---|---|---|
| Entry | Solvent | Solubility (mg/ml) | Solubility (mmol) |
| Solid Form A | | | |
| 1 | 1,2-Xylene | >65.4 | >165 |
| 2 | Acetone | 49.4 | 125 |
| 3 | MeCN | 47.8 | 121 |
| 4 | Chloroform | >57.5 | >145 |
| 5 | Glyme | >63 | >159 |
| 6 | Dioxane | >46.3 | >117 |
| 7 | EtOAc | 44.7 | 113 |
| 8 | EtOH | 63.4 | 160 |
| 9 | H2O-acetone | >33.3 | >84 |
| 10 | H2O—MeCN | >27 | >68 |
| 11 | H2O—EtOH | >29.8 | >75 |
| 12 | H2O—MeOH | >34.2 | >87 |
| 13 | H2O | 35.3 | 89 |
| 14 | Heptane | 0.6 | 1 |
| 15 | IPA | 29.2 | 74 |
| 16 | MeOH | >71.4 | >181 |
| 17 | Methoxyethanol | >74.5 | >188 |
| 18 | MTBE | 6.7 | 17 |
| 19 | Nitromethane | >74.9 | >189 |
| 20 | THF | >58 | >147 |
| 21 | Toluene | 52.2 | 132 |
| Amorphous Solubility | | | |
| 1 | 1,2-Xylene | 19.9 | 50 |
| 2 | Acetone | >79.7 | >202 |
| 3 | MeCN | >117.3 | >297 |
| 4 | Chloroform | >92.3 | >233 |
| 5 | 1,2-Dimethoxyethane | >113.2 | >286 |
| 6 | Dioxane | 27.9 | 71 |
| 7 | EtOAc | 20.6 | 52 |
| 8 | EtOH | >98.6 | >249 |
| 9 | Heptane | 0.7 | 2 |
| 10 | IPA | >85.9 | >217 |
| 11 | MeOH | >90.2 | >228 |
| 12 | MTBE | 11.2 | 28 |
| 13 | Nitromethane | >70.2 | >178 |
| 14 | THF | 81.5 | 206 |
| 15 | Toluene | 18.3 | 46 |
| 16 | Water/acetone | >130.3 | >329 |
| 17 | Water/MeCN | >75.6 | >191 |
| 18 | Water/EtOH | >26.8 | >68 |

TABLE 6-continued

Solubility of Solid Form A and amorphous Compound X in various solvents at room temperature.

| Entry | Solvent | Solubility (mg/ml) | Solubility (mmol) |
|---|---|---|---|
| 19 | Water/MeOH | >42.5 | >107 |
| 20 | Water | 64.8 | 164 |

Organic Solubility

TABLE 7

Selected gravimetric (TGA) solubility results at 25 °C

| Solvent | Solubility (mg/mL) | Solubility (mmol) |
|---|---|---|
| Acetone | 49.4 | 125 |
| MeCN | 47.8 | 121 |
| EtOAc | 44.7 | 113 |
| EtOH | 63.4 | 160 |
| $H_2O$ | 35.3 | 89 |
| Heptane | 0.6 | 1 |
| IPA | 29.2 | 74 |
| MTBE | 6.7 | 17 |
| Toluene | 52.2 | 132 |

Particle Properties of Solid Forma

The particle properties are summarized below.

Particle Shape

Figure 9:
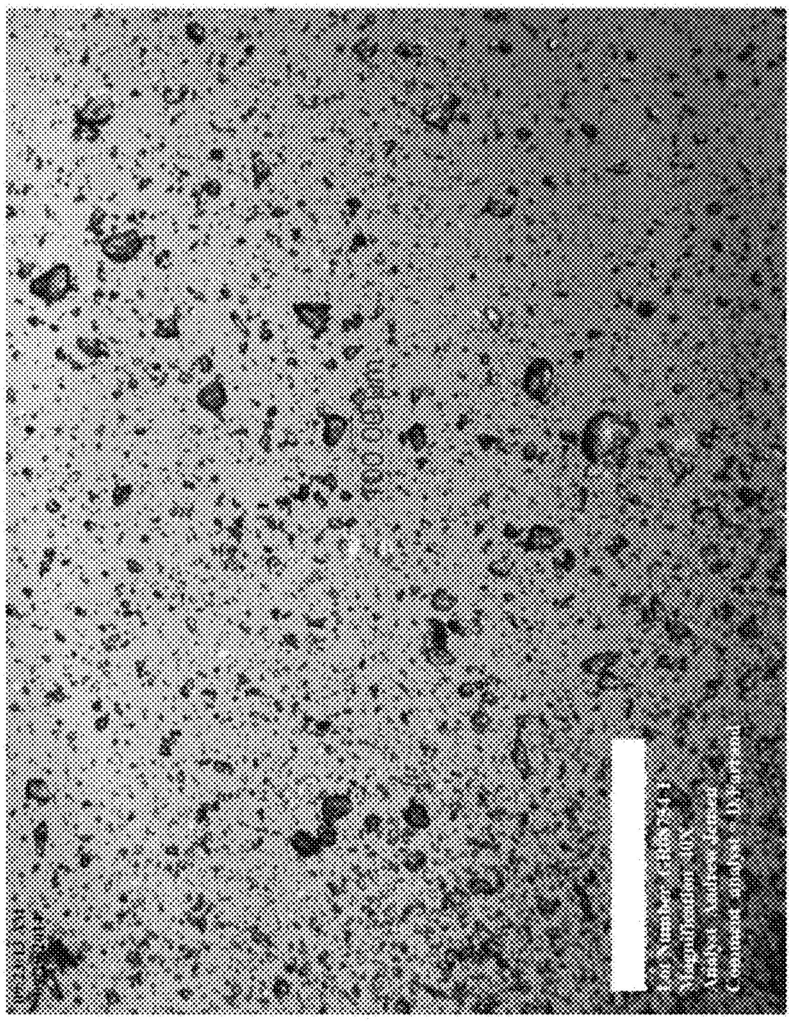
FIG. 9 is a photomicrograph of Solid Form A (milled) 40× magnification.

Unmilled, the primary particles are equant irregular or tetrahedral particles as shown in FIG. 8. The particles described were subsequently milled. They appear to remain irregularly shaped as shown in FIG. 9.

Particle Size

Primary particles from below 100 μm to around 500 μm in size, with soft agglomerates up to several millimeters, were observed. The D[4,3] of this material was 195 μm. This material was subsequently milled, to give far fewer large particles and an overall much smaller average primary particle size, giving a D[4,3] of 49.5 μm. See Table 8 for a comparison of particle size properties of various batches.

TABLE 8

Particle size data for measurements of various batches of Solid Form A. A3-A8 and A10 were milled, other lots were unmilled. A3, A4, A5, and A6-A8 were milled from A2, and A10 was milled from A9.

| Batch | D[v, 0.1] | D[v, 0.9] | D[4, 3] |
|---|---|---|---|
| A2 | 45.6 | 247 | 144 |
| A3 | 10.5 | 126 | 60.2 |
| A4 | 4.39 | 52.5 | 24.1 |
| A5 | 6.86 | 197 | 89.2 |
| A6* | 5.89 | 179 | 78.6 |
| A7* | 6.17 | 191 | 85.1 |
| A8 | 3.96 | 118 | 48.6 |
| A9 | 20.6 | 362 | 195 |
| A10 | 3.29 | 129 | 49.5 |

*A6 and A7 are different measurements of the same batch.

Mechanical Properties

TABLE 9

Mechanical properties for various batches of Solid Form A. A2 and A9 were unmilled. Lots A3 and A6/A7 were milled.

| | Lot number | | | | | | | |
|---|---|---|---|---|---|---|---|---|
| | A2 | | A9 | | A3 | | A6/A7* | |
| | Value | Rating | Value | Rating | Value | Rating | Value | Rating |
| Mechanical properties | | | | | | | | |
| Compression stress (MPa) | 58.8 | Moderate | 52.5 | Moderate | 67.9 | Moderate | 56.3 | Moderate |
| Solid fraction | 0.87 | | 0.85 | | 0.857 | | 0.85 | |
| Dynamic indentation hardness (MPa) [ductility rating] | | | 63.6 | High | | | 41.6 | Very high |
| Quasistatic Hardness | | | | | | | | |
| Tensile strength (MPa) | 0.3 | Low | 0.255 | Very low | 0.624 | Moderate | 0.41 | Low |
| Compromised Tensile strength (MPa) | 0.274 | | 0.302 | | 0.488 | | 0.393 | |
| Brittle fracture index | 0.0486 | Low | −0.077 | Very low | 0.139 | Low | 0.022 | Low |
| Worst case bonding index (×102) | | | 0.401 | Moderate | | | | |
| Brittle/viscoelastic bonding index (×105) | 2.61 | Poor | 1.95 | Poor | 8.44 | Marginal | 5.3 | Poor |
| Physical properties | | | | | | | | |
| True density (g/cm3) | 1.28 | | 1.29 | | 1.29 | | 1.29 | |

*A6 and A7 are different measurements of the same batch.

Chemical & Physical Stability of Solid Forma

Chemical Stability (Including Excipient Compatibility)

Real-time stability data for unmilled Solid Form A showed Solid Form A to be chemically and physically stable through 6 months for 40 °C/75% RH as accelerated conditions and through 84 months at room temperature conditions (63 months @ 15-30 °C and 21 Months at 25 °C/60% RH) in bulk packaging (double polyethylene bags in a fiberboard drum). A photostability study was completed under ICH conditions. 70 °C/75% RH storage of milled Solid Form A for 1 week revealed no change in stability.

Clinical stability data for tablets of Solid Form A in foil/foil blisters or HDPE bottle/induction seal (IS) with desiccant showed that through 60 months at 25 °C/60% RH and 6 months at 5 °C/60% RH and 40 °C/75% RH. No significant change/trends in assay, degradation products, or disintegration were observed.

Physical Stability (to Compression, Grinding, Milling, Micronization, Etc.)

Samples of Solid Form A were milled to reduce particle size. No impact upon polymorphic form was observed.

Milled samples of Solid Form A were remilled, and exposed at 40 °C/75% RH. There was no sign of form change and no sign of a decrease in crystallinity from the XRPD.

Example 2. Solid Form B

Preparation of Solid Form B

The following methods were used for the preparation of Solid Form B:

Method 1

1. 100 mg of amorphous Compound X was dissolved in 10 mL of water at room temperature.
2. The solution was frozen and lyophilized at −85 °C
3. Deionized water was added to the lyophilized material in 100 μL aliquots.
4. Dissolution was noted after the first addition.
5. After ca. 30 seconds a pale-yellow precipitate was observed.
6. An additional 800 μL of water was added to form a mobile slurry
7. The slurry was temperature cycled between 25 and 5 °C with a 0.1 °C/min ramp rate and a 1 hour hold at 25 and 5 °C with stirring.
8. After ca. 24 hours an aliquot of the slurry was collected using a plastic pipette and the solid analyzed by XRPD.
9. The bulk material was isolated via centrifugation and the isolated solid was dried at ambient temperature in vacuo for ca. 24 hours.
10. The dried solid was re-analyzed by XRPD.
11. VT-XRPD and DVS with post DVS XRPD analysis was conducted.

Method 2

1. 1 g of amorphous compound X was weighed and transferred to a 100 mL Duran flask.
2. 40 mL of de-ionized water was added and the vessel was agitated for 5 minutes, until complete dissolution was observed.
3. The flask was placed in the chamber of a freeze dryer at ca. −90 °C for 2 hours.
4. After 2 hours the sample was moved to the desiccator and lyophilization was commenced.
5. After 72 hours the sample was removed from lyophilization.
6. 500 μL of de-ionized water was added to 500 mg of the lyophilized material, with full dissolution upon addition.
7. After a few of minutes, a precipitate appeared.
8. Additional 500 μL aliquots of de-ionized water were added until dissolution was observed, for a total of 4.5 mL of water.
9. The experiment was placed in a temperature-controlled block and temperature cycled according to the following method:
   25 °C hold for 1 h,
   Ramp to 5 °C at 0.1 °C/min
   5 °C hold for 1 h,
   Ramp to 25 °C at 0.1 °C/min
10. After 24 hours, the experiment was a pale-yellow slurry.
11. An aliquot was taken, and the solids were isolated by centrifugation.
12. The solids were analyzed by XRPD.
13. The slurry was filtered via Buchner filtration and the wet solids collected and dried at room temperature under vacuum.
14. After 24 hours the samples were removed from the oven and the dried solids weighed.
15. A small amount of material was transferred to 40 °C/75% RH chamber for 5 days.
16. After 5 days, XRPD analysis was carried out.
17. The remaining material was exposed to 40 °C/75% RH for 72 hours, monitoring conversion every 24 hours.
18. Solid Form B was characterized by PLM, TG/DSC, DSC, DVS with post DVS XRPD, FT-IR, KF, and HPLC.

Method 3

1. 1 g of amorphous compound X was weighed and transferred to a 100 mL Duran flask.
2. 40 mL of de-ionized water was added and the vessel was agitated for 5 minutes, until complete dissolution was observed.
3. The flask was placed in the chamber of a freeze dryer at ca. −90 °C for 2 hours.
4. After 2 hours the sample was moved to the desiccator and lyophilization was commenced.
5. After 72 hours the sample was removed from lyophilization.
6. The material was split into two samples. 500 μL of de-ionized water was added to 500 mg of the lyophilized material, with full dissolution upon addition.
7. After a couple of minutes, a precipitate appeared.
8. Additional 500 μL aliquots of de-ionized water were added until dissolution was observed, for a total of 4.5 mL of water each.
9. The experiments were placed in a temperature-controlled block and temperature cycled according to the following method:
   25 °C hold for 1 h,
   Ramp to 5 °C at 0.1 °C/min,
   5 °C hold for 1 h,
   Ramp to 25 °C at 0.1 °C/min,
10. After 24 hours, the experiment was a pale-yellow slurry.
11. The slurries were filtered via Buchner filtration and the wet solids collected and dried at 40 °C for 72 h.
12. The solids were analyzed by XRPD.

VT-XRPD Analysis of Solid Form B

Solid Form B was analyzed by VT-XRPD to assess changes in form upon heating.

The sample was heated at 10 °C/min and diffraction pattern collected at various temperatures (based on TG/DSC data).

The experimental details are summarized in Table 10 below

TABLE 10

Experimental Details of VT-XRPD Analysis of Solid Form B

| Temperature (°C) | Hold (mins) | XRPD |
|---|---|---|
| 30 | 0 | Solid Form B |
| 85 | 0 | Solid Form C |
| 85 | 5 | Solid Form C |
| 130 | 0 | Solid Form A/C |
| 135 | 0 | Solid Form A |
| 135 | 10 | Solid Form A |
| 30 | 0 | Solid Form A |

Figure 13:
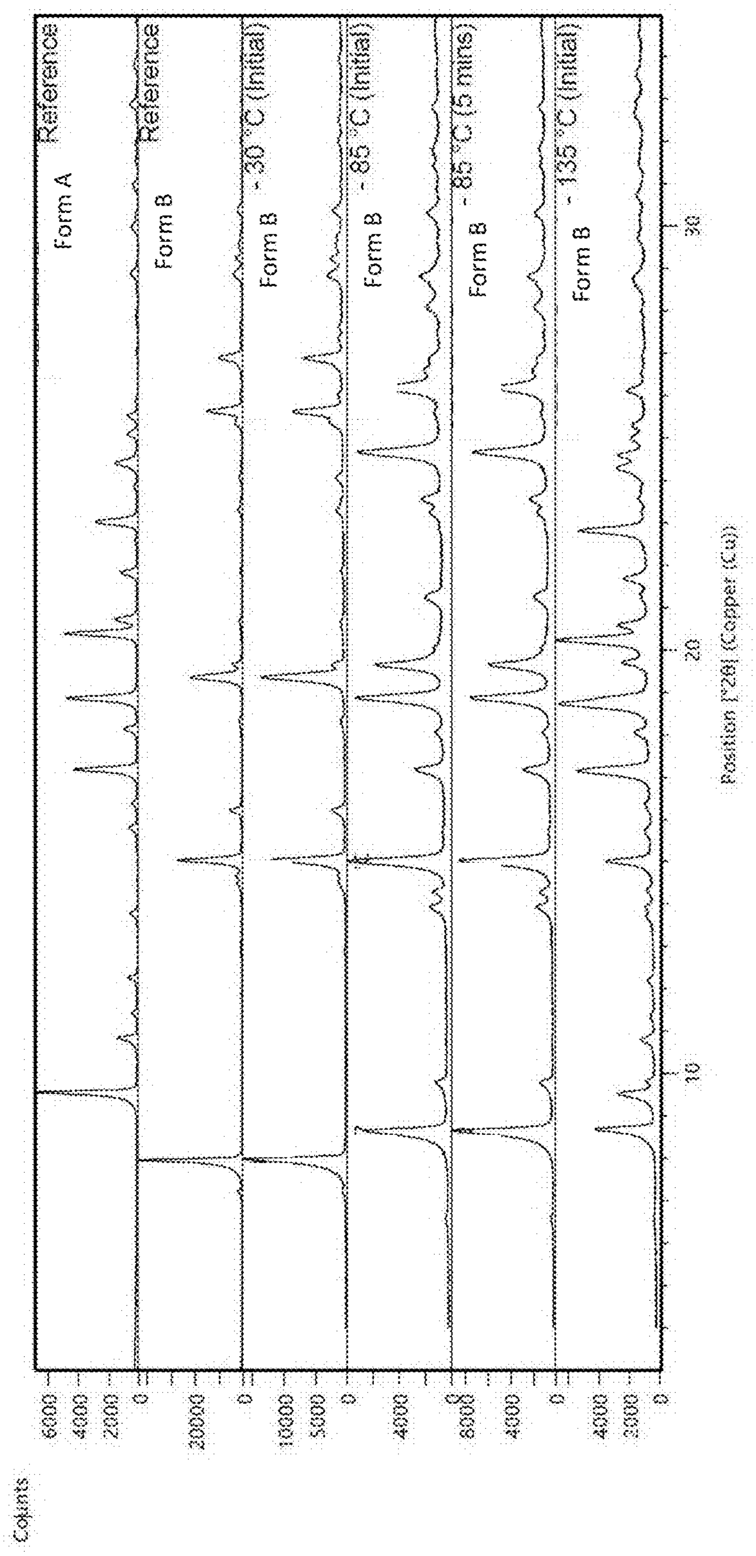
FIG. 13 is a series of VT-XRPD of Solid Form B showing the range of angle from 0°2θ to 35°2θ.
Figure 14:
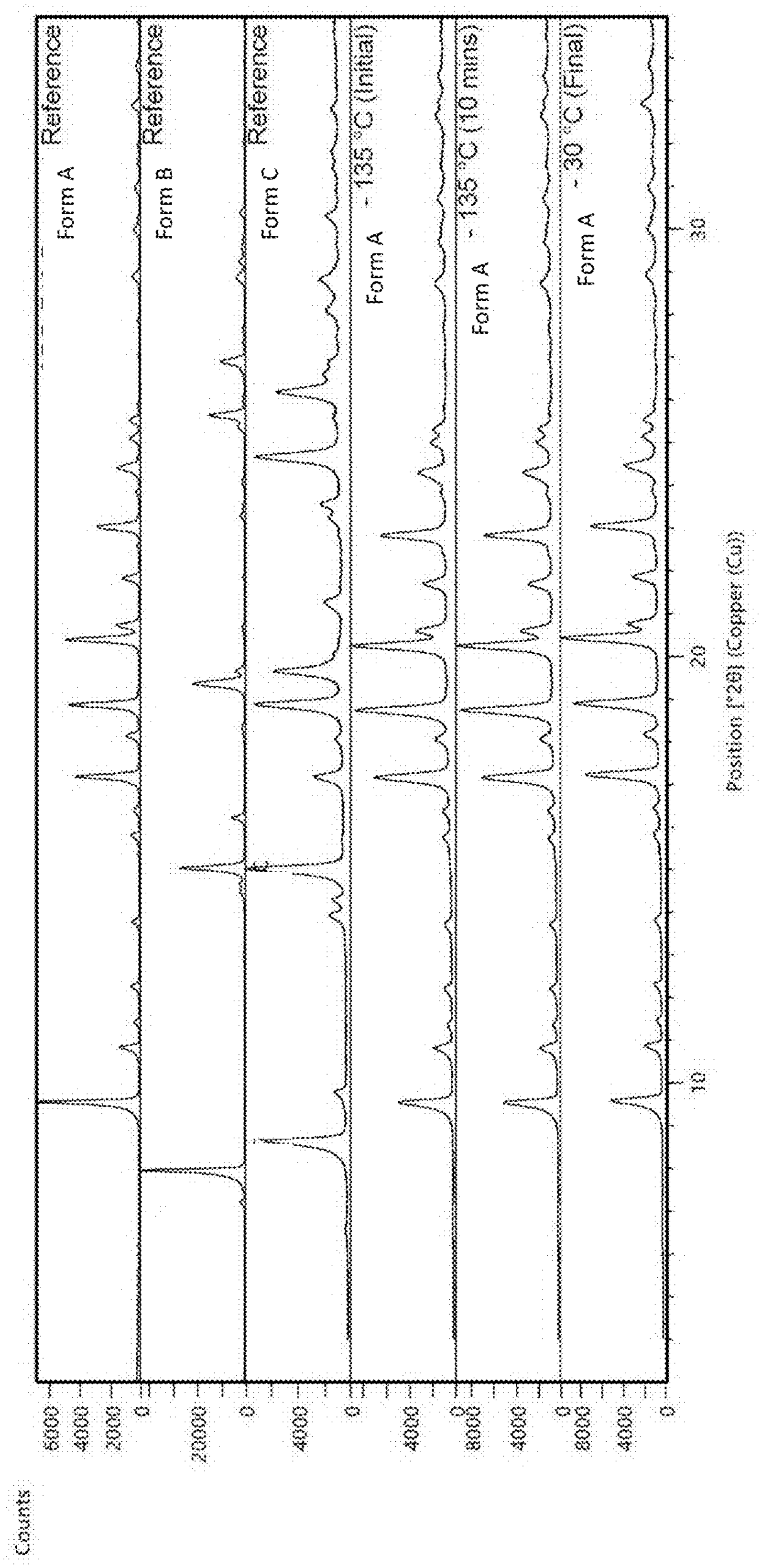
FIG. 14 is a series of VT-XRPD of Solid Form B showing the range of angle from 0°2θ to 35°2θ.

VT-XRPD showed that upon heating to 85 °C (beyond the dehydration), a new solid form, Solid Form C, was observed. At 130 °C (beyond potential solid-solid transition) the material appeared as a mixture of Solid Form A and C. After further heating to 135 °C the material was consistent with Solid Form A. The results are shown in FIG. 13 and FIG. 14.

TABLE 11

XRPD Peak List of Solid Form B

| No. | Pos. [°2θ] | d-spacing [Å] | Height [cts] | Rel. Int. [%] |
|---|---|---|---|---|
| 1 | 7.2224 | 12.2399 | 2028.70 | 4.67 |
| 2 | 7.9617 | 11.1050 | 43443.64 | 100.00 |
| 3 | 12.9094 | 6.8578 | 230.47 | 0.53 |
| 4 | 14.4830 | 6.1161 | 2250.03 | 5.18 |
| 5 | 14.6445 | 6.0489 | 2087.24 | 4.80 |
| 6 | 15.0352 | 5.8926 | 24491.13 | 56.37 |
| 7 | 16.1972 | 5.4724 | 4882.98 | 11.24 |
| 8 | 18.3297 | 4.8403 | 1163.86 | 2.68 |
| 9 | 19.3304 | 4.5919 | 21985.48 | 50.61 |
| 10 | 19.6443 | 4.5192 | 4201.44 | 9.67 |
| 11 | 20.4537 | 4.3422 | 415.68 | 0.96 |
| 12 | 20.6760 | 4.2960 | 853.39 | 1.96 |
| 13 | 21.8332 | 4.0709 | 512.35 | 1.18 |
| 14 | 23.2910 | 3.8193 | 1605.99 | 3.70 |
| 15 | 23.4817 | 3.7887 | 833.22 | 1.92 |
| 16 | 24.0724 | 3.6970 | 1193.06 | 2.75 |
| 17 | 24.3417 | 3.6567 | 206.19 | 0.47 |
| 18 | 25.3319 | 3.5160 | 2946.98 | 6.78 |
| 19 | 25.6353 | 3.4751 | 12884.99 | 29.66 |
| 20 | 26.0027 | 3.4268 | 792.74 | 1.82 |
| 21 | 26.4025 | 3.3758 | 379.69 | 0.87 |
| 22 | 26.6586 | 3.3440 | 1452.11 | 3.34 |
| 23 | 26.8902 | 3.3157 | 8977.95 | 20.67 |
| 24 | 27.3465 | 3.2614 | 669.29 | 1.54 |
| 25 | 27.6420 | 3.2272 | 851.21 | 1.96 |
| 26 | 28.0770 | 3.1782 | 170.08 | 0.39 |
| 27 | 28.8367 | 3.0936 | 3283.34 | 7.56 |
| 28 | 28.8991 | 3.0896 | 2971.55 | 6.84 |
| 29 | 29.2181 | 3.0566 | 2745.79 | 6.32 |
| 30 | 29.5288 | 3.0251 | 1322.56 | 3.04 |
| 31 | 29.7824 | 2.9999 | 745.07 | 1.72 |
| 32 | 30.3801 | 2.9423 | 1745.50 | 4.02 |
| 33 | 30.9764 | 2.8870 | 120.51 | 0.28 |
| 34 | 31.9562 | 2.8007 | 698.88 | 1.61 |
| 35 | 32.4439 | 2.7597 | 445.29 | 1.02 |
| 36 | 32.9341 | 2.7197 | 341.20 | 0.79 |
| 37 | 33.9212 | 2.6428 | 438.82 | 1.01 |

TABLE 12

Listing of peaks with an intensity greater than 5% of the intensity of the peak at 7.96 °2θ

| No. | Pos. [°2θ] | Rel. Int. [%] |
|---|---|---|
| 2 | 7.9617 | 100.00 |
| 4 | 14.4830 | 5.18 |
| 6 | 15.0352 | 56.37 |
| 7 | 16.1972 | 11.24 |
| 9 | 19.3304 | 50.61 |
| 10 | 19.6443 | 9.67 |
| 18 | 25.3319 | 6.78 |
| 19 | 25.6353 | 29.66 |
| 23 | 26.8902 | 20.67 |
| 27 | 28.8367 | 7.56 |
| 28 | 28.8991 | 6.84 |
| 29 | 29.2181 | 6.32 |

Dynamic Vapour Sorption (DVS) Assessment for Solid Form B

Figure 15:
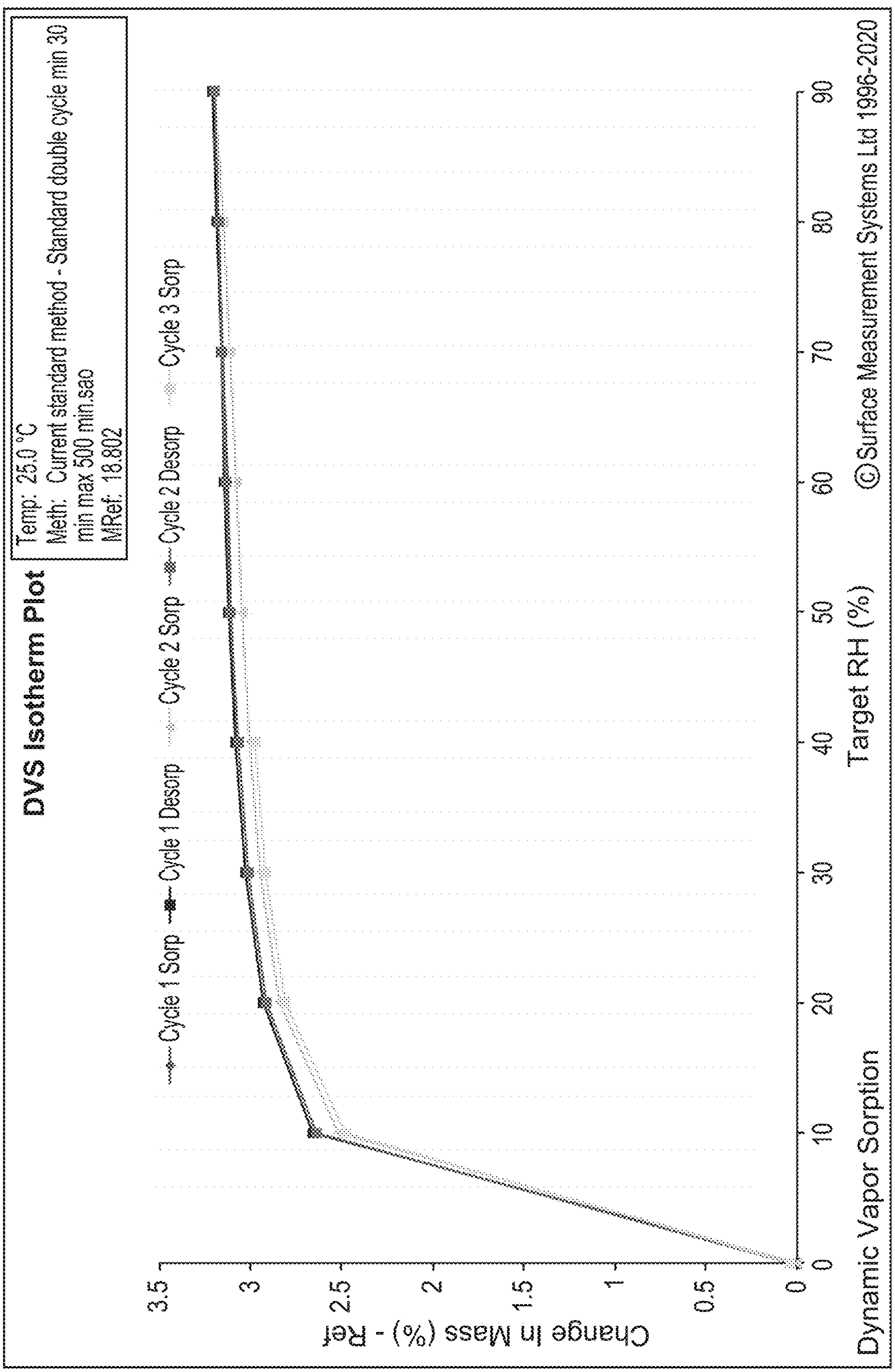
FIG. 15 is a dynamic vapor sorption (DVS) isotherm plot for Solid Form B.

DVS analysis of Solid Form B showed that the material had a large mass loss on de-sorption/uptake on sorption between 0 and 10% RH, ca. 2.6 wt. % (0.6 eq. water). Equilibration was not reached at 0% RH (maximum step time was 500 min), which indicated that de-hydration was incomplete. The DVS profile indicated that Solid Form B was hydrated. See FIG. 15.

DVS analysis of Solid Form B showed an uptake of 4.3 wt. % at 80% RH, although the uptake between 40 and 80% RH in the first sorption cycle was 0.2 wt. %. Below 10% RH dehydration occurred. After DVS analysis was completed, the XRPD diffractogram was consistent with Solid Form B with traces of Solid Form C.

Polarized Light Microscopy

Figure 16:
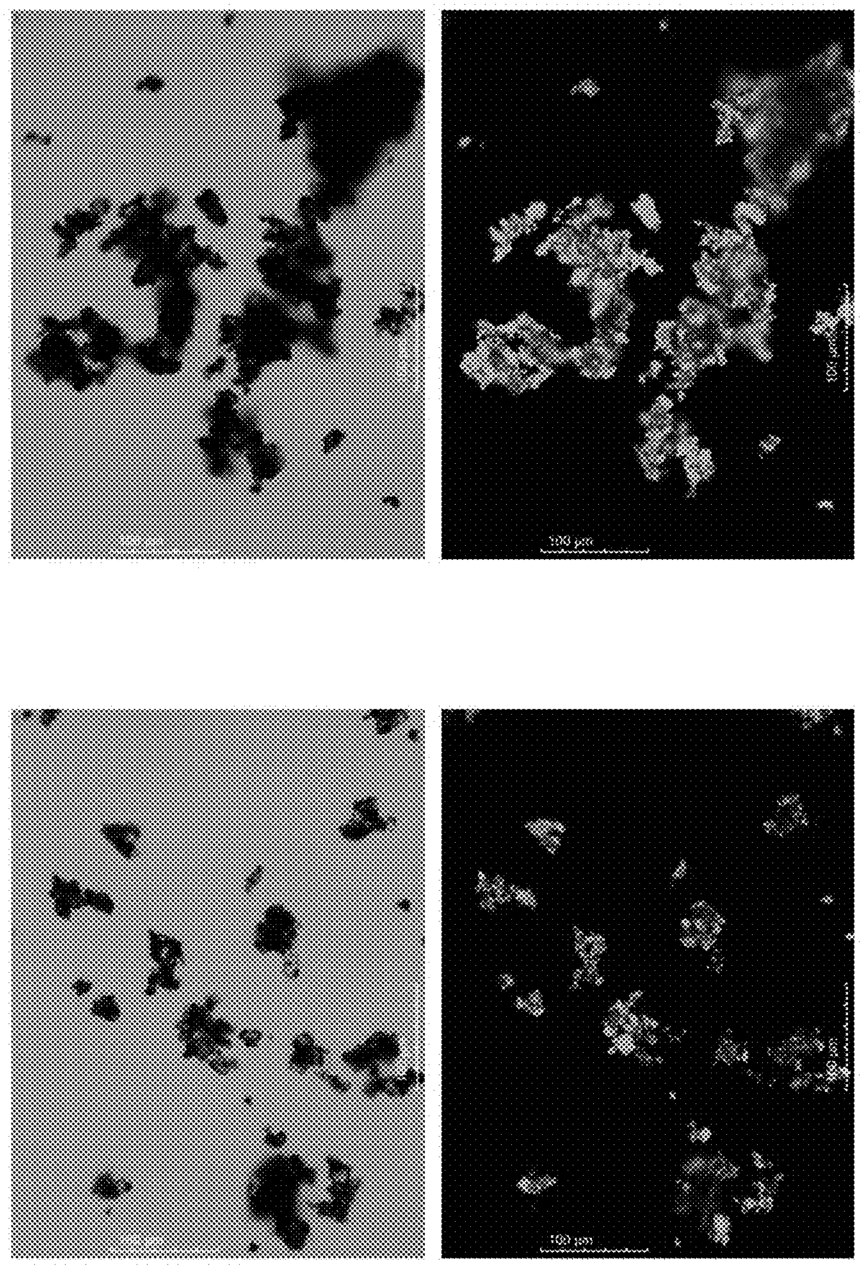
FIG. 16 is a set of polarized light microscopy (PLM) images of Solid Form B at ×20 magnification.
Figure 17:
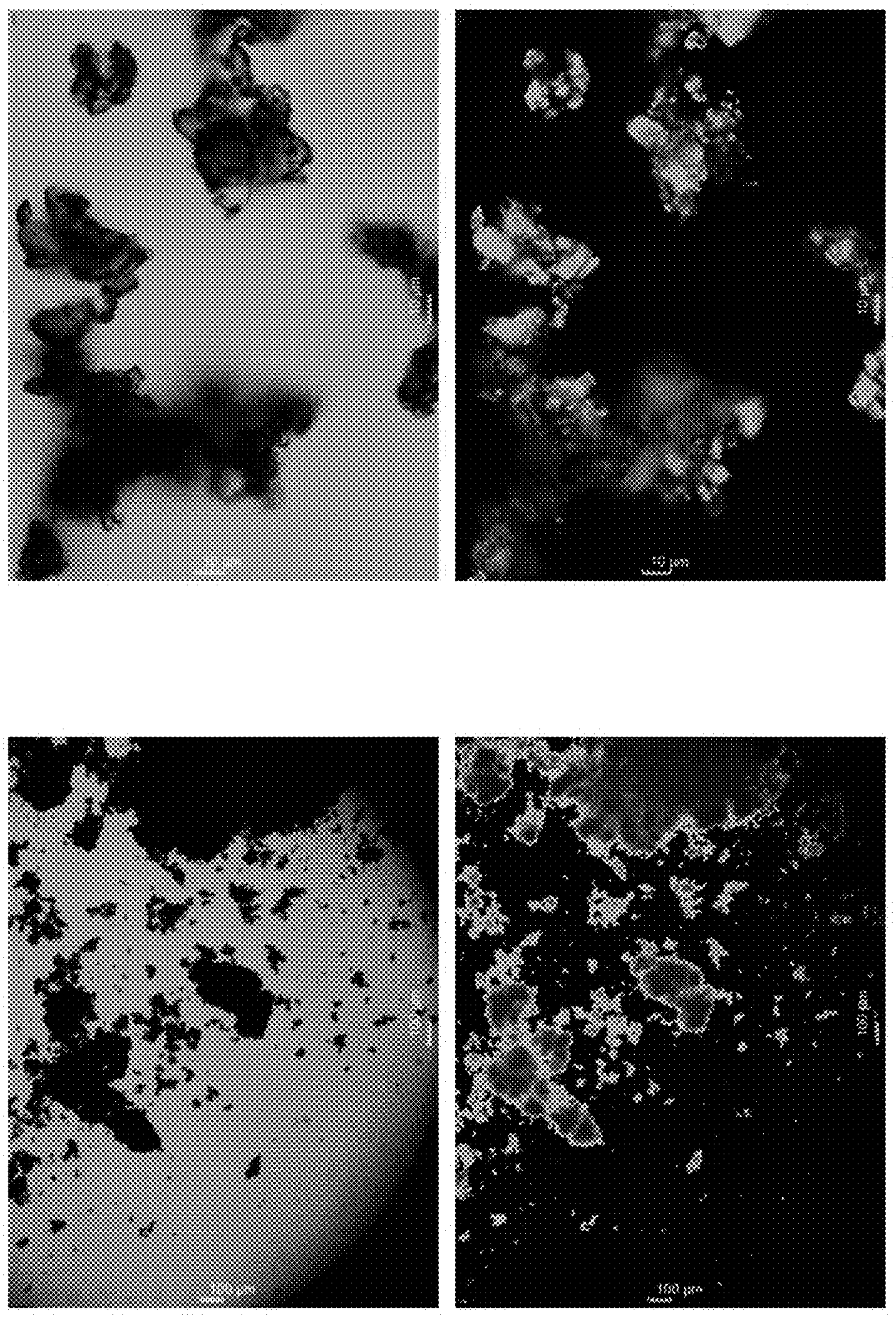
FIG. 17 is a set of polarized light microscopy (PLM) images of Solid Form B at ×5 (left) and ×50 (right) magnification.

PLM analysis showed that the material consisted of small aggregated birefringent crystals. See FIG. 16 and FIG. 17.

TG and DSC Analysis

TG analysis showed a weight loss of 4.2 wt. % from the onset of heating up to 100 °C, theoretically equivalent to 0.96 eq. of water. Simultaneous DSC analysis showed the following events: 1) broad endothermic event with an onset at 39.1 °C and peak at 84.8 °C, due to dehydration; 2) small endothermic event with an onset at 127.2 °C and peak at 131 °C, likely a soli-solid transition; and 3) sharp endothermic event with an onset at 161.8 °C and peak at 163.2 °C, the final melt event.

Standalone DSC analysis showed the following events in the first heat cycle: 1) broad endothermic event: Onset 86 °C, Peak 93.5 °C; 2) small endothermic event: Onset 128 °C, Peak 132.5 °C followed by very small exothermic event with onset at 133.3 °C and peak at 133.5 °C; and 3) sharp endothermic event: Onset 162.2 °C, Peak 163.6 °C On the cool and second heat cycle, glass transitions were observed in each with midpoints of 44.2 and 53.6 °C respectively.

Figure 18:
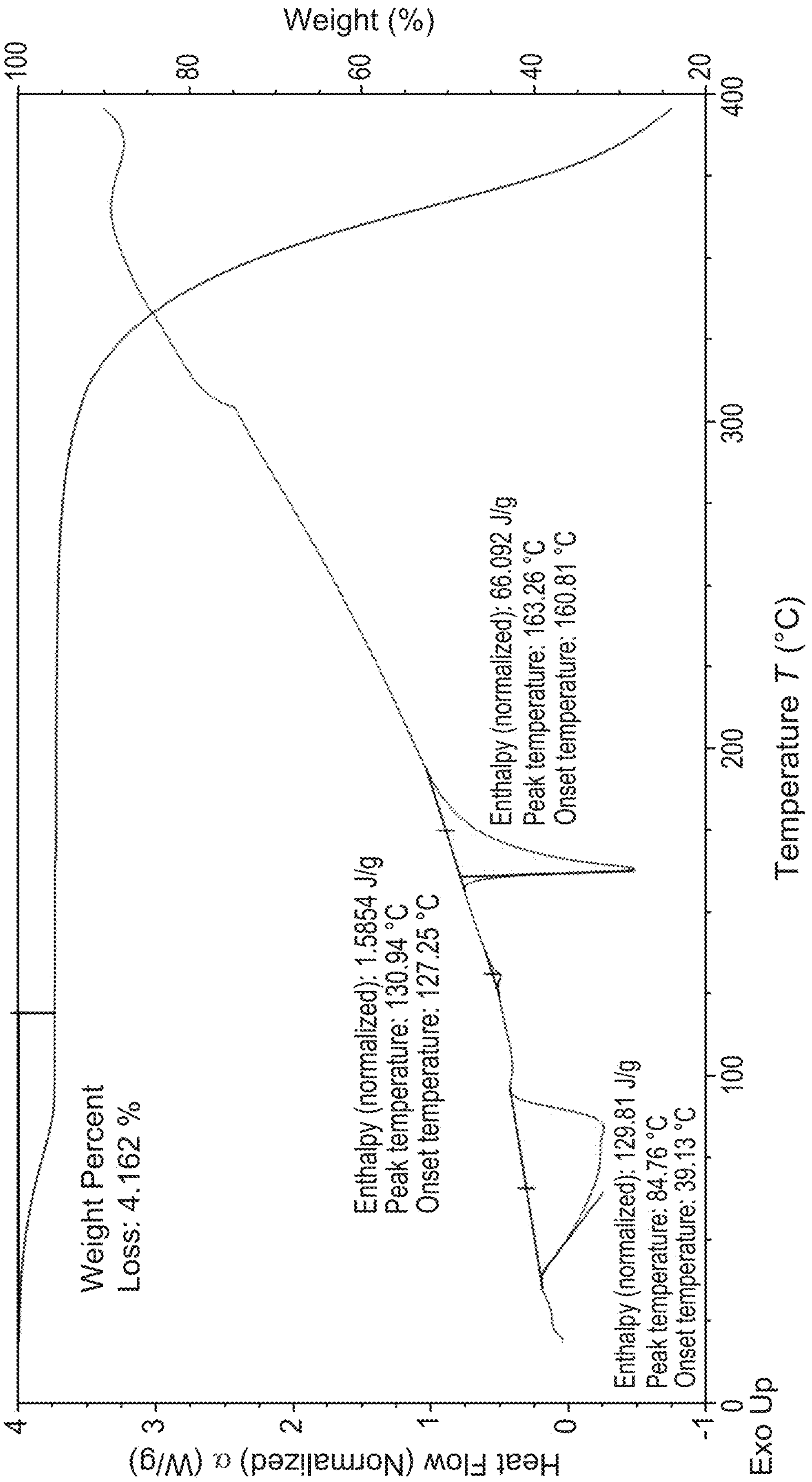
FIG. 18 is a differential scanning calorimetry and thermal gravimetric analysis thermogram (TG/DSC) of Solid Form B.

See FIG. 18 and FIG. 19.

Karl Fischer Titration

Karl Fischer analysis indicated that the material had a moisture content of 4.8 wt. % (average between duplicate measurements), theoretically equivalent to 1.1 eq. of water.

7-Day Stability Assessment of Solid Form B

The stability assessment was conducted as follows:

15 mg of Solid Form B was weighed into 3×1.5 ml vials.

One vial was left uncapped, placed inside a scintillation vial and stored at ambient conditions (ca. 20 °C).

One vial was left uncapped and placed inside a scintillation vial. This was placed in a stability oven at 40 °C/75% RH.

Figure 21:
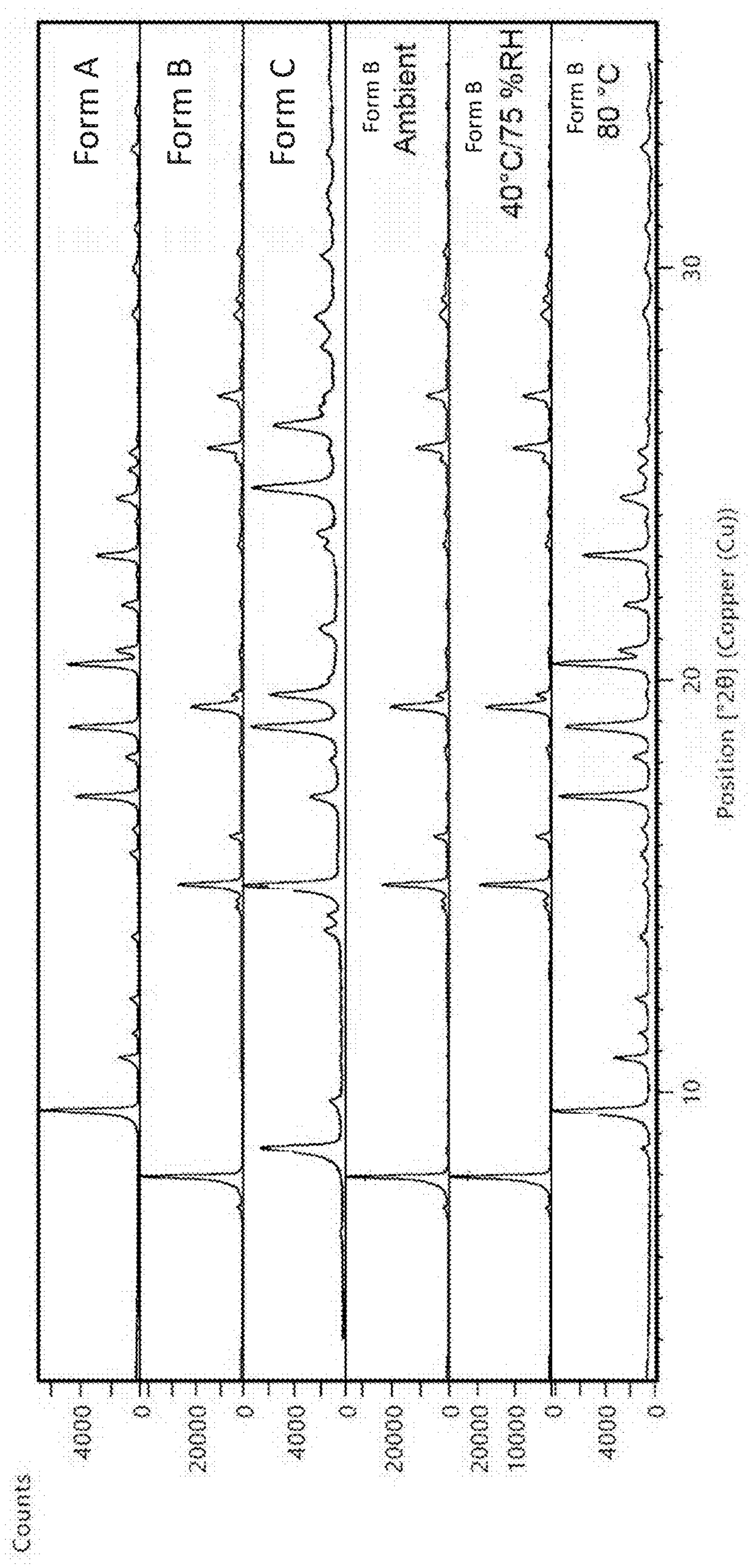
FIG. 21 is a set of XRPD of 7-day stability assessment of Solid Form B.

One vial was capped and placed inside a scintillation vial. This was placed inside an oven at 80 °C After 7 days the samples were removed from their respective conditions, analyzed by XRPD and submitted for HPLC analysis. The XRPD results are summarized in FIG. 21.

7-day stability analysis (Table 13) showed that there was no drop in purity across the conditions investigated. Solid Form B was retained at ambient temperature and 40 °C/75% RH, however, Solid Form B was converted to a mixture of Solid Form A and Solid Form C at 80 °C

TABLE 13

Solid Form B Seven Day Stability Results

| Input | Condition | HPLC purity (% rel. Area) | XRPD |
|---|---|---|---|
| Solid Form B (Input purity: 100%) | Ambient Light | 100 | Solid Form B |
| | 40 °C/75% RH | 100 | Solid Form B |
| | 80 °C | 100 | Solid Form A + Solid Form C |

VH-XRPD Analysis of Solid Form B

Variable humidity XRPD was carried out using the following method:

A diffractogram was collected once each targeted % RH was reached and after the reported time had elapsed (Table 14 below).

After 20 hours at 2% RH, some $P_2O_5$ was introduced within the stage chamber with the aim of further dry the environment.

The sample was kept at these conditions for further 16 hours, during which a diffractogram was collected every hour.

TABLE 14

Experimental Details of VH-XRPD Analysis of Solid Form B

| % RH | Time (hours) |
|---|---|
| 40 | 0.0 |
| 90 | 0.5 |
| 40 | 0.5 |
| 10 | 1.0 |
| 2 | 0.5 |
| 2 | 20.0 |

Figure 22:
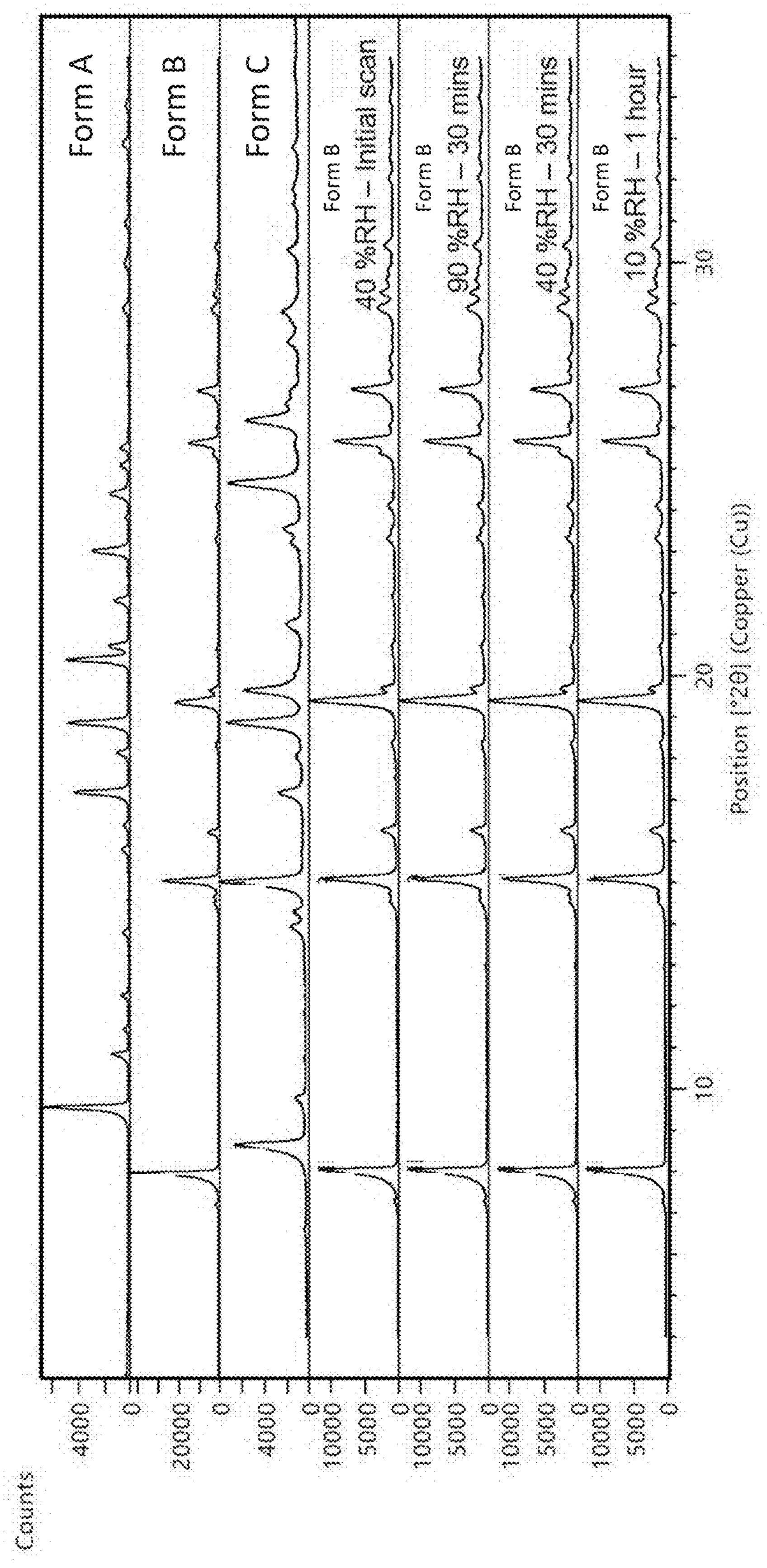
FIG. 22 is a set of VH-XRPD of Solid Form B.
Figure 23:
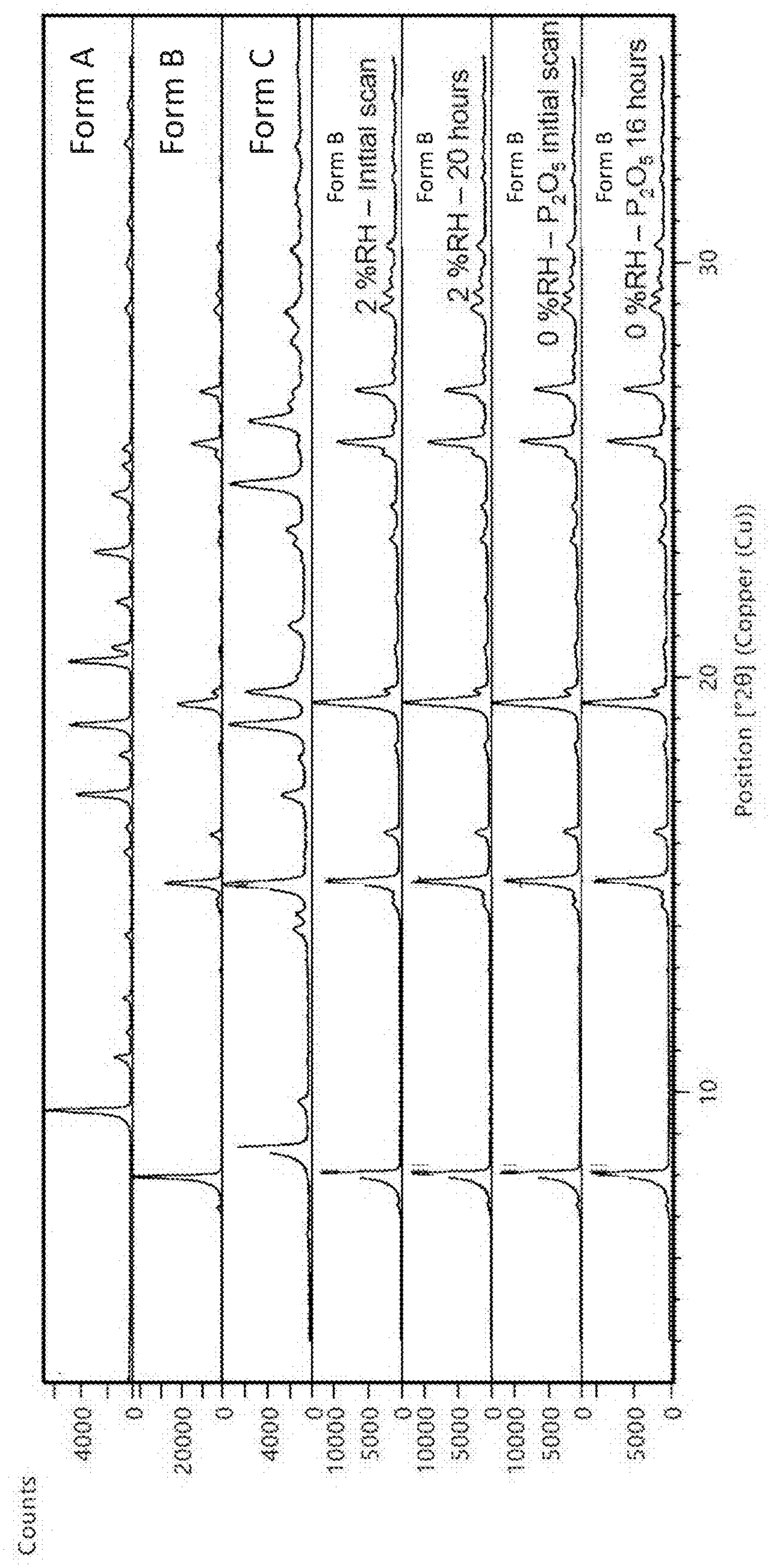
FIG. 23 is a set of VH-XRPD of Solid Form B.
Figure 24:
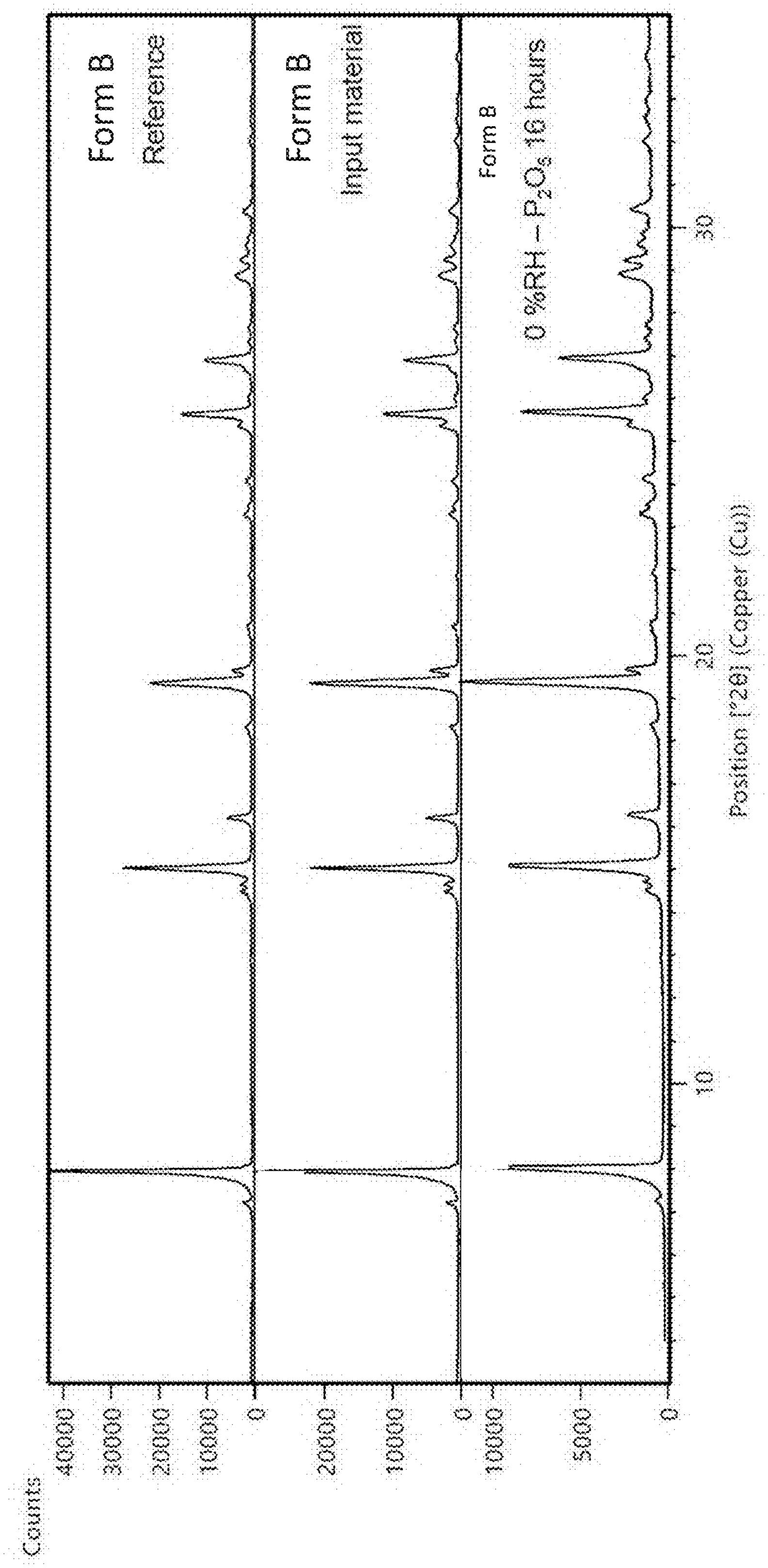
FIG. 24 is a set of VH-XRPD of Solid Form B.

VH-XRPD analysis of Solid Form B showed that there was no change in form during the experiment. See Table 15 as well as FIG. 22, FIG. 23, and FIG. 24

TABLE 15

Results of VH-XRPD Analysis of Solid Form B

| % RH | Time (hours) | XRPD |
|---|---|---|
| 40 | 0 | Solid Form B |
| 90 | 0.5 | Solid Form B |
| 40 | 0.5 | Solid Form B |
| 10 | 1 | Solid Form B |
| 2 | 0.5 | Solid Form B |
| 2 | 20 | Solid Form B |

Thermodynamic Solubility Assessment of Solid Form B

A thermodynamic solubility assessment was conducted as follows:

25 mg of Solid Form B was weighed into 3×1.5 ml vials.

To each one, 250 μL of the appropriate buffer was added, obtaining a slurry.

The samples were placed on an incubator shaker at 25 °C for 1 hour.

After 1 hour, the pH value was measured and adjusted accordingly.

The samples were returned to the incubator shaker for 24 hours.

After 16 hours, the samples for pH 1.2 and 4.5 were clear solutions, therefore more material was added, and the samples returned to the shaker.

After 24 hours, the pH was measured again and adjusted accordingly.

The samples were syringe-filtered, the mother liquor was submitted for HPLC to determine the concentration of dissolved free base, whilst the solid was analyzed by XRPD.

Figure 25:
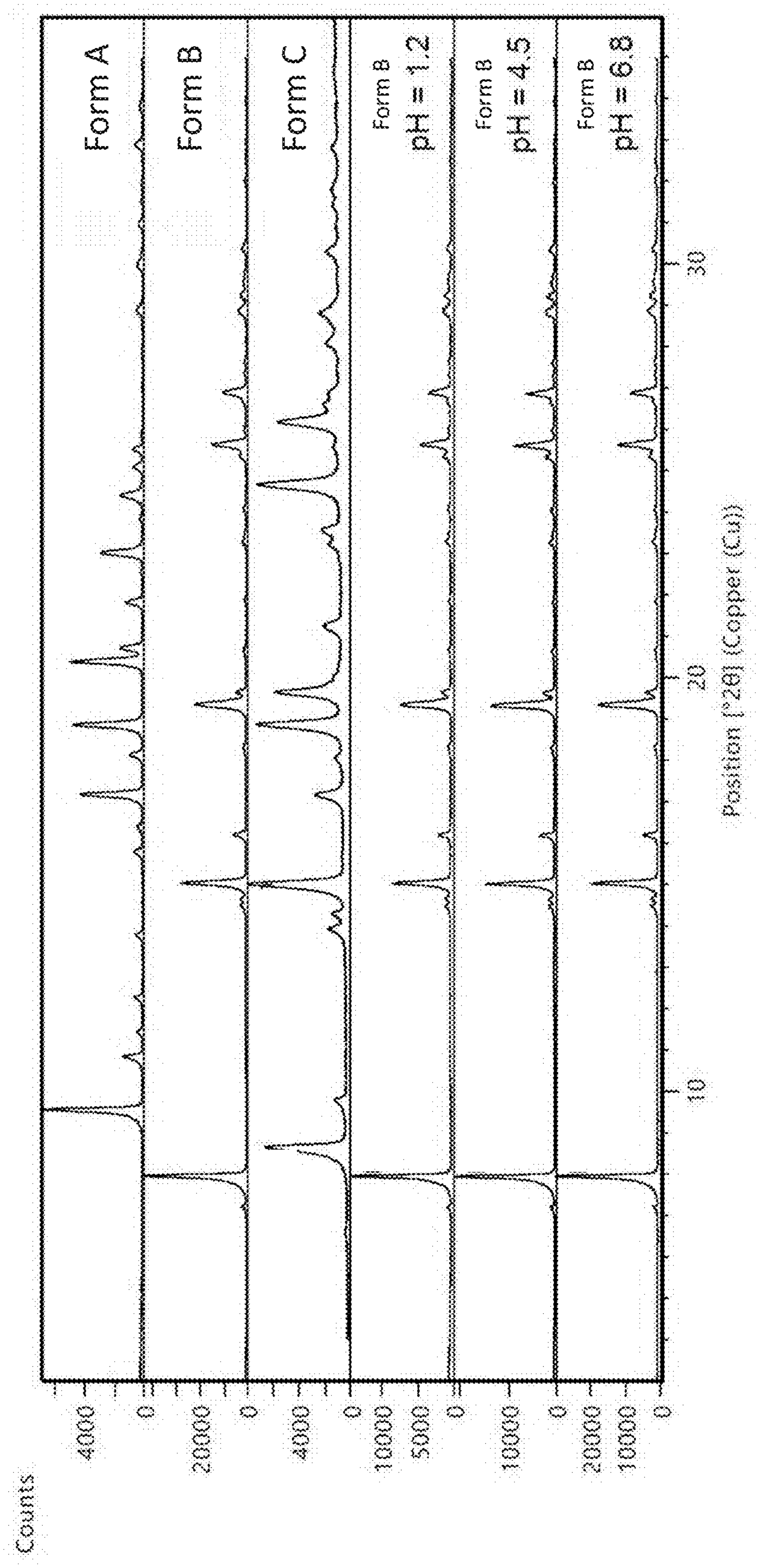
FIG. 25 is a set of XRPD of thermodynamic solubility assessment of Solid Form B.

Results are summarized in Table 16 below and plotted in FIG. 25.

The thermodynamic solubility assessment (Table 16) showed that Solid Form B had high solubility (>150 mg/mL) at pH 4.5. Solid Form B was retained across the pH range.

TABLE 16

Results of the Thermodynamic Solubility Assessment of Solid Form B

| Input | pH value | HPLC conc. (mg/mL) | XRPD Pattern |
|---|---|---|---|
| Solid Form B | 1.2 | 46.7 | Solid Form B |
| | 4.5 | 162.4 | Solid Form B |
| | 6.8 | 21.8 | Solid Form B |

Example 3. Solid Form C

Solid Form C was observed during the VT-XRPD analysis of Solid Form B at 85 °C

Solid Form C was also observed multiple times during the polymorph screen, however only as a mixture with Solid Form A or Solid Form B. Multiple attempts were made to re-prepare Solid Form C, however again, it was only observed as a mixture with Solid Form A and Solid Form B.

TABLE 17

| XRPD Peak List of Solid Form C | | | | |
|---|---|---|---|---|
| No. | Pos. [°2θ] | d-spacing [Å] | Height [cts] | Rel. Int. [%] |
| 1 | 6.5940 | 13.4048 | 160.30 | 2.31 |
| 2 | 8.6307 | 10.2456 | 6074.75 | 87.65 |
| 3 | 8.6800 | 10.1875 | 5856.79 | 84.50 |
| 4 | 9.8297 | 8.9984 | 798.79 | 11.53 |
| 5 | 10.7748 | 8.2112 | 37.04 | 0.53 |
| 6 | 13.9580 | 6.3449 | 1189.92 | 17.17 |
| 7 | 14.3052 | 6.1917 | 1010.99 | 14.59 |
| 8 | 15.0544 | 5.8852 | 6930.81 | 100.00 |
| 9 | 15.6976 | 5.6454 | 304.35 | 4.39 |
| 10 | 17.2160 | 5.1508 | 2107.25 | 30.40 |
| 11 | 18.0435 | 4.9164 | 775.25 | 11.19 |
| 12 | 18.8879 | 4.6985 | 6745.32 | 97.32 |
| 13 | 19.6118 | 4.5229 | 4674.04 | 67.44 |
| 14 | 19.6608 | 4.5155 | 5349.12 | 77.18 |
| 15 | 20.0644 | 4.4256 | 913.09 | 13.17 |
| 16 | 21.3028 | 4.1710 | 1512.58 | 21.82 |
| 17 | 23.2634 | 3.8237 | 1258.88 | 18.16 |
| 18 | 23.5960 | 3.7706 | 1785.39 | 25.76 |
| 19 | 24.6607 | 3.6101 | 6690.06 | 96.53 |
| 20 | 25.5933 | 3.4807 | 929.11 | 13.41 |
| 21 | 26.1792 | 3.4041 | 5062.74 | 73.05 |
| 22 | 26.6081 | 3.3502 | 1704.39 | 24.59 |
| 23 | 26.9510 | 3.3083 | 1170.64 | 16.89 |
| 24 | 27.5251 | 3.2406 | 682.87 | 9.85 |
| 25 | 28.1084 | 3.1747 | 1485.63 | 21.44 |
| 26 | 28.8196 | 3.0979 | 1914.84 | 27.63 |
| 27 | 29.6231 | 3.0157 | 692.86 | 10.00 |
| 28 | 30.3217 | 2.9478 | 1470.77 | 21.22 |
| 29 | 30.9037 | 2.8936 | 722.32 | 10.42 |
| 30 | 31.4328 | 2.8461 | 1011.39 | 14.59 |
| 31 | 31.8088 | 2.8133 | 1057.64 | 15.26 |
| 32 | 32.7826 | 2.7319 | 1061.85 | 15.32 |
| 33 | 34.6364 | 2.5898 | 877.23 | 12.66 |

TABLE 18

| Listing of peaks with an intensity greater than 20% of the intensity of the peak at 15.01 °2θ | | |
|---|---|---|
| No. | Pos. [°2θ] | Rel. Int. [%] |
| 2 | 8.6307 | 87.65 |
| 3 | 8.6800 | 84.50 |
| 8 | 15.0544 | 100.00 |
| 10 | 17.2160 | 30.40 |
| 12 | 18.8879 | 97.32 |
| 13 | 19.6118 | 67.44 |
| 14 | 19.6608 | 77.18 |
| 16 | 21.3028 | 21.82 |
| 18 | 23.5960 | 25.76 |
| 19 | 24.6607 | 96.53 |
| 21 | 26.1792 | 73.05 |
| 22 | 26.6081 | 24.59 |
| 25 | 28.1084 | 21.44 |
| 26 | 28.8196 | 27.63 |
| 28 | 30.3217 | 21.22 |

Example 4. Solid Form D

Preparation of Solid Form D

The following methods were used for the preparation of Solid Form D: 500 mg of crystalline Form A was weighed in a scintillation vial. A stirrer bar was added and 12.5 mL of water was added, obtaining a slurry. The vial was placed in a temperature-controlled block set a 25 °C and magnetically stirred for 48 hours.

After 48 hours an aliquot was taken from the slurry and solid material was isolated via centrifugation. The solid was analyzed by XRPD, resulting in Form D. XRPD 2θ diffractogram from single crystal growth experiment of Form D are shown in FIG. 27.

XRPD Analysis of Solid Form D

TABLE 19

| XRPD Peak List of Solid Form D | | | | |
|---|---|---|---|---|
| No. | Pos. [°2θ] | d-spacing [Å] | Height [cts] | Rel. Int. [%] |
| 1 | 6.7620 | 13.07226 | 14643.11 | 82.97 |
| 2 | 9.0830 | 9.73640 | 17648.08 | 100.00 |
| 3 | 10.0437 | 8.80716 | 176.33 | 1.00 |
| 4 | 10.3865 | 8.51723 | 407.05 | 2.31 |
| 5 | 11.0162 | 8.03175 | 403.98 | 2.29 |
| 6 | 13.3875 | 6.61394 | 2457.34 | 13.92 |
| 7 | 13.5658 | 6.52743 | 6533.47 | 37.02 |
| 8 | 14.3106 | 6.18932 | 7353.04 | 41.66 |
| 9 | 15.5483 | 5.69931 | 10816.56 | 61.29 |
| 10 | 15.7841 | 5.61470 | 2901.69 | 16.44 |
| 11 | 16.3531 | 5.42058 | 2566.49 | 14.54 |
| 12 | 16.7632 | 5.28888 | 558.31 | 3.16 |
| 13 | 16.9901 | 5.21877 | 1064.18 | 6.03 |
| 14 | 17.6541 | 5.02394 | 184.39 | 1.04 |
| 15 | 18.5794 | 4.77577 | 6668.21 | 37.78 |
| 16 | 19.3010 | 4.59882 | 1475.44 | 8.36 |
| 17 | 19.7364 | 4.49834 | 1100.39 | 6.24 |
| 18 | 20.1838 | 4.39963 | 470.46 | 2.67 |
| 19 | 20.4187 | 4.34954 | 1858.07 | 10.53 |
| 20 | 20.8796 | 4.25457 | 5506.96 | 31.20 |
| 21 | 21.2145 | 4.18814 | 5111.63 | 28.96 |
| 22 | 21.7605 | 4.08429 | 1605.01 | 9.09 |
| 23 | 22.2032 | 4.00384 | 386.65 | 2.19 |
| 24 | 22.7825 | 3.90332 | 1035.78 | 5.87 |
| 25 | 23.3931 | 3.80280 | 1803.73 | 10.22 |
| 26 | 23.7498 | 3.74650 | 791.04 | 4.48 |
| 27 | 24.0917 | 3.69409 | 1200.25 | 6.80 |
| 28 | 24.3098 | 3.66144 | 2123.67 | 12.03 |
| 29 | 24.4864 | 3.63544 | 4167.43 | 23.61 |
| 30 | 25.0330 | 3.55728 | 720.96 | 4.09 |
| 31 | 25.3756 | 3.51003 | 3340.21 | 18.93 |
| 32 | 25.7717 | 3.45697 | 9467.20 | 53.64 |
| 33 | 26.2770 | 3.39163 | 3753.30 | 21.27 |
| 34 | 26.6857 | 3.34061 | 1158.03 | 6.56 |
| 35 | 27.0129 | 3.30088 | 2672.58 | 15.14 |
| 36 | 27.4745 | 3.24647 | 5244.37 | 29.72 |
| 37 | 27.7394 | 3.21606 | 5222.94 | 29.59 |
| 38 | 28.1211 | 3.17327 | 1073.50 | 6.08 |
| 39 | 28.8764 | 3.09196 | 2095.02 | 11.87 |
| 40 | 29.3707 | 3.04104 | 1053.22 | 5.97 |
| 41 | 30.0210 | 2.97664 | 1086.94 | 6.16 |
| 42 | 30.4091 | 2.93953 | 1065.67 | 6.04 |
| 43 | 30.8070 | 2.90246 | 1101.07 | 6.24 |
| 44 | 31.0792 | 2.87766 | 640.52 | 3.63 |
| 45 | 31.6352 | 2.82834 | 756.80 | 4.29 |
| 46 | 31.8773 | 2.80741 | 1025.13 | 5.81 |
| 47 | 32.1103 | 2.78757 | 808.63 | 4.58 |
| 48 | 32.6600 | 2.74190 | 1011.84 | 5.73 |
| 49 | 32.9844 | 2.71567 | 562.37 | 3.19 |
| 50 | 33.5978 | 2.66748 | 527.31 | 2.99 |
| 51 | 33.9302 | 2.64211 | 704.05 | 3.99 |
| 52 | 34.3658 | 2.60961 | 522.73 | 2.96 |

TABLE 20

| XRPD Peak List of Solid Form D (20 most intense peaks) | | | | |
|---|---|---|---|---|
| No. | Pos. [°2θ] | d-spacing [Å] | Height [cts] | Rel. Int. [%] |
| 1 | 9.0830 | 9.73640 | 17648.08 | 100.00 |
| 2 | 6.7620 | 13.07226 | 14643.11 | 82.97 |
| 6 | 15.5483 | 5.69931 | 10816.56 | 61.29 |
| 7 | 25.7717 | 3.45697 | 9467.20 | 53.64 |
| 8 | 14.3106 | 6.18932 | 7353.04 | 41.66 |
| 9 | 18.5794 | 4.77577 | 6668.21 | 37.78 |

TABLE 20-continued

| XRPD Peak List of Solid Form D (20 most intense peaks) | | | | |
|---|---|---|---|---|
| No. | Pos. [°2θ] | d-spacing [Å] | Height [cts] | Rel. Int. [%] |
| 10 | 13.5658 | 6.52743 | 6533.47 | 37.02 |
| 11 | 20.8796 | 4.25457 | 5506.96 | 31.20 |
| 15 | 27.4745 | 3.24647 | 5244.37 | 29.72 |
| 20 | 27.7394 | 3.21606 | 5222.94 | 29.59 |
| 21 | 21.2145 | 4.18814 | 5111.63 | 28.96 |
| 28 | 24.4864 | 3.63544 | 4167.43 | 23.61 |
| 29 | 26.2770 | 3.39163 | 3753.30 | 21.27 |
| 31 | 25.3756 | 3.51003 | 3340.21 | 18.93 |
| 32 | 15.7841 | 5.61470 | 2901.69 | 16.44 |
| 33 | 27.0129 | 3.30088 | 2672.58 | 15.14 |
| 35 | 16.3531 | 5.42058 | 2566.49 | 14.54 |
| 36 | 13.3875 | 6.61394 | 2457.34 | 13.92 |
| 37 | 24.3098 | 3.66144 | 2123.67 | 12.03 |
| 39 | 28.8764 | 3.09196 | 2095.02 | 11.87 |

Differential Scanning Calorimetry/Thermal Gravimetric Analysis

Figure 28:
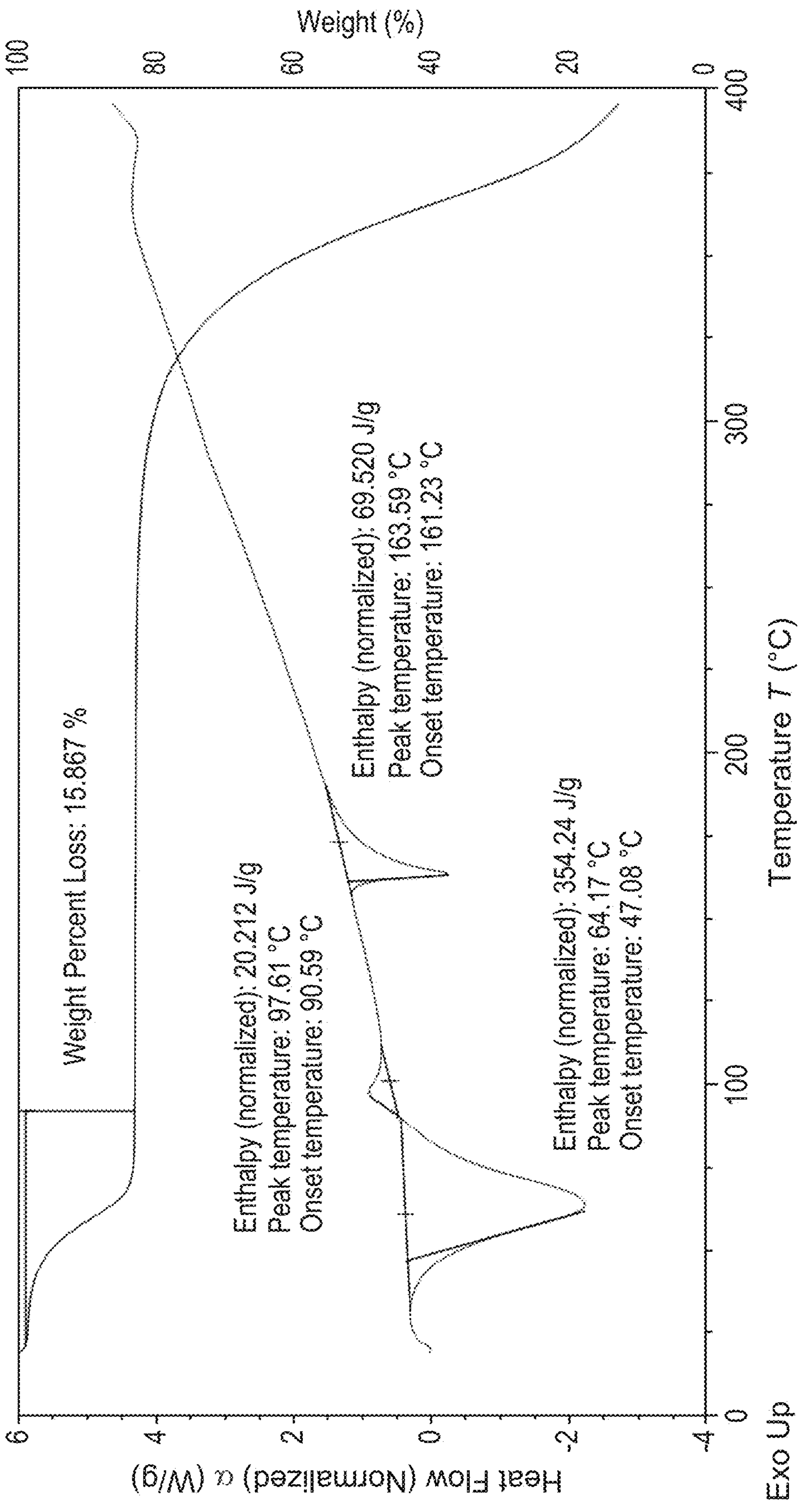
FIG. 28 is a differential scanning calorimetry and thermal gravimetric analysis thermogram (TG/DSC) of Solid Form D.

The TG trace showed a weight loss of 15.87 wt. % from the onset of heating to 90 °C, theoretically equivalent to 4.14 eq. of water. The DSC trace showed a large endothermic event with onset at 47.1 °C and peak at 64.2 °C, concomitant with the weight loss seen in the TG trace; a small exothermic event with onset at 90.6 °C and peak at 97.6 °C and a second endothermic event with onset at 161.2 °C and peak at 163.6 °C. The TG/DSC characterization of Form D is shown in FIG. 28.

Karl-Fischer Analysis

Water content analysis was carried out via direct addition of material to the titrator. The analysis was carried out in duplicate and the results averaged. Water content (average): 15.82%, which is equivalent to 4.13 eq. of water.

EQUIVALENTS

Those skilled in the art will recognize, or be able to ascertain, using no more than routine experimentation, numerous equivalents to the specific embodiments described specifically herein. Such equivalents are intended to be encompassed in the scope of the following claims.

What claimed is:

1. A method of treating heart failure, comprising administering to a subject in need thereof a solid form of Compound X:

(X)

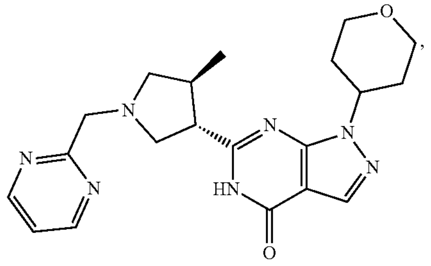

wherein the solid form is selected from:

Form A: characterized by having X-ray powder diffraction peaks at approximately 18.9, 20.4, and 23.1°2θ using Cu Kα radiation, Form B: characterized by having X-ray powder diffraction peaks at approximately 8.0, 15.0, and 19.3°2θ using Cu Kα radiation, Form C: characterized by having X-ray powder diffraction peaks at approximately 15.0, 18.9, and 24.7°2θ using Cu Kα radiation, and Form D: characterized by having X-ray powder diffraction peaks at approximately 6.8, 9.1, and 15.5°2θ using Cu Kα radiation.

2. The method of claim 1, wherein the solid form is Form A.

3. The method of claim 1, wherein the solid form is Form B.

4. The method of claim 1, wherein the solid form is Form C.

5. The method of claim 1, wherein the solid form is Form D.

6. The method of claim 1, wherein the heart failure is congestive heart failure.

7. A pharmaceutical composition comprising a solid form of Compound X:

(X)

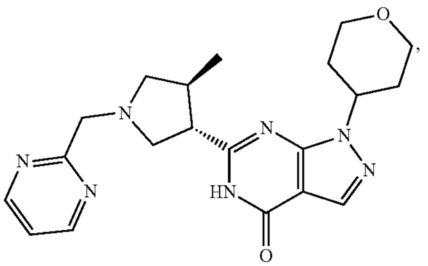

and a pharmaceutically acceptable excipient, wherein the solid form is selected from:

Form A: characterized by having X-ray powder diffraction peaks at approximately 18.9, 20.4, and 23.1°2θ using Cu Kα radiation, Form B: characterized by having X-ray powder diffraction peaks at approximately 8.0, 15.0, and 19.3°2θ using Cu Kα radiation, Form C: characterized by having X-ray powder diffraction peaks at approximately 15.0, 18.9, and 24.7°2θ using Cu Kα radiation, and Form D: characterized by having X-ray powder diffraction peaks at approximately 6.8, 9.1, and 15.5°2θ using Cu Kα radiation.

8. The pharmaceutical composition of claim 7, wherein the solid form is Form A.

9. The pharmaceutical composition of claim 8, wherein the Form A is characterized by having X-ray powder diffraction peaks at 9.6±0.2, 17.2±0.2, 18.9±0.2, 20.4±0.2, and 23.1±0.2°2θ using Cu Kα radiation.

10. The pharmaceutical composition of claim 8, wherein the Form A is characterized by having X-ray powder diffraction peaks at 9.6±0.2, 17.2±0.2, 18.9±0.2, 20.4±0.2, 20.7±0.2, 21.9±0.2, 23.1±0.2, and 24.5±0.2°2θ using Cu Kα radiation.

11. The pharmaceutical composition of claim 7, wherein the solid form is Form B.

12. The pharmaceutical composition of claim 11, wherein the Form B is characterized by having X-ray powder diffraction peaks at 8.0±0.2, 15.0±0.2, 19.3±0.2, 25.6±0.2, and 26.9±0.2°2θ using Cu Kα radiation.

13. The pharmaceutical composition of claim 11, wherein the Form B is characterized by having X-ray powder diffraction peaks at 8.0±0.2, 15.0±0.2, 16.2±0.2, 19.3±0.2, 19.6±0.2, 25.6±0.2, and 26.9±0.2°2θ using Cu Kα radiation.

14. The pharmaceutical composition of claim 7, wherein the solid form is Form C.

15. The pharmaceutical composition of claim 14, wherein the Form C is characterized by having X-ray powder diffraction peaks at 8.6±0.2, 8.7±0.2, 15.0±0.2, 18.9±0.2, and 24.7±0.2°2θ using Cu Kα radiation.

16. The pharmaceutical composition of claim 14, wherein the Form C is characterized by having X-ray powder diffraction peaks at 8.6±0.2, 8.7±0.2, 15.0±0.2, 18.9±0.2, 19.6±0.2, 19.7±0.2, 24.7±0.2, and 26.2±0.2°2θ using Cu Kα radiation.

17. The pharmaceutical composition claim 7, wherein the solid form is Form D.

18. The pharmaceutical composition of claim 17, wherein the Form D is characterized by having X-ray powder diffraction peaks at 6.8±0.2, 9.1±0.2, 14.3±0.2, 15.5±0.2, and 25.8±0.2°2θ using Cu Kα radiation.

19. The pharmaceutical composition of claim 17, wherein the Form D is characterized by having X-ray powder diffraction peaks at 6.8±0.2, 9.1±0.2, 13.6±0.2, 14.3±0.2, 15.5±0.2, 18.6±0.2, and 25.8±0.2°2θ using Cu Kα radiation.

* * * * *